(12) United States Patent
Ashweek et al.

(10) Patent No.: US 11,053,242 B2
(45) Date of Patent: *Jul. 6, 2021

(54) [9,10-DIMETHOXY-3-(2-METHYLPROPYL)-1H,2H,3H,4H,6H,7H,11BH-PYRIDO-[2,1-A]ISOQUINOLIN-2-YL]METHANOL AND COMPOUNDS, COMPOSITIONS AND METHODS RELATING THERETO

(71) Applicant: Neurocrine Biosciences, Inc., San Diego, CA (US)

(72) Inventors: Neil Ashweek, Escondido, CA (US); Nicole Harriott, San Diego, CA (US)

(73) Assignee: Neurocrine Biosciences, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/748,999

(22) Filed: Jan. 22, 2020

(65) Prior Publication Data
US 2020/0262834 A1 Aug. 20, 2020

Related U.S. Application Data

(63) Continuation of application No. 15/967,187, filed on Apr. 30, 2018, now abandoned, which is a continuation of application No. 15/627,145, filed on Jun. 19, 2017, now Pat. No. 9,988,382, which is a continuation of application No. 15/017,480, filed on Feb. 5, 2016, now Pat. No. 9,714,246.

(60) Provisional application No. 62/113,316, filed on Feb. 6, 2015.

(51) Int. Cl.
C07D 471/04 (2006.01)
C07D 455/04 (2006.01)
C07D 519/00 (2006.01)

(52) U.S. Cl.
CPC ......... *C07D 471/04* (2013.01); *C07D 455/04* (2013.01); *C07D 519/00* (2013.01)

(58) Field of Classification Search
CPC ... C07D 471/04; C07D 455/04; C07D 519/00
See application file for complete search history.

(56) References Cited

U.S. PATENT DOCUMENTS

| | | | |
|---|---|---|---|
| 9,714,246 B2 | 7/2017 | Ashweek et al. | |
| 9,782,398 B2 | 10/2017 | Hoare et al. | |
| 9,988,382 B2 | 6/2018 | Ashweek et al. | |
| 2016/0289226 A1 | 10/2016 | Ashweek et al. | |
| 2017/0349586 A1 | 12/2017 | Ashweek et al. | |
| 2018/0273533 A1 | 9/2018 | Ashweek et al. | |

FOREIGN PATENT DOCUMENTS

| | | |
|---|---|---|
| JP | 54125699 | 9/1979 |
| RU | 2339363 | 11/2008 |
| WO | WO 2008/058261 | 5/2008 |
| WO | WO 2015/120317 | 8/2015 |

OTHER PUBLICATIONS

Aranda et al., "Synthesis and Biological Activity of Iodinated and Photosensitive Derivatives of Tetrabenazine," European Journal of Medicinal Chemistry, Jan. 1, 1990, 25:369-374.
Bundgaard H. "Design of prodrugs: Bioreversible derivatives for various functional groups and chemical entities," In Design of prodrugs Jan. 1985, 7-9, 21-24.
Chinese Office Action in Appln. No. 201680008945.5, dated Mar. 19, 2019, 12 pages (with English translation).
European Office Action in European Application No. 16705684.5, dated Sep. 7, 2018, 8 pages.
Gibbs et al., "Minimizing Polymorphic Metabolism in Drug Discovery: Evaluation of the Utility of in Vitro Methods for Predicting Pharmacokinetic Consequences Associated with CYP2D6 Metabolism," Drug Metab Dispos., Sep. 2006, 34(9)1516-1522.
Hoare et al., "Conformational states of the corticotropin releasing factor 1 (CRF1) receptor: detection, and pharmacological evaluation by peptide ligands," Peptides, Dec. 2003, 24(12):1881-1897.
International Preliminary Report on Patentability in International Application No. PCT/US2016/01689, dated Aug. 8, 2017, 8 pages.
International Search Report and Written Opinion in International Application No. PCT/US2016/016892, dated Mar. 22, 2016, 13 pages.
Kilbourn et al., "Absolute Configuration of (+)-alpha-Dihydrotetrabenazine, an Active Metabolite of Tetrabenazine," Chiralty, Jan. 1, 1997, 9:59-62.
Kimiagar et al., "Rapid improvement of tardive dyskinesia with tetrabenazine, clonazepam and clozapine combined: a naturalistic long-term follow-up study," Journal of Neurology, 2011, 259(4):660-664.

(Continued)

*Primary Examiner* — Rebecca L Anderson
(74) *Attorney, Agent, or Firm* — Fish & Richardson P.C.

(57) ABSTRACT

Compounds having a structure of formula (I), including stereoisomers and pharmaceutically acceptable salts and solvates thereof:

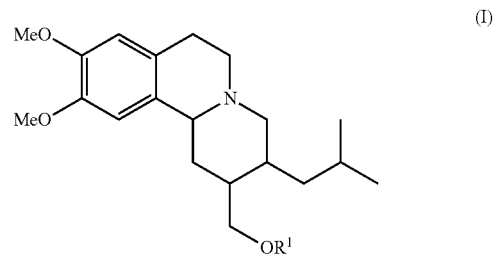

(I)

wherein $R_1$ is as defined herein. Such compounds are inhibitors of the vesicular monoamine transporter 2 (VMAT2) and have utility for treating, for example, hyperkinetic disorders. Also disclosed are compositions containing these compounds in combination with a pharmaceutically acceptable carrier or diluent, as well as methods relating to the use in a subject in need thereof.

20 Claims, 2 Drawing Sheets

(56) References Cited

OTHER PUBLICATIONS

Koch et al., "Successful therapy of tardive dyskinesia in a 71-year-old woman with a combination of tetrabenazine, olanzapine and tiapride," International Journal of Clinical Practice, 2003, 57(2):147-149.

Kung et al., "In vivo imaging of vesicular monoamine transporter 2 in pancreas using an 18F epoxide derivative of tetrabenazine," Nuclear Medicine and Biology, Nov. 1, 2008, vol. 35:825-837.

Login et al., "Tetrabenazine has properties of a dopamine receptor antagonist.," Ann. Neurology, Sep. 1982, 12(3):257-262.

Near, "[3H]Dihydrotetrabenazine binding to bovine striatal synaptic vesicles," Mol. Pharmacol., Sep. 1986, 30(3):252-257.

Obach et al, "The prediction of human pharmacokinetic parameters from preclinical and in vitro metabolism data," J. Pharmcol. Exp. Ther., Oct. 1997, 283(1):46-58.

Pettibone et al., "Tetrabenazine-induced depletion of brain monoamines: mechanism by which desmethylimipramine protects cortical norepinephrine," Eur J Pharmacol., Jul. 1984, 102:431-436.

Reches et al., "Tetrabenazine, an amine-depleting drug, also blocks dopamine receptors in rat brain," J Pharmacol Exp Ther., Jun. 1983, 225:515-521.

Remington et al., "Tetrabenazine augmentation in treatment-resistant schizophrenia: a 12-week, double-blind, placebo-controlled trial," Journal of clinical Psychopharmacology, 2012, 32(1):95-99.

Scherman et al., "Characterization of the monoamine carrier of chromaffin granule membrane by binding of [2-3H]dihydrotetrabenazine.," Proc Natl Acad Sci USA, Jan. 1983, 80(2):584-588.

Teng et al., "Lobeline displaces [3H]dihydrotetrabenazine binding and releases [3H]dopamine from rat striatal synaptic vesicles: comparison with d-amphetamine," J. Neurochem., Jul. 1998, 71(1):258-265.

Wadenberg et al., "The conditioned avoidance response test re-evaluated: is it a sensitive test for the detection of potentially atypical antipsychotics?," Biobehav. Rev., 1999, 23(6):851-862.

Williams et al., "Drug-drug interactions for UDP-glucuronosyltransferase substrates: a pharmacokinetic explanation for typically observed low exposure (AUCi/AUC) ratios," Drug Metab Dispos, Nov. 2004, 32(11):1201-1208.

Yoshifuju et al., "Absolute configuration of ankorine: Chemical correlation with cinchona alkaloids," Tetrahedron Letters, 1975, 24:1965-1968.

Russian Office Action in Russian Appln. No. 2017130514, dated Aug. 27, 2019, 18 pages (with English translation).

[9,10-DIMETHOXY-3-(2-METHYLPROPYL)-1H,2H,3H,4H,6H,7H,11BH-PYRIDO-[2,1-A]ISOQUINOLIN-2-YL]METHANOL AND COMPOUNDS, COMPOSITIONS AND METHODS RELATING THERETO

BACKGROUND

Technical Field

This disclosure relates generally to [9,10-dimethoxy-3-(2-methylpropyl)-1H,2H,3H,4H,6H,7H,11bH-pyrido[2,1-a]isoquinolin-2-yl]methanol and compounds, compositions and methods related thereto.

Description of the Related Art

Dysregulation of dopaminergic systems is integral to several central nervous system (CNS) disorders, including hyperkinetic movement disorders and conditions such as schizophrenia and bipolar disease. The transporter protein vesicular monoamine transporter-2 (VMAT2) plays an important role in presynaptic dopamine release and regulates monoamine uptake from the cytoplasm to the synaptic vesicle for storage and release.

3-Isobutyl-9,10-dimethoxy-1,3,4,6,7,11b-hexahydro-2H-pyrido[2,1-a]-isoquinolin-2-one, also known as tetrabenazine (TBZ), has been used as a drug for decades. Tetrabenazine is a potent, reversible inhibitor of catecholamine uptake by vesicular monoamine transporter-2 (VMAT2) ($IC_{50}$=3.2 nM) (see, e.g., Scherman et al., *Proc. Natl. Acad. Sci. USA*, (1983) 80:584-8) and is currently used in the treatment of various hyperkinetic disorders. Side effects associated with TBZ include sedation, depression, akathisia and parkinsonism. Inhibition of VMAT2 by TBZ results in depletion of brain monoamines in vivo (see, e.g., Pettibone et al., *Eur. J. Pharmacol.* (1984) 102:431-6). TBZ also inhibits presynaptic and postsynaptic dopamine receptors in rat brain (see, e.g., Login et al., (1982) *Ann. Neurology* 12:257-62; Reches et al., *J. Pharmacol. Exp. Ther.* (1983) 225:515-521). This off-target activity of TBZ may be responsible for some of the observed side effects.

TBZ, which contains two chiral centers and is a racemic mix of two stereoisomers, is rapidly and extensively metabolized in vivo to its reduced form, 3-isobutyl-9,10-dimethoxy-1,3,4,6,7,11b-hexahydro-2H-pyrido[2,1-a]isoquinolin-2-ol, also known as dihydrotetrabenazine (HTBZ). HTBZ is thought to exist as four individual isomers: namely, (±) alpha-HTBZ and (±) beta-HTBZ. The 2R, 3R, 11bR or (+) alpha-HTBZ is believed to be the absolute configuration of the active metabolite (see, e.g., Kilbourn et al., *Chirality* (1997), 9:59-62). Despite its success in treating hyperkinetic disorders, tetrabenazine has a fairly low and variable bioavailability. Tetrabenazine administration to humans is complicated by extensive first pass metabolism and little or no tetrabenazine is observed in the urine.

Despite the advances that have been made in this field, a need remains in the art for improved VMAT2 inhibitors, including compounds, compositions and methods related thereto. The present disclosure fulfills these and other needs, as evident in reference to the following disclosure.

BRIEF SUMMARY

In brief, provided herein is the compound [9,10-dimethoxy-3-(2-methylpropyl)-1H,2H,3H,4H,6H,7H,11bH-pyrido[2,1-a]isoquinolin-2-yl]methanol ($R^1$ =H) and related analogs or prodrugs thereof, such compounds having structure (I):

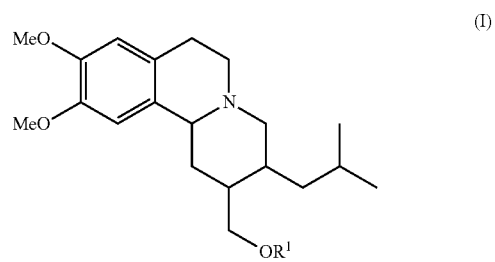

(I)

as well as stereoisomers and pharmaceutically acceptable salts or solvates thereof, wherein $R^1$ is as defined in more detail below.

In one embodiment, the compound is [(2R,3S,11bR)-9,10-dimethoxy-3-(2-methylpropyl)-1H,2H,3H,4H,6H,7H,11bH-pyrido[2,1-a]isoquinolin-2-yl]methanol, or a pharmaceutically acceptable salt or solvate thereof. In a more specific embodiment, the compound is the hydrochloride salt; namely, [(2R,3S,11bR)-9,10-dimethoxy-3-(2-methylpropyl)-1H,2H,3H,4H,6H,7H,11bH-pyrido[2,1-a]isoquinolin-2-yl]methanol HCl.

In one embodiment, a pharmaceutical composition is provided that comprises one or more compounds of structure (I) in combination with a pharmaceutically acceptable excipient and/or diluent.

In one embodiment, methods are provided for treating diseases, disorders, or conditions that benefit from inhibiting vesicular monoamine transporter 2 (VMAT2), including the family of hyperkinetic movement disorders. Accordingly, in one embodiment, methods are provided for treating a hyperkinetic disorder comprising administering to a subject in need thereof a pharmaceutically effective amount of a compound of structure (I), or a pharmaceutical composition comprising the same. In a more specific embodiment, the hyperkinetic disorder is Huntington's disease, tardive dyskinesia, Tourette's syndrome or tics.

These and other aspects of the invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION

Figure 1:
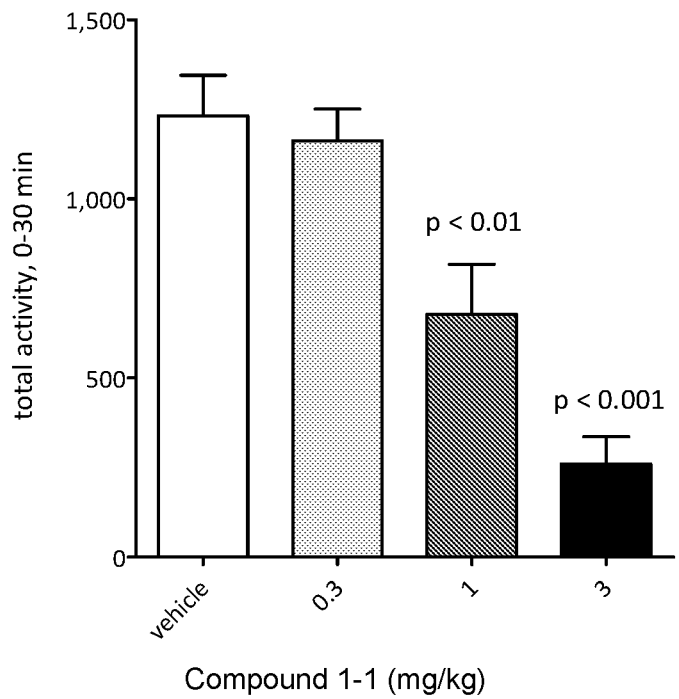
FIG. 1 illustrates the effect of representative compound (Compound 1-1) on dopamine depletion as measured using the locomotor activity (LMA) assay.

Terms not specifically defined herein should be given the meanings that would be given to them by one of skill in the art in light of the disclosure and the context. As used in the specification, however, unless specified to the contrary, the terms have the meaning indicated.

In the following description, certain specific details are set forth in order to provide a thorough understanding of various embodiments. However, one skilled in the art will understand that the present compounds may be made and used without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising," are to be construed in an open, inclusive sense, that is, as "including, but not limited to." In addition, the term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features. Headings provided herein are for convenience only and do not interpret the scope or meaning of the claimed embodiments.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Also, as used in this specification and the appended claims, the singular forms "a," "an," and "the" include plural referents unless the content clearly dictates otherwise. Thus, for example, reference to "a non-human animal" may refer to one or more non-human animals, or a plurality of such animals, and reference to "a cell" or "the cell" includes reference to one or more cells and equivalents thereof (e.g., plurality of cells) known to those skilled in the art, and so forth. When steps of a method are described or claimed, and the steps are described as occurring in a particular order, the description of a first step occurring (or being performed) "prior to" (i.e., before) a second step has the same meaning if rewritten to state that the second step occurs (or is performed) "subsequent" to the first step. The term "about" when referring to a number or a numerical range means that the number or numerical range referred to is an approximation within experimental variability (or within statistical experimental error), and thus the number or numerical range may vary between 1% and 15% of the stated number or numerical range. It should also be noted that the term "or" is generally employed in its sense including "and/or" unless the content clearly dictates otherwise. The term, "at least one," for example, when referring to at least one compound or to at least one composition, has the same meaning and understanding as the term, "one or more."

In one embodiment, provided herein is [9,10-dimethoxy-3-(2-methylpropyl)-1H,2H,3H,4H,6H,7H,11bH-pyrido[2,1-a]isoquinolin-2-yl]methanol ($R_1$=H), as well as analogs or prodrugs thereof, such compounds having structure (I):

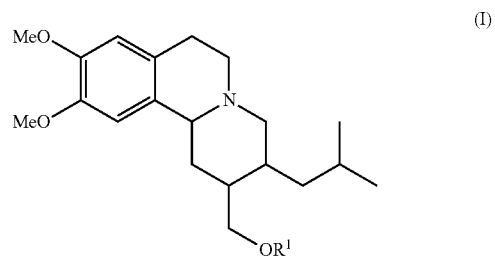

or a stereoisomer or pharmaceutically acceptable salt or solvate thereof,
wherein:
$R^1$ is a) hydrogen;
b) —P(=O)(OR$^3$)$_2$;
c) —C(=O)alkyl, wherein alkyl is optionally substituted with $R^{10}$ and/or $R^{20}$;
d) —C(=O)heterocyclyl, wherein heterocyclyl is optionally substituted with $R^{10}$ and/or $R^{20}$;
e) —C(=O)carbocyclyl, wherein carbocyclyl is optionally substituted with $R^{10}$ and/or $R^{20}$;
f) —C(=O)N(R$_3$)alkyl, wherein alkyl is optionally substituted with $R^{10}$ and/or $R^{20}$;
g) —C(=O)N(R$_3$)carbocyclyl, wherein carbocyclyl is optionally substituted with $R^{10}$ and/or $R^{20}$;
h) —C(=O)Oalkyl, wherein alkyl is optionally substituted with $R^{10}$ and/or $R^{20}$; or
i) alkyl, wherein alkyl is optionally substituted with $R^{10}$ and/or $R^{20}$;
and wherein,
each $R^3$ is independently hydrogen or alkyl;
each $R^{10}$ is independently halo, haloalkyl, cyano, nitro, trimethylsilanyl, —OR$^{30}$, —SR$^{30}$, —OC(O)—R$^{30}$, —N(R$^{30}$)$_2$, —C(O)R$^{30}$, —C(O)OR$^{30}$, —C(O)N(R$^{30}$)$_2$, —N(R$^{30}$)C(O)OR$^{31}$, —N(R$^{30}$)C(O)R$^{31}$, —N(R$^{30}$)C(=NR$^{31}$)N(R$^{12}$)$_2$, —N(R$^{30}$)S(O)$_t$R$^{31}$ (where t is 1 to 2), —S(O)$_t$OR$^{31}$ (where t is 1 to 2), —S(O)$_p$R$^{30}$ (where p is 0 to 2) or —S(O)$_t$N(R$^{30}$)$_2$ (where t is 1 to 2), —OP(=O)(OR$^{30}$)$_2$, or when a single atom bears two $R^{10}$ groups such two $R^{10}$ groups may be taken together to form oxo;
each $R^{20}$ is independently alkyl, alkenyl, aryl, aralkyl, cycloalkyl, cycloalkylalkyl, heterocyclyl, heterocyclalkyl, heteroaryl or heteroarylalkyl, or when a single atom bears two $R^{20}$ groups such two $R^{20}$ groups may be taken together to form cycloalkyl, wherein each of said alkyl, alkenyl, aryl, aralkyl, cycloalkyl, cycloalkylalkyl, heterocyclyl, heterocyclalkyl, heteroaryl and heteroarylalkyl groups is optionally substituted with $R^{10}$ and/or $R^{22}$;
each $R^{22}$ is independently alkyl, alkenyl, aryl, aralkyl, cycloalkyl, cycloalkylalkyl, heterocyclyl, heterocyclalkyl, heteroaryl or heteroarylalkyl, wherein each of said alkyl, alkenyl, aryl, aralkyl, cycloalkyl, cycloalkylalkyl, heterocyclyl, heterocyclalkyl, heteroaryl and heteroarylalkyl groups is optionally substituted with $R^{10}$; and
each $R^{30}$, $R^{31}$ and $R^{32}$ is independently hydrogen or alkyl.

With regard to stereoisomers, the compounds of structure (I) have multiple chiral (or asymmetric) centers which give rise to enantiomers, diastereomers, and other stereoisomeric forms that may be defined, in terms of absolute stereochemistry, as (R)- or (S)-. When the compounds described herein contain olefinic double bonds or other centers of geometric asymmetry, and unless specified otherwise, it is intended that the compounds include both E and Z geometric isomers (e.g., cis or trans). Likewise, unless otherwise indicated, all possible isomers, as well as their racemic and optically pure forms, and all tautomeric forms are also intended to be included. It is therefore contemplated that various stereoisomers and mixtures thereof include "enantiomers," which refers to two stereoisomers whose molecules are nonsuperimposeable mirror images of one another. Thus, the compounds may occur in any isomeric form, including racemates, racemic mixtures, and as individual enantiomers or diastereomers.

Accordingly, and in a more specific embodiment, provided herein is the compound [(2R,3S,11bR)-9,10-dimethoxy-3-(2-methylpropyl)-1H,2H,3H,4H,6H,7H,11bH-pyrido[2,1-a]isoquinolin-2-yl]methanol ($R^1$=H), as well as analogs or prodrugs thereof, having the stereochemistry noted in structure (II):

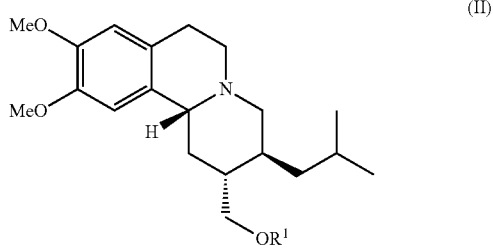

(II)

or pharmaceutically acceptable salt or solvate thereof, wherein $R_1$ is as defined above.

As used in the specification and appended claims, unless specified to the contrary, the following terms have the meaning indicated.

"Alkyl" refers to a straight or branched hydrocarbon chain radical consisting solely of carbon and hydrogen atoms, containing no unsaturation, having from one to twelve carbon atoms, one to eight carbon atoms, or one to six carbon atoms, or one to four carbon atoms, and which is attached to the rest of the molecule by a single bond, e.g., methyl, ethyl, n-propyl, 1-methylethyl (iso-propyl), n-butyl, n-pentyl, 1,1-dimethylethyl (1-butyl), 3-methylhexyl, 2-methylhexyl, and the like.

"Alkenyl" refers to a straight or branched hydrocarbon chain radical group consisting solely of carbon and hydrogen atoms, containing at least one double bond, having from two to twelve carbon atoms, preferably two to eight carbon atoms and which is attached to the rest of the molecule by a single bond, e.g., ethenyl, prop-1-enyl, but-1-enyl, pent-1-enyl, penta-1,4-dienyl, and the like.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms or from one to four carbon atoms, e.g., methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon or any two carbons within the chain.

"Carbocyclyl" refers to a stable 3- to 18-membered aromatic or non-aromatic ring radical which consists of 3 to 18 carbon atoms. Unless stated otherwise specifically in the specification, the carbocyclyl radical may be a monocyclic, bicyclic, tricyclic or tetracyclic ring system, which may include fused or bridged ring systems, and may be partially or fully saturated. Non-aromatic carbocyclyl radicals include cycloalkyl, while aromatic carbocyclyl radicals include aryl.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptly, and cyclooctyl. Polycyclic radicals include, for example, adamantyl, norbornyl, decalinyl, 7,7-dimethyl-bicyclo-[2.2.1]heptanyl, and the like.

"Aryl" refers to a hydrocarbon ring system radical comprising hydrogen, 6 to 18 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In one embodiment, aryl is phenyl or naphthyl, and in another embodiment is phenyl.

"Aralkyl" refers to a radical of the formula —$R_bR_c$ where $R_b$ is an alkylene chain as defined herein and $R_c$ is one or more aryl radicals as defined herein, for example, benzyl, diphenylmethyl and the like.

"Heterocyclyl" refers to a stable 3- to 18-membered aromatic or non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of aromatic heterocyclyl radicals are listed below in the definition of heteroaryls (i.e., heteroaryl being a subset of heterocyclyl). Examples of non-aromatic heterocyclyl radicals include, but are not limited to, dioxolanyl, thienyl [1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, pyrazolopyrimidinyl, quinuclidinyl, thiazolidinyl, tetrahydrofuryl, trioxanyl, trithianyl, triazinanyl, tetrahydropyranyl, thiomorpholinyl, thiamorpholinyl, 1-oxo-thiomorpholinyl, and 1,1-dioxo-thiomorpholinyl.

"Heterocyclylalkyl" refers to a radical of the formula —$R_bR_h$ where $R_b$ is an alkylene chain as defined herein and $R_h$ is a heterocyclyl radical as defined herein, and if the heterocyclyl is a nitrogen-containing heterocyclyl, the heterocyclyl may be attached to the alkyl radical at the nitrogen atom.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-d]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e. thienyl).

"Heteroarylalkyl" refers to a radical of the formula —$R_b R_i$ where $R_b$ is an alkylene chain as defined herein and $R_i$ is a heteroaryl radical as defined herein.

"Cyano" refers to the —CN radical.

"Halo" refers to bromo, chloro, fluoro or iodo.

"Haloalkyl" refers to an alkyl radical, as defined herein, that is substituted by one or more halo radicals, as defined herein, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like.

"Nitro" refers to the —$NO_2$ radical.

"Oxo" refers to the =O substituent.

"Trimethylsilanyl" refers to the —$Osi(CH_3)_3$ radical.

"Cycloalkylalkyl" refers to a radical of the formula —$R_b R_g$ where $R_b$ is an alkylene chain as defined herein and $R_g$ is a cycloalkyl radical as defined herein.

"Fused" refers to any ring system described herein which is fused to an existing ring structure in the compounds of the invention. When the fused ring system is a heterocyclyl or a heteroaryl, any carbon in the existing ring structure which becomes part of the fused ring system may be replaced with a nitrogen.

"Prodrug" is meant to indicate a compound that may be converted under physiological conditions or by solvolysis to a biologically active compound, such as compound 1-1 described herein. Thus, the term "prodrug" refers to a metabolic precursor of a compound described herein that is pharmaceutically acceptable. A prodrug may be inactive when administered to a subject in need thereof, but is converted in vivo to an active compound as described herein. Prodrugs are typically rapidly transformed in vivo to yield the parent compound described herein, for example, by hydrolysis in blood. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

In one embodiment, the compounds described herein serve as a prodrug to [9,10-dimethoxy-3-(2-methylpropyl)-1H,2H,3H,4H,6H,7H,11bH-pyrido[2,1-a]-isoquinolin-2-yl] methanol (compound 1-1); that is, the compound may be converted under physiological conditions to compound 1-1. In another embodiment, the compounds described herein are themselves VMAT2 inhibitors, and thus active analogs to compound 1-1.

The compounds described herein may exist in a continuum of solid states ranging from fully amorphous to fully crystalline. Furthermore, some of the crystalline forms of the compounds having a structure of formula (I), formula II, and substructures and specific compounds thereof, may exist as polymorphs. In addition, some of the compounds may also form solvates with water or other organic solvents. The term solvate is used herein to describe a molecular complex comprising a compound described herein and one or more pharmaceutically acceptable solvent molecules. Such solvates are similarly included within the scope of this disclosure.

As one of skill in the art would appreciate, any of the compounds described herein may incorporate radioactive isotopes. Accordingly, also contemplated is use of isotopically-labeled compounds identical to those described herein, wherein one or more atoms are replaced by an atom having an atomic mass or mass number different from the atomic mass or mass number usually found in nature. Examples of isotopes that can be incorporated into these compounds include isotopes of hydrogen, carbon, nitrogen, oxygen, phosphorous, fluorine and chlorine, such as, but not limited to, $^2H$, $^3H$, $^{13}C$, $^{14}C$, $^{15}N$, $^{18}O$, $^{17}O$, $^{31}P$, $^{32}P$, $^3S$, $^8F$, and $^{36}Cl$, respectively. Certain isotopically-labeled compounds, for example those into which radioactive isotopes such as $^3H$ and $^{14}C$ are incorporated, are also useful in drug or substrate tissue distribution assays. Tritiated hydrogen ($^3H$) and carbon-14 ($^{14}C$) isotopes are particularly preferred for their ease of preparation and detectability. Substitution with heavier isotopes such as deuterium (2H) can provide certain therapeutic advantages resulting from greater metabolic stability, for example increased in vivo half-life or reduced dose requirements and, therefore, may be preferred in some circumstances.

Isotopically-labeled compounds can generally be prepared by performing procedures routinely practiced in the art.

In one embodiment, $R^1$ of structures (I) and (II) is hydrogen, and the compound has structure (III) or (IV):

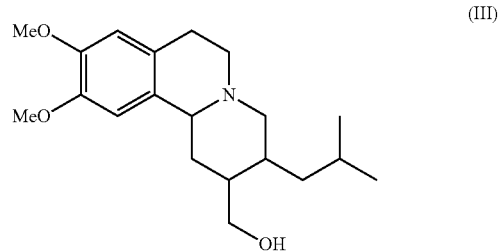

(III)

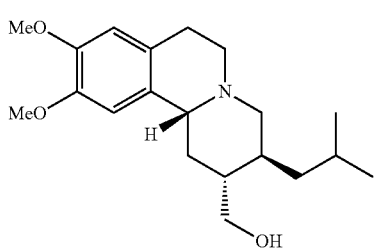
(IV)

In one embodiment, $R^1$ of structure (I) and (II) is —C(=O)—$R^2$, where $R^2$ is alkyl, heterocyclyl or carbocyclyl and each of said alkyl, heterocyclyl or carbocyclyl is optionally substituted with $R^{10}$ and/or $R^{20}$ as defined above, and the compound has structure (V) or (VI):

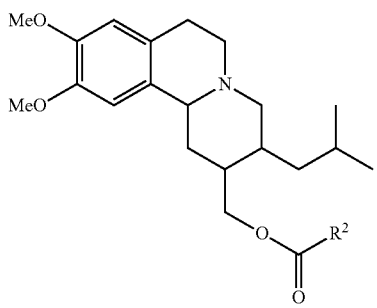
(IV)

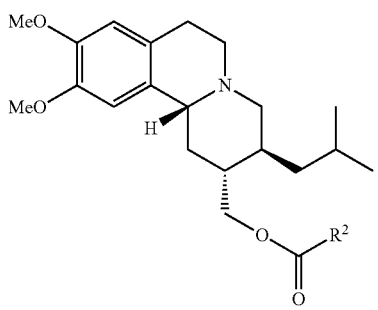
(VI)

In an embodiment, $R_1$ of structure (I) and (II) is —C(=O)—O—$R^2$, where $R^2$ is alkyl and said alkyl is optionally substituted with $R^{10}$ and/or $R^{20}$ as defined above, and the compound has structure (VI) or (VII):

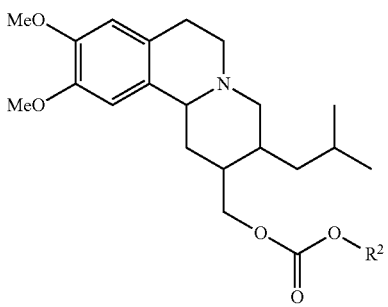
(VI)

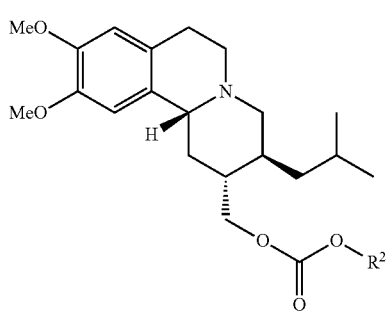
(VII)

In an embodiment, $R^1$ of structure (I) and (II) is —C(=O)N($R^3$)$R^2$ where $R^2$ is alkyl, heterocyclyl or carbocyclyl and each of said alkyl, heterocyclyl or carbocyclyl is optionally substituted with $R^{10}$ and/or $R^{20}$ as defined above, and the compound has structure (VIII) or (IX):

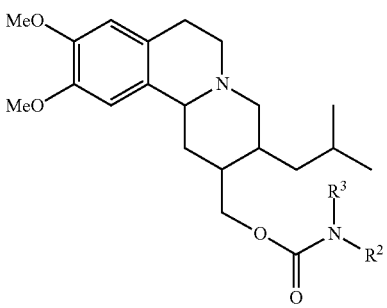
(VIII)

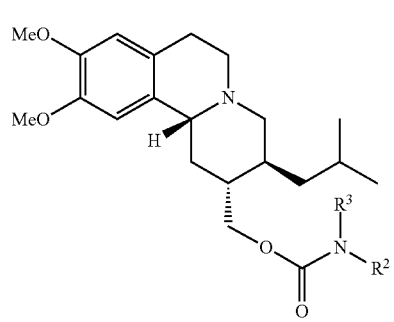
(IX)

In an embodiment, $R^1$ of structure (I) and (II) is alkyl, wherein said alkyl is optionally substituted with $R^{10}$ and/or $R^{20}$ as defined above, and the compound has structure (X) or (XI):

(X)

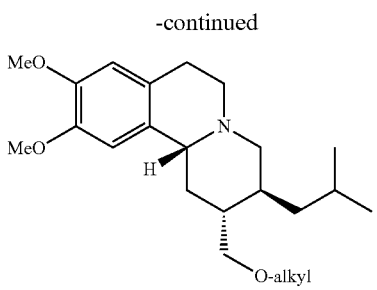

In an embodiment, $R^1$ of structure (I) and (II) is —P(=O)(OR$^3$)$_2$, and the compound has the structure of formula (XII) or (XIII):

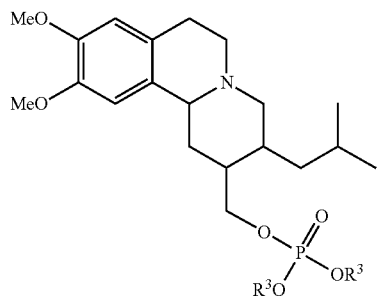

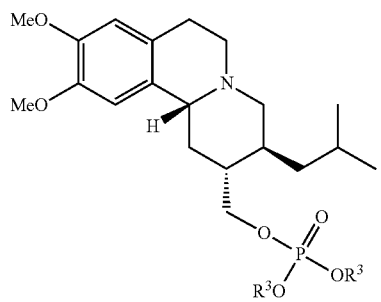

In certain embodiments of compounds having structures (I) through (XIII), wherein the alkyl, heterocyclyl or carbocyclyl of such structures is optionally substituted with $R^{10}$ and/or $R^{20}$. Optional substitution in this regard means that the alkyl, heterocyclyl or carbocyclyl group is either (i) not substituted with $R^{10}$ or $R^{20}$, or (ii) is substituted with one or both of $R^{10}$ and $R^{20}$. When substituted with one or both of $R^{10}$ and $R^{20}$, such substituents may be present singularly (i.e., a single $R^{10}$ or $R^{20}$ substituent), or in multiples (i.e., more than one $R^{10}$ substituent, more than one $R^{20}$ substituent, or a combination of one or more $R^{10}$ substituents, and one or more $R^{20}$ substituents). The total number of $R^{10}$ and/or $R^{20}$ substituents may range from zero (i.e., when the alkyl, heterocyclyl or carbocyclyl is unsubstituted) up to 10 (i.e., when the alkyl, heterocyclyl or carbocyclyl is substituted). When substituted the total number of $R^{10}$ and $R^{20}$ substituents generally range from 1 to 10, or from 1 to 8, or from 1 to 6, or from 1 to 4, or from 1 to 2. In those embodiments in which the alkyl, heterocyclyl or carbocyclyl is substituted with $R^{20}$, such $R^{20}$ substituent may be optionally substituted with $R^{10}$ and/or $R^{22}$ as defined above in the context of $R^{10}$ and/or $R^{20}$. Further, in the case of $R^{22}$, such $R^{22}$ substituent may be optionally substituted with $R^{10}$, again as defined in the context of $R^{10}$ above.

In one embodiment, $R^1$ is —C(=O)alkyl, wherein alkyl is optionally substituted with $R^{10}$ and/or $R^{20}$. Representative "OR$^1$" groups of this embodiment are labeled "A" in Table 1.

In one embodiment, $R^1$ is —C(=O)heterocyclyl, wherein heterocyclyl is optionally substituted with $R^{10}$ and/or $R^{20}$. Representative "OR$^1$" groups of this embodiment are labeled "B" in Table 1.

In one embodiment, $R^1$ is —C(=O)carbocyclyl, wherein carbocyclyl is optionally substituted with $R^{10}$ and/or $R^{20}$. Representative "OR$^1$" groups of this embodiment are labeled "C" in Table 1.

In one embodiment, $R^1$ is —C(=O)N(R$^3$)alkyl, wherein alkyl is optionally substituted with $R^{10}$ and/or $R^{20}$. Representative "OR$^1$" groups of this embodiment are labeled "D" in Table 1.

In one embodiment, R is —C(=O)N(R$^3$)carbocycle, wherein carbocycle is optionally substituted with $R^{10}$ and/or $R^{20}$. Representative "OR$^1$" groups of this embodiment are labeled "E" in Table 1.

In one embodiment, $R^1$ is —P(=O)(OR$^3$)$_2$ and representative "OR$^1$" groups of this embodiment are labeled "F" in Table 1.

In one embodiment, $R^1$ is —C(=O)Oalkyl, wherein alkyl is optionally substituted with $R^{10}$ and/or $R^{20}$. Representative "OR$^1$" groups of this embodiment are labeled "G" in Table 1.

In one embodiment, $R^1$ is alkyl, wherein alkyl is optionally substituted with $R^{10}$ and/or $R^{20}$. Representative "OR$^1$" groups of this embodiment are labeled "H" in Table 1.

It should be noted that some of the compounds listed in Table 1 may be characterized by more than one class. For example, compound 5-5 is identified as a "D" compound, indicating that $R^1$ is —C(=O)N(R$^3$)alkyl, wherein alkyl is optionally substituted with $R^{10}$ and/or $R^{20}$ (in this case, two $R^{20}$ groups are taken together to form cyclopropyl). However, compound 5-5 may also be classified as an "E" compound, indicating that $R^1$ is —C(=O)N(R$^3$)carbocycle, wherein carbocycle is optionally substituted with $R^{10}$ and/or $R^{20}$. Thus, the classifications below are not meant to exclude any specific compound from falling within multiple classes.

Furthermore, in Table 1 (as well as Tables 2-8 below), the monovalent oxygen ("O") denotes the point of attachment of the "OR$_1$" substituent to structure (I), and is not a component of the $R^1$ group. It should also be noted that, for purpose of abbreviation, some nitrogen atoms are depicted absent their accompanying hydrogen atoms, such as monovalent "—N" in place of "—NH$_2$" and divalent "—N—" in place of "—NH—". One skilled in this field will radially recognize and appreciate the meaning of such abbreviated designations.

TABLE 1

| Representative $R^1$ Groups | | |
|---|---|---|
| Cpd. | O—R$^1$ | |
| 2-1 | ![structure] | A |
| 2-2 | ![structure] | A |

TABLE 1-continued

Representative R¹ Groups

| Cpd. | O—R¹ | |
|------|------|---|
| 2-3 | quinazoline-2,4-dione-N-propanoate | A |
| 2-4 | N,N-dimethylsuccinamate | A |
| 2-5 | N-(ethylsulfonyl)-β-alaninate | A |
| 2-6 | (3R)-1-benzylpyrrolidine-3-carboxylate | B |
| 2-7 | 3-(dimethylamino)propanoate | A |
| 2-8 | (2S,6R)-2,6-dimethylmorpholine-4-acetate | A |
| 2-9 | malonamate | A |
| 2-10 | (1-methylpyrrolidin-3-yl)acetate | A |
| 2-11 | (3R)-1-benzylpiperidine-3-carboxylate | B |
| 2-12 | 1-methylpiperidine-3-carboxylate | B |
| 2-13 | 3-(1H-tetrazol-1-yl)propanoate | A |
| 2-14 | 3-nitropropanoate | A |
| 2-15 | 3-(4-methylpiperazin-1-yl)propanoate | A |
| 2-16 | N-(isopropylsulfonyl)-β-alaninate | A |
| 2-17 | pivalate | A |

TABLE 1-continued

Representative R¹ Groups

| Cpd. | O—R¹ | |
|---|---|---|
| 2-18 | [3-methyloxetane-3-carboxylate] | B |
| 2-19 | [3-(piperidin-1-yl)propanoate] | A |
| 2-20 | [benzoate] | C |
| 2-21 | [1-benzylazetidine-3-carboxylate] | B |
| 2-22 | [tetrahydro-2H-pyran-4-carboxylate] | B |
| 2-23 | [3-(3-methyl-1H-pyrazol-1-yl)propanoate] | A |
| 2-24 | [2-hydroxy-2-methylpropanoate] | A |
| 2-25 | [1-methylpiperidine-4-carboxylate] | B |
| 2-26 | [1-benzylpyrrolidine-3-carboxylate] | B |
| 2-27 | [2,2,5,5-tetramethyl-1-oxyl-pyrrolidine-3-carboxylate] | B |
| 2-28 | [3-methyl-3-(1H-pyrrol-1-yl)butanoate] | A |
| 2-29 | [3-(5-methyl-1H-pyrazol-1-yl)propanoate] | A |
| 2-30 | [2-(2,5-dioxoimidazolidin-4-yl)acetate] | A |
| 2-31 | [2,6-dioxohexahydropyrimidine-4-carboxylate] | B |
| 2-32 | [3-(diethylamino)propanoate] | A |

TABLE 1-continued

Representative R¹ Groups

| Cpd. | O—R¹ | |
|---|---|---|
| 2-33 | (hydantoin-CH₂-CO-O- structure) | A |
| 2-34 | (hexanoate, -O-CO-(CH₂)₄-CH₃) | A |
| 2-35 | (HO-SO₂-CH₂-CO-O-) | A |
| 2-36 | (-O-CO-(CH₂)₂-CH₂-N(CH₃)₂) | A |
| 2-37 | (N-methanesulfonyl piperidine-3-carboxylate) | B |
| 2-38 | (2,2,3,3-tetramethylcyclopropanecarboxylate) | C |
| 2-39 | (benzoxazol-2(3H)-one-N-propanoate) | A |
| 3-1 | (HO-CO-CH₂-C(CH₃)₂-CH₂-CO-O-) | A |
| 3-2 | (malonate, HO-CO-CH₂-CO-O-) | A |
| 3-3 | (3-methylglutarate) | A |
| 3-4 | (cyclopropane-1,2-dicarboxylate) | C |
| 3-5 | (cyclohexane-1,2-dicarboxylate, and1/and1) | C |
| 3-6 | (cyclohexane-1,2-dicarboxylate, trans) | C |
| 3-7 | (HO-CO-C(CH₃)₂-CH₂-CO-O-) | A |
| 3-8 | (glutarate) | A |
| 3-9 | (1,1-cyclopentanediacetate) | A |
| 3-10 | (adipate) | A |
| 3-11 | (HO-CO-CH₂-C(CH₃)₂-CO-O-) | A |

TABLE 1-continued
Representative R¹ Groups
| Cpd. | O—R¹ | |
|---|---|---|
| 3-12 | 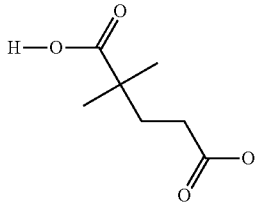 | A |
| 3-13 | 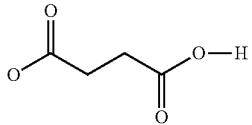 | A |
| 4-1 | 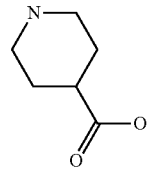 | B |
| 4-2 | 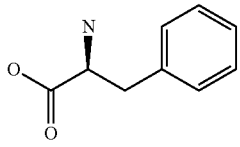 | A |
| 4-3 | 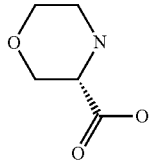 | B |
| 4-4 | 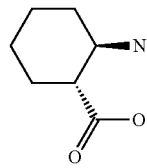 | B |
| 4-5 | 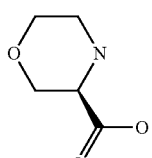 | B |
| 4-6 | 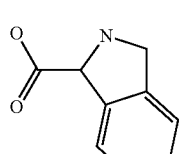 | B |
| 4-7 | 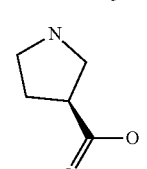 | B |
| 4-8 | 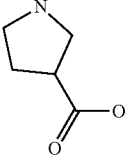 | B |
| 4-9 | 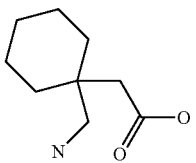 | A |
| 4-10 | 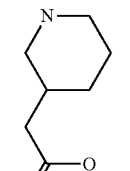 | A |
| 4-11 | 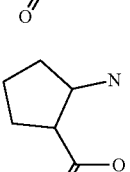 | B |
| 4-12 | 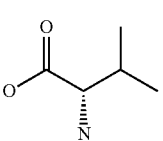 | A |
| 4-13 | 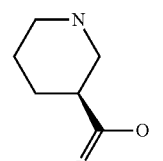 | B |
| 4-14 |  | A |
| 4-15 | 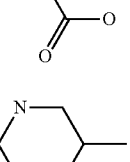 | B |

TABLE 1-continued
Representative R¹ Groups
| Cpd. | O—R¹ | |
|---|---|---|
| 4-16 | 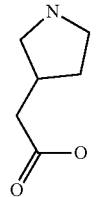 | A |
| 4-17 | 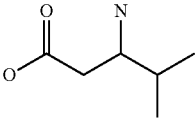 | A |
| 4-18 |  | C |
| 4-19 | 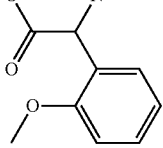 | A |
| 4-20 | 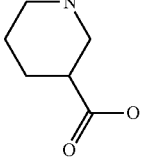 | B |
| 4-21 | 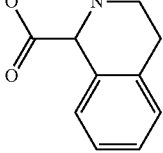 | B |
| 4-22 | 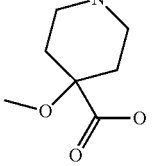 | B |
| 4-23 | 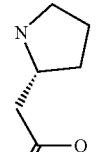 | A |
| 4-24 | 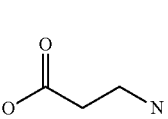 | A |
| 4-25 | 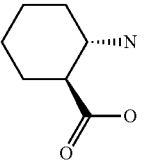 | C |
| 4-26 | 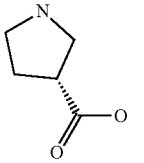 | B |
| 4-27 | 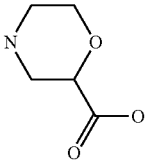 | B |
| 4-28 | 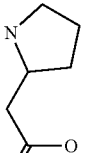 | A |
| 4-29 | 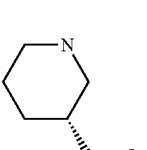 | B |
| 4-30 | 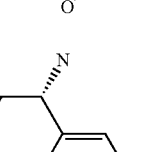 | A |
| 4-31 | 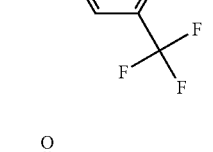 | A |
| 4-32 | 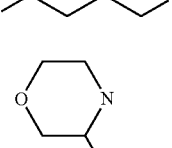 | B |

TABLE 1-continued

Representative R¹ Groups

| Cpd. | O—R¹ | |
|---|---|---|
| 4-33 | | A |
| 4-34 | | A |
| 4-35 | | B |
| 4-36 | | A |
| 4-37 | | A |
| 4-38 | | A |
| 5-1 | | D |
| 5-2 | | D |
| 5-3 | | D |
| 5-4 | | B |
| 5-5 | | D |
| 5-6 | | B |
| 5-7 | | B |
| 5-8 | | B |
| 5-9 | | E |

TABLE 1-continued

Representative R¹ Groups

| Cpd. | O—R¹ | |
|---|---|---|
| 5-10 | (structure) | D |
| 5-11 | (structure) | D |
| 5-12 | (structure) | B |
| 5-13 | (structure) | B |
| 5-14 | (structure) | B |
| 5-15 | (structure) | B |
| 5-16 | (structure) | D |
| 5-17 | (structure) | D |
| 5-18 | (structure) | B |
| 5-19 | (structure) | D |
| 5-20 | (structure) | D |
| 5-21 | (structure) | B |
| 5-22 | (structure) | D |
| 5-23 | (structure) | D |
| 5-24 | (structure) | B |
| 5-25 | (structure) | D |

TABLE 1-continued

Representative R¹ Groups

| Cpd. | O—R¹ | |
|---|---|---|
| 5-26 | (structure) | D |
| 5-27 | (structure) | B |
| 5-28 | (structure) | D |
| 5-29 | (structure) | D |
| 5-30 | (structure) | D |
| 5-31 | (structure) | B |
| 5-32 | (structure) | D |
| 5-33 | (structure) | D |
| 5-34 | (structure) | D |
| 5-35 | (structure) | E |
| 5-36 | (structure) | D |
| 5-37 | (structure) | B |
| 5-38 | (structure) | D |
| 5-39 | (structure) | D |
| 5-40 | (structure) | E |
| 5-41 | (structure) | E |

TABLE 1-continued

Representative R¹ Groups

| Cpd. | O—R¹ | |
|---|---|---|
| 5-42 | [structure] | D |
| 5-43 | [structure] | B |
| 5-44 | [structure] | B |
| 5-45 | [structure] | D |
| 5-46 | [structure] | D |
| 5-47 | [structure] | D |
| 5-48 | [structure] | B |
| 5-49 | [structure] | B |
| 5-50 | [structure] | B |
| 5-51 | [structure] | D |
| 5-52 | [structure] | B |
| 5-53 | [structure] | B |
| 5-54 | [structure] | B |
| 5-55 | [structure] | D |
| 5-56 | [structure] | D |
| 5-57 | [structure] | D |

TABLE 1-continued

Representative R¹ Groups

| Cpd. | O—R¹ | |
|---|---|---|
| 6-1 | [piperazine-N-C(=O)-O-] | B |
| 6-2 | [(2,5-dimethyl)piperazine-N-C(=O)-O-] | B |
| 6-3 | [(2-methyl)piperazine-N-C(=O)-O-] | B |
| 6-4 | [3,8-diazabicyclo[3.2.1]octane-N-C(=O)-O-] | B |
| 6-5 | [(2-methyl)piperazine-N-C(=O)-O-] | B |
| 6-6 | [(3,5-dimethyl)piperazine-N-C(=O)-O-] | B |
| 6-7 | [(2-hydroxymethyl)piperazine-N-C(=O)-O-] | B |
| 6-8 | [(2-carboxy)piperazine-N-C(=O)-O-] | B |
| 6-9 | [(2-cyano)piperazine-N-C(=O)-O-] | B |
| 6-10 | [3,6-diazabicyclo[3.1.1] ring-N-C(=O)-O-] | B |
| 6-11 | [(3,5-dimethyl)piperazine-N-C(=O)-O-] | B |
| 6-12 | [(2,3-dimethyl)piperazine-N-C(=O)-O-] | B |
| 6-13 | [(2-methyl)piperazine-N-C(=O)-O-] | B |
| 6-14 | [(2,5-dimethyl)piperazine-N-C(=O)-O-] | B |

TABLE 1-continued

Representative R¹ Groups

| Cpd. | O—R¹ | |
|---|---|---|
| 7-1 | (diethyl phosphate) | F |
| 8-1 | (isopropyl carbonate) | G |
| 9-1 | (methoxy) | H |
| 9-2 | (2-fluoroethoxy) | H |
| 9-3 | (2-(4-fluorophenyl)-2-oxoethoxy) | H |
| 9-4 | (CD₃-O, trideuteromethoxy) | H |
| 9-5 | (methoxymethoxy) | H |
| 9-6 | (2,2,2-trifluoroethoxy) | H |
| 9-7 | (3,3,3-trifluoropropoxy) | H |
| 9-8 | (ethoxy) | H |
| 9-9 | (isobutoxy) | H |
| 10-1 | (2-(piperidin-4-yl)ethoxy) | H |
| 10-2 | ((pyrrolidin-3-yl)methoxy) | H |
| 10-3 | (pentyloxy) | H |
| 10-4 | ((pyrrolidin-2-yl)methoxy) | H |
| 10-5 | ((piperidin-4-yl)methoxy) | H |
| 10-6 | ((pyrrolidin-3-yl)methoxy) | H |
| 10-7 | ((pyrrolidin-2-yl)methoxy) | H |

The compounds described herein may be prepared by known organic synthesis techniques, including the methods described in the Schemes hereafter and in more detail in the Examples.

Reaction Scheme 1

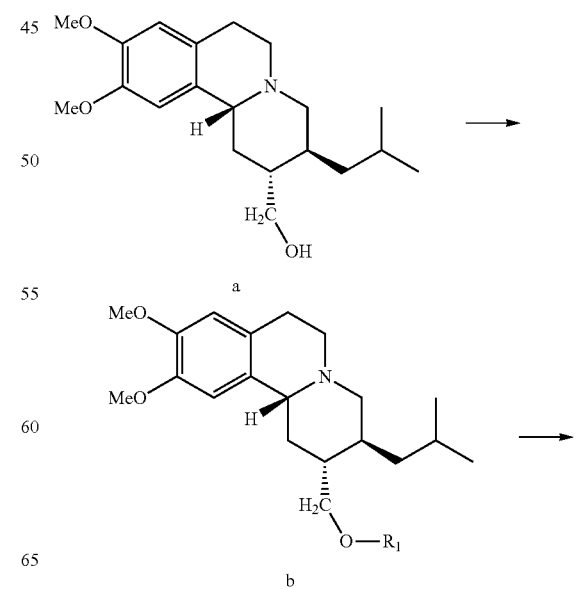

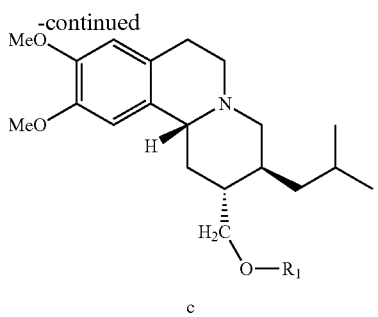

c

Alcohol a is condensed with an acid using 1-(3-dimethylaminopropyl)-3-ethylcarbodiimide hydrochloride (EDCI) and dimethylaminopyridine (DMAP) in methylene chloride to give ester c. Alternatively, ester c can be generated by treating alcohol a with an acid chloride.

The chloroformate intermediate b may be generated by treating alcohol a with phosgene or triphosgene. Treatment of b with an alcohol in the presence of a base such as DMAP generates the carbonate product c. Alternatively, the carbonate c can be generated directly by treating the alcohol a with a pyrocarbonate under DMAP catalysis.

The carbamate c may be generated by treating alcohol a with a carbamoyl chloride in methylene chloride in the presence of a base.

Phosphonate c is generated by treating alcohol a with a chlorophosphonate and pyridine in methylene chloride. The phosphonic acid c may be generated by removal of the benzyl groups from the phosphonate with palladium on carbon under an atmosphere of hydrogen. Alternatively, the phosphonic acid c can be generated directly with $POCl_3$ in water.

Reaction Scheme 2

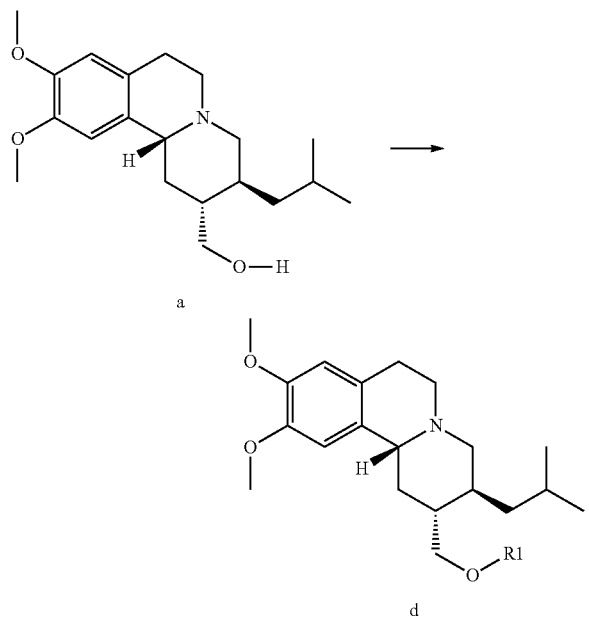

Alcohol a is condensed with a BOC protected amino acid using 1-(3-dimethylaminopropyl)-3-ethylcarbodiimide hydrochloride (EDCI) and dimethylaminopyridine (DMAP) in dimethylformamide and methylene chloride, followed by deprotection of the BOC functionality with, for instance, a 50/50 trifluoroacetic acid/methylene chloride solution to give d. Alternatively, alcohol a may be condensed with a CBZ-protected amino acid using DCC (1,3-dicyclohexylcarbodiimide) followed by deprotection of the CBZ functionality by hydrogenation under appropriate conditions.

The compounds described herein may generally be utilized as the free acid or free base. Alternatively, the compounds may be used in the form of acid or base addition salts. Acid addition salts of the free amino compounds may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, a "pharmaceutically acceptable salt" is intended to encompass any and all acceptable salt forms.

In general, the compounds used in the reactions described herein may be made according to organic synthesis techniques known to those skilled in this art, starting from commercially available chemicals and/or from compounds described in the chemical literature. "Commercially available chemicals" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hanover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

Methods known to one of ordinary skill in the art may be identified through various reference books and databases. Suitable reference books and treatise that detail the synthesis of reactants useful in the preparation of compounds of the present disclosure, or provide references to articles that describe the preparation, include for example, "Synthetic Organic Chemistry," John Wiley & Sons, Inc., New York; S. R. Sandler et al., "Organic Functional Group Preparations," 2nd Ed., Academic Press, New York, 1983; H. O. House, "Modem Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure," 4th Ed., Wiley-Interscience, New York, 1992. Additional suitable reference books and treatise that detail the synthesis of reactants useful in the preparation of compounds of the present disclosure, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modem Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Quin, L. D. et al. "A Guide to Organophosphorus Chemistry" (2000) Wiley-Interscience, ISBN: 0-471-31824-8; Solomons, T. W. G. "Organic Chemistry" 7th Edition (2000) John Wiley & Sons, ISBN: 0-471-19095-0; Stowell, J.C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the present disclosure is P. H. Stahl & C. G. Wermuth "Handbook of Pharmaceutical Salts," *Verlag Helvetica Chimica Acta*, Zurich, 2002.

As mentioned above, the compounds described herein and their salts may reduce the supply of monoamines in the central nervous system by inhibiting the human monoamine transporter isoform 2 (VMAT2). As such, these compounds and their salts may have utility over a wide range of therapeutic applications, and may be used to treat a variety of disorders which are caused by or linked to inhibition of the human monoamine transporter isoform 2. These disorders include hyperkinetic disorders, schizophrenia and bipolar disease.

In an embodiment, conditions which may be treated by compounds described herein include, but are not limited to, treatment of hyperkinetic disorders such as Huntington's disease, tardive dyskinesia, Tourette's syndrome, and tics.

In another embodiment, the compounds described herein and their salts may be hydrolyzed in the body of a mammal to compounds that may inhibit the human monoamine transporter isoform 2. As such, these compounds and their salts may have additional utility in altering the in vivo properties of the metabolite in a mammal such as the maximum concentration or duration of action.

The compounds described herein, such as [(2R,3S,11bR)-9,10-dimethoxy-3-(2-methylpropyl)-1H,2H,3H,4H,6H,7H,11bH-pyrido[2,1-a]isoquinolin-2-yl]methanol (also called Compound 1-1 herein) may be less likely to exhibit pharmacokinetic variability. This reduced variability may be due to a reduced interaction with the CYP2D6 related metabolic pathway. Without wishing to be bound by theory, such compounds may thus possess less potential for drug-drug interaction (DDI) associated with a CYP2D6 mechanism.

In another embodiment, pharmaceutical compositions containing one or more monoamine re-uptake inhibitors (i.e., VMAT2 inhibitors) are disclosed. For the purposes of administration, the compounds described herein may be formulated as pharmaceutical compositions. Pharmaceutical compositions comprise a monoamine re-uptake inhibitor described herein and a pharmaceutically acceptable excipient, carrier and/or diluent. The VMAT2 inhibitor is present in the composition in an amount that is effective to treat a particular disorder—that is, in an amount sufficient to reduce the supply of monoamines in the central nervous system, and preferably with acceptable toxicity to the patient. Appropriate concentrations and dosages can be readily determined by one skilled in the art.

As understood by a person skilled in the medical art, the terms, "treat" and "treatment," refer to medical management of a disease, disorder, or condition of a subject (i.e., patient) (see, e.g., Stedman's Medical Dictionary). The terms "treatment" and "treating" embraces both preventative, i.e. prophylactic, or therapeutic, i.e. curative and/or palliative, treatment. Thus the terms "treatment" and "treating" comprise therapeutic treatment of patients having already developed the condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods described herein may be used, for instance, as therapeutic treatment over a period of time as well as for chronic therapy. In addition the terms "treatment" and "treating" comprise prophylactic treatment, i.e., a treatment of patients at risk to develop a condition mentioned hereinbefore, thus reducing the risk.

The subject in need of the compositions and methods described herein includes a subject who has been diagnosed by a person skilled in the medical and psychiatric arts with a hyperkinetic disorder (e.g., tardive dyskinesia). A subject (or patient) to be treated may be a mammal, including a human or non-human primate. The mammal may be a domesticated animal such as a cat or a dog.

Therapeutic and/or prophylactic benefit includes, for example, an improved clinical outcome, both therapeutic treatment and prophylactic or preventative measures, wherein the object is to prevent or slow or retard (lessen) an undesired physiological change or disorder, or to prevent or slow or retard (lessen) the expansion or severity of such disorder. Prophylactic administration of a composition herein may commence upon first treatment with dopamine receptor blocking drugs such as neuroleptics. As discussed herein, beneficial or desired clinical results from treating a subject include, but are not limited to, abatement, lessening, or alleviation of symptoms that result from or are associated the disease, condition, or disorder to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; and/or overall survival. "Treatment" can also mean prolonging survival when compared to expected survival if a subject were not receiving treatment. Subjects in need of treatment include those who already have the condition or disorder as well as subjects prone to have or at risk of developing the disease, condition, or disorder (e.g., TD or other conditions or disorders described herein), and those in which the disease, condition, or disorder is to be prevented (i.e., decreasing the likelihood of occurrence of the disease, disorder, or condition). A therapeutically effective amount of any one of the compounds described herein in the amount of the compound that provides a statistically or clinically significant therapeutic and/or prophylactic benefit to the treated subject.

Methods for determining the effectiveness of a therapeutic for treating a hyperkinetic disorder are routinely practiced in the art by a person skilled in the medical and clinical arts. By way of example, a subject with a hyperkinetic disorder may be diagnosed, monitored, and evaluated by the Abnormal Involuntary Movement Scale (AIMS). The AIMS is a structured neurological examination that was developed in 1976 and has been used extensively in movement disorder assessments. It consists of seven distinct ratings of regional involuntary body movements that are scored on a zero to four scale with zero being rated as none and four being rated as severe.

Characterizing any of the compounds having a structure of formula (I), (II), including any substructures and specific compounds thereof, may be determined using methods described herein and in the art. For example, dopamine depletion may be determined using the locomotor activity (LMA) assay. Another in vivo animal model includes the conditioned avoidance response (CAR) test, which has been shown to be an effective and reliable preclinical model for assessing the antipsychotic activity of compounds.

The present disclosure further provides for pharmaceutical compositions comprising any one of the compounds described herein (a compound of Formula I, Formula II, and including all substructures and specific compounds described herein) and a pharmaceutically acceptable excipient for use in the methods for treating neurological disorders and diseases, such as hyperkinetic disorders.

Pharmaceutically acceptable carriers and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a VMAT2 inhibitor, diluents, dispersing and surface active agents, binders, and lubricants. One skilled in this art may further formulate the VMAT2 inhibitor in an appropriate manner, and in accordance with accepted practices, such as those disclosed in Remington's Pharmaceutical Sciences, Gennaro, Ed., Mack Publishing Co., Easton, Pa. 1990.

The pharmaceutical compositions provided herein may be formulated as immediate or modified release dosage forms, including delayed-, sustained-, pulsed-, controlled, targeted-, and programmed-release forms. The pharmaceutical compositions may also be formulated as a suspension, solid, semi-solid, or thixotropic liquid, for administration as an implanted depot.

In another embodiment, a method is provided herein for treating disorders of the central or peripheral nervous system. Such methods include administering a compound described herein to a warm-blooded animal (e.g., a human) in an amount sufficient to treat the condition. In this context, "treat" includes prophylactic administration. Such methods include systemic administration of a VMAT2 inhibitor described herein, preferably in the form of a pharmaceutical composition as discussed above. As used herein, systemic administration includes oral and parenteral methods of administration. For oral administration, suitable pharmaceutical compositions include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds described herein can be prepared in aqueous injection solutions which may contain, in addition to the VMAT2 inhibitor, buffers, antioxidants, bacteriostats, and other additives commonly employed in such solutions.

EXAMPLES

Analytical Method—Ultra-High Performance Liquid Chromatography (UPLC-MS)

Platform: Agilent 1260 series UPLC: equipped with an auto-sampler, an UV detector (220 nM and 254 nM), column thermostat, a MS detector (electrospray);

Column: Waters XBridge BEH C18 XP, 2.5 micron, 3×50 mm;

Mobile phase: A=water, 0.025% TFA; B=acetonitrile, 0.025% TFA;

Flow rate: 1.5 mL/min;

Gradient: 10% B/90% A to 90% B/10% A over 1.5 min, then hold 0.3 min, return to initial conditions for 0.5 min; total run time 2.5 min;

For purpose of abbreviation, some nitrogen atoms and/or oxygen atoms are depicted in the following Examples absent their accompanying hydrogen atoms, such as monovalent "—N" in place of "—NH$_2$," and "—O" in place of "—OH", and divalent "—N—" in place of "—NH—". One skilled in this field will radially recognize and appreciate the meaning of such abbreviated designations.

Example 1

Synthesis of [(2R,3S,11bR)-9,10-dimethoxy-3-(2-methylpropyl)-1H,2H,3H,4H,6H,7H,11bH-pyrido[2,1-a]isoquinolin-2-yl]methanol HCl Salt

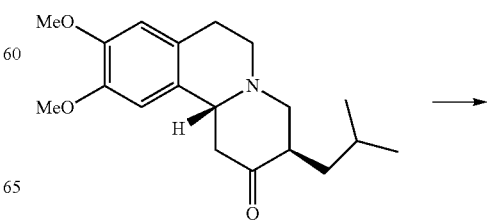

-continued

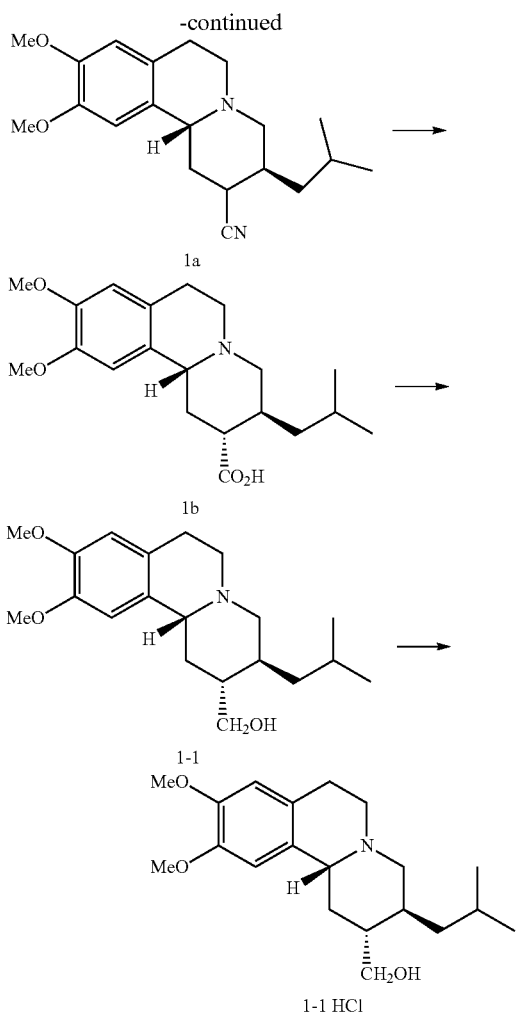

Step 1A: (3S,11bR)-9,10-Dimethoxy-3-(2-methylpropyl)-1H,2H,3H,4H,6H,7H,11bH-pyrido[2,1-a]isoquinoline-2-carbonitrile (1a)

To a 3 L 3 neck round bottomed flask DMSO (1.1 L) and TOSMIC (104 g, 532.5 mmol, 1.3 eq) were charged. To this mixture KO-t-Bu (119.5 g, 1.065 mol) was charged at once at ambient temp (22° C.). An exotherm was observed and the temperature of the mixture increased to 39° C. Then a suspension of tetrabenazine (130 g, 410 mmol) in DMSO (500 mL) was added to the reaction mixture slowly over 25 min (a slight exotherm observed). EtOH (10.5 mL) was added to this mixture and the mixture was stirred at ambient temp for 3 h. LC-MS analysis of the mixture revealed presence of ~4:1 ratio of 1a and starting material. The mixture was poured into cold water (9 L). The mixture was then extracted with EtAOc (4 L). The aqueous layer was extracted with EtOAc (2 L). The combined organics were washed with brine (2 L), dried over $Na_2SO_4$ and concentrated. The residue was dissolved in ace tone (200 ml) and loaded onto a silica column (2 Kg silica gel, packed with hexanes). The column was eluted first with hexanes (2.5 L), followed by 5-20% of acetone in hexanes. The fractions containing 1a and other impurities were combined and concentrated to give an orange oil (72 g) which was dissolved in acetone (100 ml) and loaded onto a silica column (1 Kg silica gel, packed with hexanes). The column was eluted first with hexanes (1 L), followed by 5% of acetone in hexanes (2 L), 10% of acetone in hexanes (2 L), 15% of acetone in hexanes (2 L), and 20% of acetone in hexanes (2 L). The fractions containing >90% purity were combined and concentrated to give (3S,11bR)-9,10-dimethoxy-3-(2-methylpropyl)-1H,2H,3H,4H,6H,7H,11bH-pyrido[2,1-a]isoquinoline-2-carbonitrile 1a as an orange solid (61 g, m/z 329.2 [MH$^+$]). The fractions containing a mixture of 1a and starting material were collected and concentrated to give 48 g of material which was dissolved in DMSO (50 ml) and was added to a mixture of TOSMIC (25 g) and KO-t-Bu (28.7 g) in DMSO (250 ml) as shown above. The residue was dissolved in acetone (10 ml) and loaded onto a silica column (600 g silica gel, packed with hexanes). The column was eluted first with hexanes (800 ml), followed by 5-20% of acetone in hexanes. The fractions containing product were combined and concentrated to give orange solid 1a (33 g).

Step 1B: (3S,11bR)-9,10-Dimethoxy-3-(2-methylpropyl)-1H,2H,3H,4H,6H,7H,11bH-pyrido[2,1-a]isoquinoline-2-carboxylic acid (1b)

A 1 gallon pressure reactor was charged with a suspension of 1a (94 g, 286 mmol) in methanol (940 ml) and NaOH (343 g, 8.6 mol) in water (940 ml). This mixture was stirred at 120° C. (internal temp) for 67 h. The mixture was cooled to room temp and transferred to a round bottom flask. The mixture was concentrated in a rotavap to ~1 L. The mixture was then adjusted pH to 7 using aqueous 6N HCl under cooling. The mixture was extracted with DCM (2×3 L and 1×2 L). The combined organics were dried over $Na_2SO_4$ and concentrated to give a dark residue (88 g). The dark residue was taken in acetonitrile (500 ml) and stirred for 30 min. The mixture was filtered and the solid was washed with acetonitrile (50 ml). The solid was dried under vacuum for 2 h to afford light brown solid (42 g, 49%). This solid was combined with the filtrate and concentrated to a residue. The residue was dissolved in DCM (150 ml) and loaded onto a silica column packed with DCM. The column was eluted with 0-25% of methanol in DCM. The fractions containing product were combined and concentrated to give (3S,11bR)-9,10-Dimethoxy-3-(2-methylpropyl)-1H,2H,3H,4H,6H,7H,11bH-pyrido[2,1-a]isoquinoline-2-carboxylic acid 1b as a give pale brown solid (71 g, 71% yield, 92% purity, m/z 348.2 [MH$^+$]).

Step 1C: (2R,3S,11bR)-9,10-Dimethoxy-3-(2-methylpropyl)-1H,2H,3H,4H,6H,7H,11bH-pyrido[2,1-a]isoquinolin-2-yl]methanol (1-1)

A 3 L round bottom flask was charged with 1b (73.5 g, 211.5 mmol) and THF (1.48 L). This mixture was stirred and cooled to 10° C. (internal temp). To this mixture was added 1 M LAH in THF (423 ml, 423 mmol) slowly over 20 min keeping the temp below 20° C. The cooling bath was removed and the mixture was warmed up to room temp. The mixture was heated to 55° C. and stirred for 30 min. The mixture was cooled to room temp and then to 10° C. EtOAc (30 ml) was added slowly to quench un-reacted LAH followed by ethanol (30 ml). Then water (150 ml) was added to this mixture. The mixture was then concentrated to remove most of organic solvents. Then the mixture was diluted with water (700 ml) and DCM (1 L). The suspension was filtered through a pad of celite. The filtered cake was washed with DCM (2×500 ml). The combined filtrates were taken in separatory funnel and the layers separated. The aqueous layer was extracted with DCM (1 L). The combined organics were dried over $Na_2SO_4$ and concentrated to give a dark residue. The residue was chromatographed on silica column using 0-10% of methanol in DCM as eluent. The fractions containing product were combined and concentrated to afford foamy orange residue. To this residue hexanes (100 ml) was added and concentrated under reduced pressure at 45° C. for 2 h to afford [(2R,3S,11bR)-9,10-Dimethoxy-3-(2-methylpropyl)-1H,2H,3H,4H,6H,7H,11bH-pyrido[2,1-a]isoquinolin-2-yl]methanol 1-1 as a pale brown solid (51 g, 72%, 95% HPLC purity by 220 nm, m/z 334.2 [MH⁺]). This material may be further purified by silica gel chromatography using 0-10% of methanol in DCM or ethyl acetate as eluent.

Step 1D: [(2R,3S,11bR)-9,10-Dimethoxy-3-(2-methylpropyl)-1H,2H,3H,4H,6H,7H,11bH-pyrido[2,1-a]isoquinolin-2-yl]methanol HCl salt (1-1 HCl)

A 2 L round bottom flask was charged with 1-1 (43 g, 129 mmol) and diethyl ether (860 mL). This mixture was stirred and cooled to 15° C. (internal temp). To this mixture was added 2 M HCl in diethyl ether (97 ml, 193 mmol) slowly over 15 min. A white precipitate formed. The cooling bath was removed and the mixture was warmed to room temp. The mixture was then stirred for 45 min. The mixture was filtered and the filtered solid was washed with diethyl ether (100 ml), with MTBE (100 ml) and then with hexanes (100 ml). The solid was then dried in vacuum oven at 40° C. for 18 h. [(2R,3S,11bR)-9,10-Dimethoxy-3-(2-methylpropyl)-1H,2H,3H,4H,6H,7H,11bH-pyrido[2,1-a]isoquinolin-2-yl]methanol HCl salt 1-1 HCl was isolated as an off-white solid (44.7 g, 94% yield, m/z 334.2 [MH⁺]).

Example 2

[(2R,3S,11bR)-9,10-dimethoxy-3-(2-methylpropyl)-1H,2H,3H,4H,6H,7H,11bH-pyrido[2,1-a]isoquinolin-2-yl]methyl 3-carbamoylpropanoate

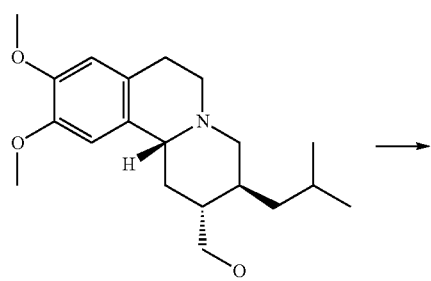

2-1

→

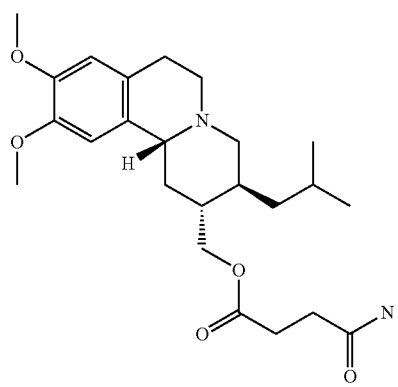

Step 2A:

[(2R,3S,11bR)-9,10-Dimethoxy-3-(2-methylpropyl)-1H,2H,3H,4H,6H,7H,11bH-pyrido[2,1-a]isoquinolin-2-yl]methanol HCl salt (20.0 mg, 0.054 mmol) and 3-carbamoylpropanoic acid (7.6 g, 0.065 mmol) was dissolved in DCM (0.7 mL) followed by N,N-dimethylpyridin-4-amine (7.9 mg, 0.065 mmol), N,N'-dicyclo-hexylmethanediimine (13.0 mg, 0.065 mmol), and trimethylamine (0.037 mL, 0.27 mmol) and the reaction was stirred overnight. The crude reaction mixture was diluted with 0.3 mL MeOH and purified via HPLC yielding [(2R,3S,11bR)-9,10-dimethoxy-3-(2-methylpropyl)-1H,2H,3H,4H,6H,7H,11bH-pyrido[2,1-a]isoquinolin-2-yl]methyl 3-carbamoylpropanoate 2-1 (m/z 433.1 [MH⁺]).

Table 2 below provides the observed (Obs) ion m/z ratio of the other compounds that were made according to the procedure as described in this example.

TABLE 2

| Cpd. | —O—R¹ | Name | Calc mass | Obs mass |
|---|---|---|---|---|
| 2-1 | 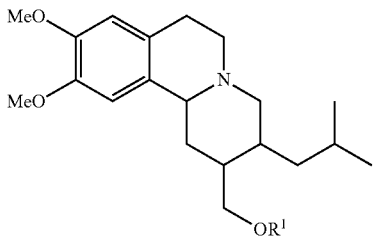 | [(2R,3S,11bR)-9,10-dimethoxy-3-(2-methylpropyl)-1H,2H,3H,4H,6H,7H,11bH-pyrido[2,1-a]isoquinolin-2-yl]methyl 3-carbamoylpropanoate | 432.26 | 433.1 |

TABLE 2-continued

| Cpd. | —O—R¹ | Name | Calc mass | Obs mass |
|---|---|---|---|---|
| 2-2 | | [(2R,3S,11bR)-9,10-dimethoxy-3-(2-methylpropyl)-1H,2H,3H,4H,6H,7H,11bH-pyrido[2,1-a]isoquinolin-2-yl]methyl 3-(morpholin-4-yl)propanoate | 474.31 | 475.2 |
| 2-3 | | [(2R,3S,11bR)-9,10-dimethoxy-3-(2-methylpropyl)-1H,2H,3H,4H,6H,7H,11bH-pyrido[2,1-a]isoquinolin-2-yl]methyl 3-(2,4-dioxo-1,2,3,4-tetrahydroquinazolin-3-yl)propanoate | 549.28 | 550.2 |
| 2-4 | | [(2R,3S,11bR)-9,10-dimethoxy-3-(2-methylpropyl)-1H,2H,3H,4H,6H,7H,11bH-pyrido[2,1-a]isoquinolin-2-yl]methyl 3-(dimethylcarbamoyl)propanoate | 460.29 | 461.1 |
| 2-5 | | [(2R,3S,11bR)-9,10-dimethoxy-3-(2-methylpropyl)-1H,2H,3H,4H,6H,7H,11bH-pyrido[2,1-a]isoquinolin-2-yl]methyl 3-ethanesulfonamidopropanoate | 496.26 | 497.2 |
| 2-6 | | [(2R,3S,11bR)-9,10-dimethoxy-3-(2-methylpropyl)-1H,2H,3H,4H,6H,7H,11bH-pyrido[2,1-a]isoquinolin-2-yl]methyl (3R)-1-benzylpyrrolidine-3-carboxylate | 520.33 | 521.2 |
| 2-7 | | [(2R,3S,11bR)-9,10-dimethoxy-3-(2-methylpropyl)-1H,2H,3H,4H,6H,7H,11bH-pyrido[2,1-a]isoquinolin-2-yl]methyl 3-(dimethylamino)propanoate | 432.3 | 433.2 |

TABLE 2-continued

| Cpd. | —O—R¹ | Name | Calc mass | Obs mass |
|---|---|---|---|---|
| 2-8 | | [(2R,3S,11bR)-9,10-dimethoxy-3-(2-methylpropyl)-1H,2H,3H,4H,6H,7H,11bH-pyrido[2,1-a]isoquinolin-2-yl]methyl 2-[(2R,6S)-2,6-dimethylmorpholin-4-yl]acetate | 488.33 | 489.3 |
| 2-9 | | [(2R,3S,11bR)-9,10-dimethoxy-3-(2-methylpropyl)-1H,2H,3H,4H,6H,7H,11bH-pyrido[2,1-a]isoquinolin-2-yl]methyl 2-carbamoylacetate | 418.25 | 419.1 |
| 2-10 | | [(2R,3S,11bR)-9,10-dimethoxy-3-(2-methylpropyl)-1H,2H,3H,4H,6H,7H,11bH-pyrido[2,1-a]isoquinolin-2-yl]methyl 2-(1-methylpyrrolidin-3-yl)acetate | 458.31 | 459.3 |
| 2-11 | | [(2R,3S,11bR)-9,10-dimethoxy-3-(2-methylpropyl)-1H,2H,3H,4H,6H,7H,11bH-pyrido[2,1-a]isoquinolin-2-yl]methyl (3R)-1-benzylpiperidine-3-carboxylate | 534.35 | 535.3 |
| 2-12 | | [(2R,3S,11bR)-9,10-dimethoxy-3-(2-methylpropyl)-1H,2H,3H,4H,6H,7H,11bH-pyrido[2,1-a]isoquinolin-2-yl]methyl 1-methylpiperidine-3-carboxylate | 458.31 | 4459.3 |
| 2-13 | | [(2R,3S,11bR)-9,10-dimethoxy-3-(2-methylpropyl)-1H,2H,3H,4H,6H,7H,11bH-pyrido[2,1-a]isoquinolin-2-yl]methyl 3-(1H-1,2,3,4-tetrazol-1-yl)propanoate | 457.27 | 458.1 |

TABLE 2-continued

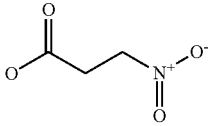

| Cpd. | —O—R[1] | Name | Calc mass | Obs mass |
|---|---|---|---|---|
| 2-14 | 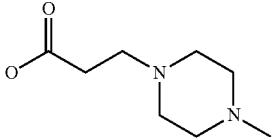 | [(2R,3S,11bR)-9,10-dimethoxy-3-(2-methylpropyl)-1H,2H,3H,4H,6H,7H,11bH-pyrido[2,1-a]isoquinolin-2-yl]methyl 3-nitropropanoate | 434.24 | 435.1 |
| 2-15 | 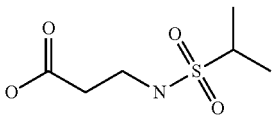 | [(2R,3S,11bR)-9,10-dimethoxy-3-(2-methylpropyl)-1H,2H,3H,4H,6H,7H,11bH-pyrido[2,1-a]isoquinolin-2-yl]methyl 3-(4-methylpiperazin-1-yl)propanoate | 487.34 | 488.3 |
| 2-16 | 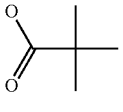 | [(2R,3S,11bR)-9,10-dimethoxy-3-(2-methylpropyl)-1H,2H,3H,4H,6H,7H,11bH-pyrido[2,1-a]isoquinolin-2-yl]methyl 3-(propane-2-sulfonamido)propanoate | 510.28 | 511.2 |
| 2-17 | 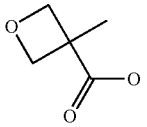 | [(2R,3S,11bR)-9,10-dimethoxy-3-(2-methylpropyl)-1H,2H,3H,4H,6H,7H,11bH-pyrido[2,1-a]isoquinolin-2-yl]methyl 2,2-dimethylpropanoate | 417.29 | 418.31 |
| 2-18 | 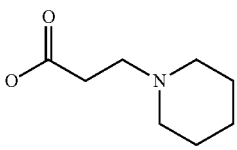 | [(2R,3S,11bR)-9,10-dimethoxy-3-(2-methylpropyl)-1H,2H,3H,4H,6H,7H,11bH-pyrido[2,1-a]isoquinolin-2-yl]methyl 3-methyloxetane-3-carboxylate | 431.27 | 432.32 |
| 2-19 | 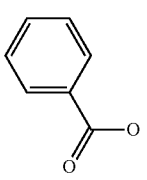 | [(2R,3S,11bR)-9,10-dimethoxy-3-(2-methylpropyl)-1H,2H,3H,4H,6H,7H,11bH-pyrido[2,1-a]isoquinolin-2-yl]methyl 3-(piperidin-1-yl)propanoate | 472.33 | 473.2 |
| 2-20 | 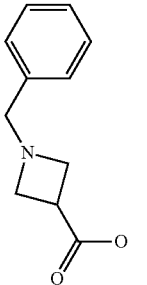 | [(3S,11bR)-9,10-dimethoxy-3-(2-methylpropyl)-1H,2H,3H,4H,6H,7H,11bH-pyrido[2,1-a]isoquinolin-2-yl]methyl benzoate | 437.26 | 438.28 |
| 2-21 | | [(2R,3S,11bR)-9,10-dimethoxy-3-(2-methylpropyl)-1H,2H,3H,4H,6H,7H,11bH-pyrido[2,1-a]isoquinolin-2-yl]methyl 1-benzylazetidine-3-carboxylate | 506.31 | 507.2 |

TABLE 2-continued

| Cpd. | —O—R¹ | Name | Calc mass | Obs mass |
|---|---|---|---|---|
| 2-22 | | [(2R,3S,11bR)-9,10-dimethoxy-3-(2-methylpropyl)-1H,2H,3H,4H,6H,7H,11bH-pyrido[2,1-a]isoquinolin-2-yl]methyl oxane-4-carboxylate | 445.28 | 446.33 |
| 2-23 | | [(2R,3S,11bR)-9,10-dimethoxy-3-(2-methylpropyl)-1H,2H,3H,4H,6H,7H,11bH-pyrido[2,1-a]isoquinolin-2-yl]methyl 3-(3-methyl-1H-pyrazol-1-yl)propanoate | 469.29 | 470.2 |
| 2-24 | | [(2R,3S,11bR)-9,10-dimethoxy-3-(2-methylpropyl)-1H,2H,3H,4H,6H,7H,11bH-pyrido[2,1-a]isoquinolin-2-yl]methyl 2-hydroxy-2-methylpropanoate | 419.27 | 420.24 |
| 2-25 | | [(2R,3S,11bR)-9,10-dimethoxy-3-(2-methylpropyl)-1H,2H,3H,4H,6H,7H,11bH-pyrido[2,1-a]isoquinolin-2-yl]methyl 1-methylpiperidine-4-carboxylate | 458.31 | 459.2 |
| 2-26 | | [(2R,3S,11bR)-9,10-dimethoxy-3-(2-methylpropyl)-1H,2H,3H,4H,6H,7H,11bH-pyrido[2,1-a]isoquinolin-2-yl]methyl (3S)-1-benzylpyrrolidine-3-carboxylate | 520.33 | 521.2 |
| 2-27 | | [3-({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)-2,2,5,5-tetramethylpyrrolidin-1-yl]oxidanyl | 501.33 | 502.2 |

TABLE 2-continued

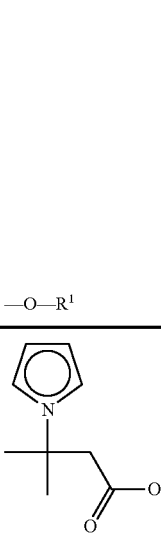

| Cpd. | —O—R[1] | Name | Calc mass | Obs mass |
|---|---|---|---|---|
| 2-28 | 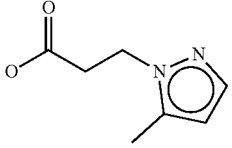 | [(2R,3S,11bR)-9,10-dimethoxy-3-(2-methylpropyl)-1H,2H,3H,4H,6H,7H,11bH-pyrido[2,1-a]isoquinolin-2-yl]methyl 3-methyl-3-(1H-pyrrol-1-yl)butanoate | 482.31 | 483.2 |
| 2-29 | 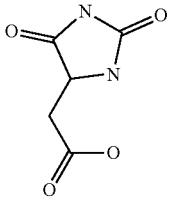 | [(2R,3S,11bR)-9,10-dimethoxy-3-(2-methylpropyl)-1H,2H,3H,4H,6H,7H,11bH-pyrido[2,1-a]isoquinolin-2-yl]methyl 3-(5-methyl-1H-pyrazol-1-yl)propanoate | 469.29 | 470.2 |
| 2-30 | 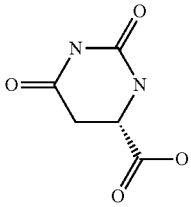 | [(2R,3S,11bR)-9,10-dimethoxy-3-(2-methylpropyl)-1H,2H,3H,4H,6H,7H,11bH-pyrido[2,1-a]isoquinolin-2-yl]methyl 2-(2,5-dioxoimidazolidin-4-yl)acetate | 473.25 | 474.1 |
| 2-31 | 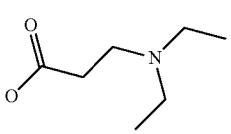 | [(2R,3S,11bR)-9,10-dimethoxy-3-(2-methylpropyl)-1H,2H,3H,4H,6H,7H,11bH-pyrido[2,1-a]isoquinolin-2-yl]methyl (4S)-2,6-dioxo-1,3-diazinane-4-carboxylate | 473.25 | 474.3 |
| 2-32 | 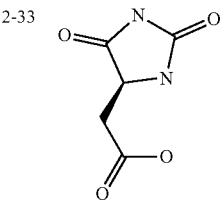 | [(2R,3S,11bR)-9,10-dimethoxy-3-(2-methylpropyl)-1H,2H,3H,4H,6H,7H,11bH-pyrido[2,1-a]isoquinolin-2-yl]methyl 3-(diethylamino)propanoate | 460.33 | 461.1 |
| 2-33 | 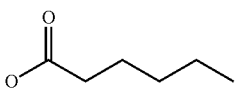 | [(2R,3S,11bR)-9,10-dimethoxy-3-(2-methylpropyl)-1H,2H,3H,4H,6H,7H,11bH-pyrido[2,1-a]isoquinolin-2-yl]methyl 2-[(4S)-2,5-dioxoimidazolidin-4-yl]acetate | 473.25 | 474.1 |
| 2-34 |  | [(2R,3S,11bR)-9,10-dimethoxy-3-(2-methylpropyl)-1H,2H,3H,4H,6H,7H,11bH-pyrido[2,1-a]isoquinolin-2-yl]methyl hexanoate | 431.3 | 432.35 |

TABLE 2-continued

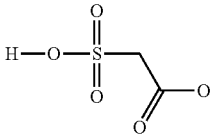

| Cpd. | —O—R[1] | Name | Calc mass | Obs mass |
|---|---|---|---|---|
| 2-35 | 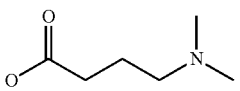 | 2-{[(2R,3S,11bR)-9,10-dimethoxy-3-(2-methylpropyl)-1H,2H,3H,4H,6H,7H,11bH-pyrido[2,1-a]isoquinolin-2-yl]methoxy}-2-oxoethane-1-sulfonic acid | 455.2 | 456.16 |
| 2-36 | 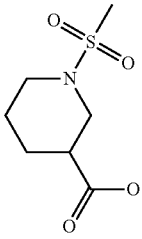 | [(2R,3S,11bR)-9,10-dimethoxy-3-(2-methylpropyl)-1H,2H,3H,4H,6H,7H,11bH-pyrido[2,1-a]isoquinolin-2-yl]methyl 4-(dimethylamino)butanoate | 446.31 | 447.1 |
| 2-37 | 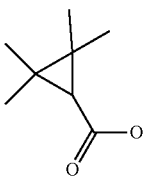 | [(2R,3S,11bR)-9,10-dimethoxy-3-(2-methylpropyl)-1H,2H,3H,4H,6H,7H,11bH-pyrido[2,1-a]isoquinolin-2-yl]methyl 1-methanesulfonylpiperidine-3-carboxylate | 522.28 | 523.2 |
| 2-38 | 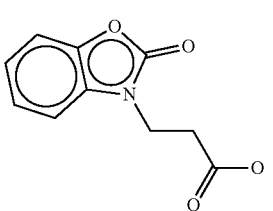 | [(2R,3S,11bR)-9,10-dimethoxy-3-(2-methylpropyl)-1H,2H,3H,4H,6H,7H,11bH-pyrido[2,1-a]isoquinolin-2-yl]methyl 2,2,3,3-tetramethylcyclopropane-1-carboxylate | 457.32 | 458.38 |
| 2-39 |  | [(2R,3S,11bR)-9,10-dimethoxy-3-(2-methylpropyl)-1H,2H,3H,4H,6H,7H,11bH-pyrido[2,1-a]isoquinolin-2-yl]methyl 3-(2-oxo-2,3-dihydro-1,3-benzoxazol-3-yl)propanoate | 522.27 | 523.2 |

Example 3

5-{[(2R,3S,11bR)-9,10-dimethoxy-3-(2-methylpropyl)-1H,2H,3H,4H,6H,7H,11bH-pyrido[2,1-a]isoquinolin-2-yl]methoxy}-3,3-dimethyl-5-oxopentanoic acid

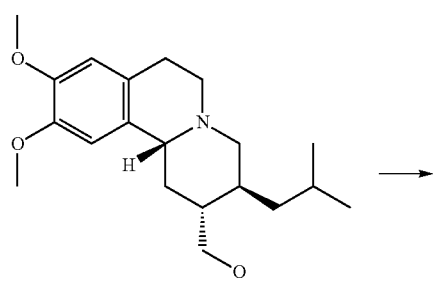

→

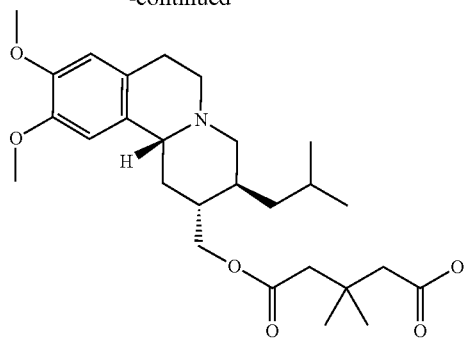

Step 3A:

[(2R,3S,11bR)-9,10-Dimethoxy-3-(2-methylpropyl)-1H,2H,3H,4H,6H,7H,11bH-pyrido[2,1-a]isoquinolin-2-yl]methanol HCl salt (9.2 mg, 0.025 mmol), 4,4-dimethyl-oxane-2,6-dione (3.6 mg, 0.025 mmol), N,N-dimethylpyridin-4-amine (1.0 mg, 0.008 mmol), and ethylbis(propan-2-yl)amine (0.018 mL, 0.10 mmol) were combined in 0.7 mL of DCM and heated to 50° C. overnight. The reaction mixture was diluted with 0.4 mL acetonitrile and purified by HPLC yielding 5-{[(2R,3S,11bR)-9,10-dimethoxy-3-(2-methylpropyl)-1H,2H,3H,4H,6H,7H,11bH-pyrido[2,1-a]isoquinolin-2-yl]methoxy}-3,3-dimethyl-5-oxopentanoic acid 3-1 (m/z 476.1 [MH$^+$]).

Table 3 below provides the observed (Obs) ion m/z ratio of the other compounds that were made according to the procedure as described in this example.

TABLE 3

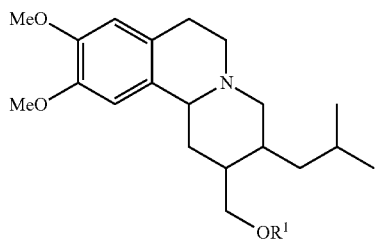

| Cpd. | —O—R$^1$ | Name | Calc mass | Obs mass |
|---|---|---|---|---|
| 3-1 | | 5-{[(2R,3S,11bR)-9,10-dimethoxy-3-(2-methylpropyl)-1H,2H,3H,4H,6H,7H,11bH-pyrido[2,1-a]isoquinolin-2-yl]methoxy}-3,3-dimethyl-5-oxopentanoic acid | 475.29 | 476.1 |
| 3-2 | | 3-{[(2R,3S,11bR)-9,10-dimethoxy-3-(2-methylpropyl)-1H,2H,3H,4H,6H,7H,11bH-pyrido[2,1-a]isoquinolin-2-yl]methoxy}-3-oxopropanoic acid | 419.23 | 420.1 |
| 3-3 | | 5-{[(2R,3S,11bR)-9,10-dimethoxy-3-(2-methylpropyl)-1H,2H,3H,4H,6H,7H,11bH-pyrido[2,1-a]isoquinolin-2-yl]methoxy}-3-methyl-5-oxopentanoic acid | 461.28 | 462.2 |

TABLE 3-continued

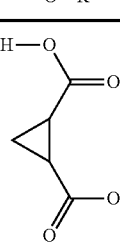

| Cpd. | —O—R¹ | Name | Calc mass | Obs mass |
|---|---|---|---|---|
| 3-4 | 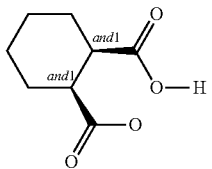 | 2-({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)cyclopropane-1-carboxylic acid | 445.25 | 446.1 |
| 3-5 | 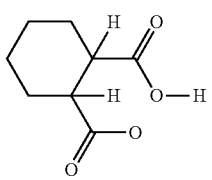 | 2-({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)cyclohexane-1-carboxylic acid | 487.29 | 488.2 |
| 3-6 | 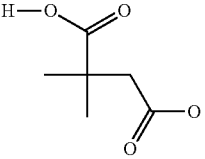 | 2-({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)cyclohexane-1-carboxylic acid | 487.29 | 488.2 |
| 3-7 | 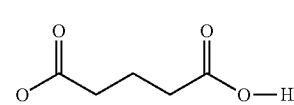 | 4-{[(3S,11bR)-9,10-dimethoxy-3-(2-methylpropyl)-1H,2H,3H,4H,6H,7H,11bH-pyrido[2,1-a]isoquinolin-2-yl]methoxy}-2,2-dimethyl-4-oxobutanoic acid | 461.28 | 462.13 |
| 3-8 | 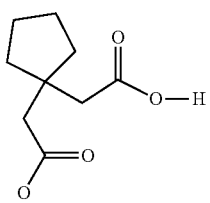 | 5-{[(2R,3S,11bR)-9,10-dimethoxy-3-(2-methylpropyl)-1H,2H,3H,4H,6H,7H,11bH-pyrido[2,1-a]isoquinolin-2-yl]methoxy}-5-oxopentanoic acid | 447.26 | 448.2 |
| 3-9 | 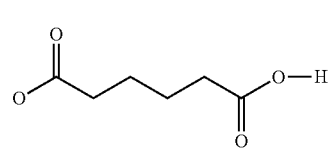 | 2-[1-(2-{[2R,3S,11bR)-9,10-dimethoxy-3-(2-methyylpropyl)-1H,2H,3H,4H,6H,7H,11bH,pyrido[2,1-a]isoquinolin-2-yl]methoxy}-2-oxoethyl)cyclopentyl]acetic acid | 501.31 | 502.2 |
| 3-10 |  | 6-{[2R,3S,11bR)9,10-dimethoxy-3-(2-methylpropyl)-1H,2H,3H,4H,6H,7H,11bH-pyrido[2,1-a]isoquinolin-2-yl]methoxy}-6-oxohexanoic acid | 461.28 | 462.2 |

TABLE 3-continued

| Cpd. | —O—R¹ | Name | Calc mass | Obs mass |
|---|---|---|---|---|
| 3-11 | | 4-{[2R,3S,11bR)-9,10-dimethoxy-3-(2-methylpropyl)-1H,2H,3H,4H,6H,7H,11bH-pyrido[2,1-a]isoquinolin-2-yl]methoxy}-3,3-dimethyl-4-oxobutanoic acid | 461.28 | 462.22 |
| 3-12 | | 5-{[2R,3S,11bR)-9,10-dimethoxy-3-(2-methylpropyl)-1H,2H,3H,4H,6H,7H,11bH-pyrido[2,1-a]isoquinolin-2-yl]methoxy}-2,2-dimethyl-5-oxopentanoic acid | 475.29 | 476.15 |
| 3-13 | | 4-{[2R,3S,11bR)-9,10-dimethoxy-3-(2-methylpropyl)-1H,2H,3H,4H,6H,7H,11bH-pyrido[2,1-a]isoquinolin-2-yl]methoxy}-4-oxobutanoic acid | 433.25 | 434.18 |

Example 4

Synthesis of [(2R,3S,11bR)-9,10-dimethoxy-3-(2-methylpropyl)-1H,2H,3H,4H,6H,7H,11bH-pyrido[2,1-a]isoquinolin-2-yl]methyl piperidine-4-carboxylate

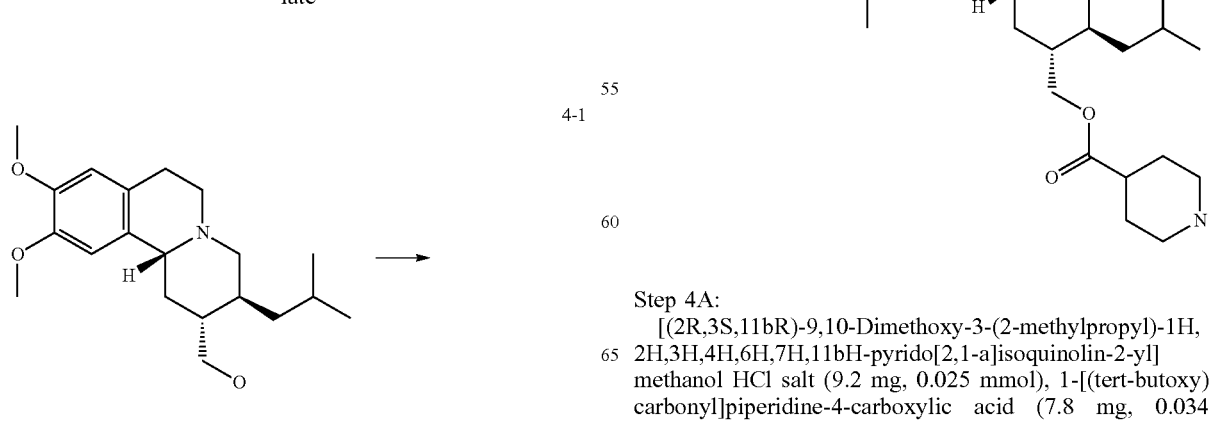

Step 4A:
[(2R,3S,11bR)-9,10-Dimethoxy-3-(2-methylpropyl)-1H,2H,3H,4H,6H,7H,11bH-pyrido[2,1-a]isoquinolin-2-yl]methanol HCl salt (9.2 mg, 0.025 mmol), 1-[(tert-butoxy)carbonyl]piperidine-4-carboxylic acid (7.8 mg, 0.034 mmol), N,N'-dicyclo-hexylmethanediimine (6.2 mg, 0.03 mmol), N,N-dimethylpyridin-4-amine (3.0 mg, 0.025 mmol), and ethylbis(propan-2-yl)amine (0.02 mL, 0.1 mmol) were combined in DCM (1 mL) and the reaction was stirred overnight. The reaction was filtered, concentrated, and redissolved in DCM (1 mL). Next, TFA (0.050 mL) was added and the reaction stirred for one hour. The reaction was concentrated and redissolved in MeOH (1 mL) and purified by HPLC to give [(2R,3S,11bR)-9,10-dimethoxy-3-(2-methylpropyl)-1H,2H,3H,4H,6H,7H,11bH-pyrido[2,1-a]isoquinolin-2-yl]methyl piperidine-4-carboxylate 4-1 (m/z 445.2 [MH$^+$]).

Table 4 below provides the observed (Obs) ion m/z ratio of the other compounds that were made according to the procedure as described in this example.

TABLE 4

| Cpd. | —O—R$^1$ | Name | Calc mass | Obs mass |
|---|---|---|---|---|
| 4-1 | piperidine-4-carboxylate | [(2R,3S,11bR)-9,10-dimethoxy-3-(2-methylpropyl)-1H,2H,3H,4H,6H,7H,11bH-pyrido[2,1-a]isoquinolin-2-yl]methyl piperidine-4-carboxylate | 444.3 | 445.2 |
| 4-2 | (2S)-2-amino-3-phenylpropanoate | [(2R,3S,11bR)-9,10-dimethoxy-3-(2-methylpropyl)-1H,2H,3H,4H,6H,7H,11bH-pyrido[2,1-a]isoquinolin-2-yl]methyl (2S)-2-amino-3-phenylpropanoate | 480.3 | 481.3 |
| 4-3 | (3S)-morpholine-3-carboxylate | [(2R,3S,11bR)-9,10-dimethoxy-3-(2-methylpropyl)-1H,2H,3H,4H,6H,7H,11bH-pyrido[2,1-a]isoquinolin-2-yl]methyl (3S)-morpholine-3-carboxylate | 446.28 | 447.2 |
| 4-4 | (1R,2R)-2-aminocyclohexane-1-carboxylate | [(2R,3S,11bR)-9,10-dimethoxy-3-(2-methylpropyl)-1H,2H,3H,4H,6H,7H,11bH-pyrido[2,1-a]isoquinolin-2-yl]methyl (1R,2R)-2-aminocyclohexane-1-carboxylate | 458.31 | 459.2 |
| 4-5 | (3R)-morpholine-3-carboxylate | [(2R,3S,11bR)-9,10-dimethoxy-3-(2-methylpropyl)-1H,2H,3H,4H,6H,7H,11bH-pyrido[2,1-a]isoquinolin-2-yl]methyl (3R)-morpholine-3-carboxylate | 446.28 | 447.1 |
| 4-6 | 2,3-dihydro-1H-isoindole-1-carboxylate | [(2R,3S,11bR)-9,10-dimethoxy-3-(2-methylpropyl)-1H,2H,3H,4H,6H,7H,11bH-pyrido[2,1-a]isoquinolin-2-yl]methyl 2,3-dihydro-1H-isoindole-1-carboxylate | 478.28 | 479.3 |

TABLE 4-continued

| Cpd. | —O—R¹ | Name | Calc mass | Obs mass |
|---|---|---|---|---|
| 4-7 | pyrrolidin-3-yl carboxylate (3S) | [(2R,3S,11bR)-9,10-dimethoxy-3-(2-methylpropyl)-1H,2H,3H,4H,6H,7H,11bH-pyrido[2,1-a]isoquinolin-2-yl]methyl (3S)-pyrrolidine-3-carboxylate | 430.28 | 431.2 |
| 4-8 | pyrrolidin-3-yl carboxylate | [(2R,3S,11bR)-9,10-dimethoxy-3-(2-methylpropyl)-1H,2H,3H,4H,6H,7H,11bH-pyrido[2,1-a]isoquinolin-2-yl]methyl pyrrolidine-3-carboxylate | 430.28 | 431.2 |
| 4-9 | 1-(aminomethyl)cyclohexyl acetate | [(2R,3S,11bR)-9,10-dimethoxy-3-(2-methylpropyl)-1H,2H,3H,4H,6H,7H,11bH-pyrido[2,1-a]isoquinolin-2-yl]methyl 2-[1-(aminomethyl)cyclohexyl]acetate | 486.35 | 487.2 |
| 4-10 | piperidin-3-yl acetate | [(2R,3S,11bR)-9,10-dimethoxy-3-(2-methylpropyl)-1H,2H,3H,4H,6H,7H,11bH-pyrido[2,1-a]isoquinolin-2-yl]methyl 2-(piperidin-3-yl)acetate | 458.31 | 459.2 |
| 4-11 | 2-aminocyclopentane-1-carboxylate | [(2R,3S,11bR)-9,10-dimethoxy-3-(2-methylpropyl)-1H,2H,3H,4H,6H,7H,11bH-pyrido[2,1-a]isoquinolin-2-yl]methyl 2-aminocyclopentane-1-carboxylate | 444.3 | 445.1 |
| 4-12 | (2S)-2-amino-3-methylbutanoate | [(3S,11bR)-9,10-dimethoxy-3-(2-methylpropyl)-1H,2H,3H,4H,6H,7H,11bH-pyrido[2,1-a]isoquinolin-2-yl]methyl (2S)-2-amino-3-methylbutanoate | 432.3 | 433.3 |
| 4-13 | (3S)-piperidine-3-carboxylate | [(2R,3S,11bR)-9,10-dimethoxy-3-(2-methylpropyl)-1H,2H,3H,4H,6H,7H,11bH-pyrido[2,1-a]isoquinolin-2-yl]methyl (3S)-piperidine-3-carboxylate | 444.3 | 445.1 |

TABLE 4-continued

| Cpd. | —O—R¹ | Name | Calc mass | Obs mass |
|---|---|---|---|---|
| 4-14 | (1-aminocyclohexyl)methyl acetate group | [(2R,3S,11bR)-9,10-dimethoxy-3-(2-methylpropyl)-1H,2H,3H,4H,6H,7H,11bH-pyrido[2,1-a]isoquinolin-2-yl]methyl 2-(1-aminocyclohexyl)acetate | 472.33 | 473.3 |
| 4-15 | 3-methylpiperidine-4-carboxylate | [(2R,3S,11bR)-9,10-dimethoxy-3-(2-methylpropyl)-1H,2H,3H,4H,6H,7H,11bH-pyrido[2,1-a]isoquinolin-2-yl]methyl 3-methylpiperidine-4-carboxylate | 458.31 | 459.3 |
| 4-16 | 2-(pyrrolidin-3-yl)acetate | [(2R,3S,11bR)-9,10-dimethoxy-3-(2-methylpropyl)-1H,2H,3H,4H,6H,7H,11bH-pyrido[2,1-a]isoquinolin-2-yl]methyl 2-(pyrrolidin-3-yl)acetate | 444.3 | 445.3 |
| 4-17 | 3-amino-4-methylpentanoate | [(2R,3S,11bR)-9,10-dimethoxy-3-(2-methylpropyl)-1H,2H,3H,4H,6H,7H,11bH-pyrido[2,1-a]isoquinolin-2-yl]methyl 3-amino-4-methylpentanoate | 446.31 | 447.3 |
| 4-18 | 4-(aminomethyl)benzoate | [(2R,3S,11bR)-9,10-dimethoxy-3-(2-methylpropyl)-1H,2H,3H,4H,6H,7H,11bH-pyrido[2,1-a]isoquinolin-2-yl]methyl 4-(aminomethyl)benzoate | 466.28 | 467.3 |
| 4-19 | 2-amino-2-(2-methoxyphenyl)acetate | [(2R,3S,11bR)-9,10-dimethoxy-3-(2-methylpropyl)-1H,2H,3H,4H,6H,7H,11bH-pyrido[2,1-a]isoquinolin-2-yl]methyl 2-amino-2-(2-methoxyphenyl)acetate | 496.29 | 497.3 |
| 4-20 | piperidine-3-carboxylate | [(2R,3S,11bR)-9,10-dimethoxy-3-(2-methylpropyl)-1H,2H,3H,4H,6H,7H,11bH-pyrido[2,1-a]isoquinolin-2-yl]methyl piperidine-3-carboxylate | 444.3 | 445.1 |

TABLE 4-continued

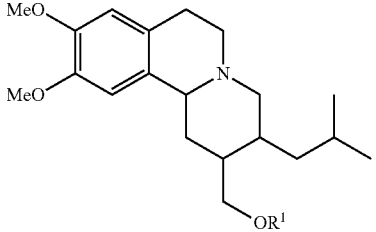

| Cpd. | —O—R¹ | Name | Calc mass | Obs mass |
|---|---|---|---|---|
| 4-21 | 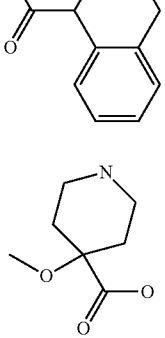 | [(2R,3S,11bR)-9,10-dimethoxy-3-(2-methylpropyl)-1H,2H,3H,4H,6H,7H,11bH-pyrido[2,1-a]isoquinolin-2-yl]methyl 1,2,3,4-tetrahydroisoquinoline-1-carboxylate | 492.3 | 493.3 |
| 4-22 | 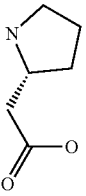 | [(2R,3S,11bR)-9,10-dimethoxy-3-(2-methylpropyl)-1H,2H,3H,4H,6H,7H,11bH-pyrido[2,1-a]isoquinolin-2-yl]methyl 4-methoxypiperidine-4-carboxylate | 474.31 | 475.2 |
| 4-23 | 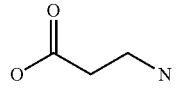 | [(2R,3S,11bR)-9,10-dimethoxy-3-(2-methylpropyl)-1H,2H,3H,4H,6H,7H,11bH-pyrido[2,1-a]isoquinolin-2-yl]methyl 2-[(2R)-pyrrolidin-2-yl]acetate | 444.3 | 445.1 |
| 4-24 | 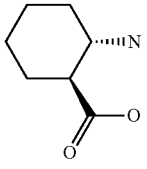 | [(2R,3S,11bR)-9,10-dimethoxy-3-(2-methylpropyl)-1H,2H,3H,4H,6H,7H,11bH-pyrido[2,1-a]isoquinolin-2-yl]methyl 3-aminopropanoate | 404.27 | 405.2 |
| 4-25 | 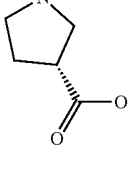 | [(2R,3S,11bR)-9,10-dimethoxy-3-(2-methylpropyl)-1H,2H,3H,4H,6H,7H,11bH-pyrido[2,1-a]isoquinolin-2-yl]methyl (1S,2S)-2-aminocyclohexane-1-carboxylate | 458.31 | 459.2 |
| 4-26 | 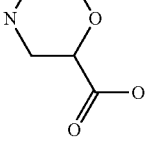 | [(2R,3S,11bR)-9,10-dimethoxy-3-(2-methylpropyl)-1H,2H,3H,4H,6H,7H,11bH-pyrido[2,1-a]isoquinolin-2-yl]methyl (3R)-pyrrolidine-3-carboxylate | 430.28 | 431.2 |
| 4-27 | | [(2R,3S,11bR)-9,10-dimethoxy-3-(2-methylpropyl)-1H,2H,3H,4H,6H,7H,11bH-pyrido[2,1-a]isoquinolin-2-yl]methyl morpholine-2-carboxylate | 446.28 | 447.1 |

TABLE 4-continued

| Cpd. | —O—R¹ | Name | Calc mass | Obs mass |
|---|---|---|---|---|
| 4-28 | | [(2R,3S,11bR)-9,10-dimethoxy-3-(2-methylpropyl)-1H,2H,3H,4H,6H,7H,11bH-pyrido[2,1-a]isoquinolin-2-yl]methyl 2-(pyrrolidin-2-yl)acetate | 444.3 | 445.1 |
| 4-29 | | [(2R,3S,11bR)-9,10-dimethoxy-3-(2-methylpropyl)-1H,2H,3H,4H,6H,7H,11bH-pyrido[2,1-a]isoquinolin-2-yl]methyl (3R)-piperidine-3-carboxylate | 444.3 | 445.1 |
| 4-30 | | [(2R,3S,11bR)-9,10-dimethoxy-3-(2-methylpropyl)-1H,2H,3H,4H,6H,7H,11bH-pyrido[2,1-a]isoquinolin-2-yl]methyl (2R)-2-amino-2-[4-(trifluoromethyl)phenyl]acetate | 534.27 | 535.3 |
| 4-31 | | [(2R,3S,11bR)-9,10-dimethoxy-3-(2-methylpropyl)-1H,2H,3H,4H,6H,7H,11bH-pyrido[2,1-a]isoquinolin-2-yl]methyl 4-aminobutanoate | 418.28 | 419.2 |
| 4-32 | | [(2R,3S,11bR)-9,10-dimethoxy-3-(2-methylpropyl)-1H,2H,3H,4H,6H,7H,11bH-pyrido[2,1-a]isoquinolin-2-yl]methyl morpholine-3-carboxylate | 446.28 | 447.2 |
| 4-33 | | [(2R,3S,11bR)-9,10-dimethoxy-3-(2-methylpropyl)-1H,2H,3H,4H,6H,7H,11bH-pyrido[2,1-a]isoquinolin-2-yl]methyl (2S)-2-amino-2-phenylacetate | 466.28 | 467.3 |
| 4-34 | | [(2R,3S,11bR)-9,10-dimethoxy-3-(2-methylpropyl)-1H,2H,3H,4H,6H,7H,11bH-pyrido[2,1-a]isoquinolin-2-yl]methyl 2-(piperidin-2-yl)acetate | 458.31 | 459.2 |

TABLE 4-continued

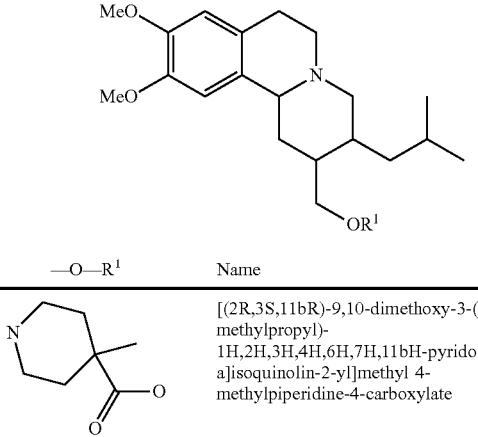

| Cpd. | —O—R[1] | Name | Calc mass | Obs mass |
|---|---|---|---|---|
| 4-35 |  | [(2R,3S,11bR)-9,10-dimethoxy-3-(2-methylpropyl)-1H,2H,3H,4H,6H,7H,11bH-pyrido[2,1-a]isoquinolin-2-yl]methyl 4-methylpiperidine-4-carboxylate | 458.31 | 459.2 |
| 4-36 | 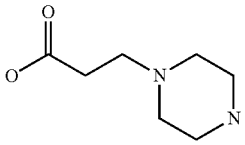 | [(2R,3S,11bR)-9,10-dimethoxy-3-(2-methylpropyl)-1H,2H,3H,4H,6H,7H,11bH-pyrido[2,1-a]isoquinolin-2-yl]methyl 2-[(2S)-pyrrolidin-2-yn]acetate | 444.3 | 445.1 |
| 4-37 |  | [(2R,3S,11bR)-9,10-dimethoxy-3-(2-methylpropyl)-1H,2H,3H,4H,6H,7H,11bH-pyrido[2,1-a]isoquinolin-2-yl]methyl 3-(piperazin-1-yl)propanoate | 473.33 | 474.3 |
| 4-38 | 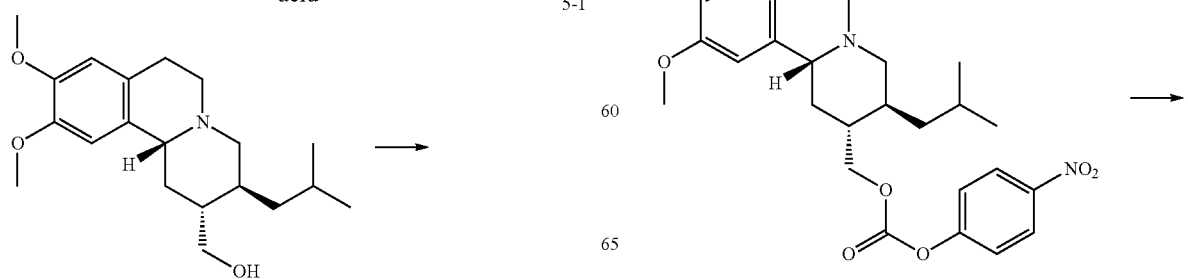 | [(2R,3S,11bR)-9,10-dimethoxy-3-(2-methylpropyl)-1H,2H,3H,4H,6H,7H,11bH-pyrido[2,1-a]isoquinolin-2-yl]methyl 2-[(3R)-pyrrolidin-3-yl]acetate | 444.3 | 445.3 |

Example 5

3-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)amino]propanoic acid 5-1

-continued

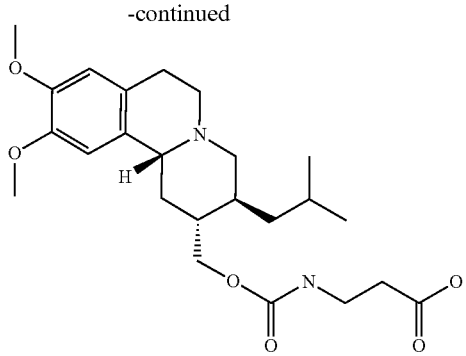

Step 5A:

[(2R,3S,11bR)-9,10-Dimethoxy-3-(2-methylpropyl)-1H,2H,3H,4H,6H,7H,11bH-pyrido[2,1-a]isoquinolin-2-yl] methanol HCl salt (300 mg, 0.81 mmol) and 4-nitrophenyl chloroformate (246 mg, 1.22 mmol) were dissolved in DCM and cooled to 0° C. Ethylbis(propan-2-yl)amine (0.54 mL, 3.25 mmol) was then added, warmed to room temperature, and stirred overnight. The crude reaction mixture was then concentrated and purified by column chromatography (0% to 100% EtOAc in hexanes) to afford [(2R,3S,11bR)-9,10-dimethoxy-3-(2-methylpropyl)-1H,2H,3H,4H,6H,7H,11bH-pyrido[2,1-a]isoquinolin-2-yl]methyl 4-nitrophenyl carbonate 5a (360 mg, 0.722 mmol) as a pale yellow foam in 89% yield (m/z 499.2 [MH$^+$]).

Step 5B:

[(2R,3S,11bR)-9,10-dimethoxy-3-(2-methylpropyl)-1H,2H,3H,4H,6H,7H,11bH-pyrido[2,1-a]isoquinolin-2-yl] methyl 4-nitrophenyl carbonate (12 mg, 0.025 mmol), 3-aminopropanoic acid (3.0 mg, 0.030 mmol) and ethylbis(propan-2-yl)amine (0.017 mL, 0.10 mmol) were dissolved in DMF (0.5 mL) and heated to 50° C. overnight. The crude reaction was then diluted with MeOH (0.5 mL) and purified by HPLC yielding 3-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)amino]propanoic acid 5-1 (m/z 449.1 [MH$^+$]).

Table 5 below provides the observed (Obs) ion m/z ratio of the other compounds that were made according to the procedure as described in this example.

TABLE 5

| Cpd. | —O—R$^1$ | Name | Calc mass | Obs mass |
|---|---|---|---|---|
| 5-1 | | 3-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)amino]propanoic acid | 448.26 | 449.1 |
| 5-2 | | (3S)-3-{[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)amino]methyl}-5-methylhexanoic acid | 518.34 | 519.2 |
| 5-3 | | 4-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)amino]butanoic acid | 462.27 | 463.1 |
| 5-4 | | [(2R,3S,11bR)-9,10-dimethoxy-3-(2-methylpropyl)-1H,2H,3H,4H,6H,7H,11bH-pyrido[2,1-a]isoquinolin-2-yl]methyl 2-[(dimethylamino)methyl]morpholine-4-carboxylate | 503.34 | 504.2 |

TABLE 5-continued

| Cpd. | —O—R¹ | Name | Calc mass | Obs mass |
|---|---|---|---|---|
| 5-5 | | 1-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)amino]cyclopropane-1-carboxylic acid | 460.26 | 461 |
| 5-6 | | 2-[4-({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)morpholin-2-yl]acetic acid | 504.28 | 505.2 |
| 5-7 | | [(2R,3S,11bR)-9,10-dimethoxy-3-(2-methylpropyl)-1H,2H,3H,4H,6H,7H,11bH-pyrido[2,1-a]isoquinolin-2-yl]methyl 4-methylpiperazine-1-carboxylate | 459.31 | 460.13 |
| 5-8 | | [(2R,3S,11bR)-9,10-dimethoxy-3-(2-methylpropyl)-1H,2H,3H,4H,6H,7H,11bH-pyrido[2,1-a]isoquinolin-2-yl]methyl 3-oxopiperazine-1-carboxylate | 459.27 | 459.3 |
| 5-9 | | (1R,2S,3R,4S)-3-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)amino]bicyclo[2.2.1]hept-5-ene-2-carboxylic acid | 512.29 | 513.2 |
| 5-10 | | 4-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)amino]-3-hydroxybutanoic acid | 478.27 | 479.1 |

TABLE 5-continued

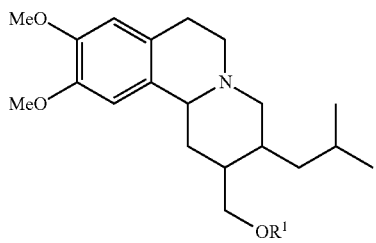

| Cpd. | —O—R¹ | Name | Calc mass | Obs mass |
|---|---|---|---|---|
| 5-11 | 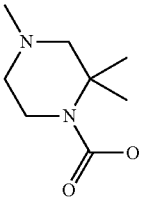 | 3-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)amino]-2-hydroxypropanoic acid | 464.25 | 465.1 |
| 5-12 | 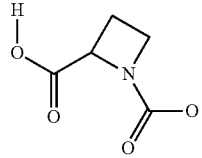 | [(2R,3S,11bR)-9,10-dimethoxy-3-(2-methylpropyl)-1H,2H,3H,4H,6H,7H,11bH-pyrido[2,1-a]isoquinolin-2-yl]methyl 2,2,4-trimethylpiperazine-1-carboxylate | 487.34 | |
| 5-13 | 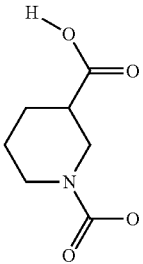 | 1-([[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)azetidine-2-carboxylic acid | 460.26 | 461.1 |
| 5-14 | 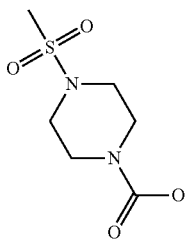 | 1-({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)piperidine-3-carboxylic acid | 488.29 | 489.1 |
| 5-15 | 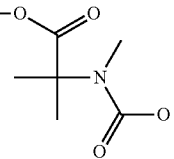 | [(2R,3S,11bR)-9,10-dimethoxy-3-(2-methylpropyl)-1H,2H,3H,4H,6H,7H,11bH-pyrido[2,1-a]isoquinolin-2-yl]methyl 4-methanesulfonylpiperazine-1-carboxylate | 523.27 | 524.15 |
| 5-16 |  | 2-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)(methyl)amino]-2-methylpropanoic acid | 476.29 | |

TABLE 5-continued

| Cpd. | —O—R¹ | Name | Calc mass | Obs mass |
|---|---|---|---|---|
| 5-17 | | (2R)-2-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)(methyl)amino]propanoic acid | 462.27 | 463.1 |
| 5-18 | | [(2R,3S,11bR)-9,10-dimethoxy-3-(2-methylpropyl)-1H,2H,3H,4H,6H,7H,11bH-pyrido[2,1-a]isoquinolin-2-yl]methyl 4-cyclohexylpiperazine-1-carboxylate | 527.37 | 528.25 |
| 5-19 | | (3R)-3-{[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)amino]methyl}-5-methylhexanoic acid | 518.34 | 519.25 |
| 5-20 | | (2S)-2-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)amino]-4-methylpentanoic acid | 490.3 | 491.2 |
| 5-21 | | [(2R,3S,11bR)-9,10-dimethoxy-3-(2-methylpropyl)-1H,2H,3H,4H,6H,7H,11bH-pyrido[2,1-a]isoquinolin-2-yl]methyl 2-methyl-3-oxopiperazine-1-carboxylate | 473.29 | 474.2 |
| 5-22 | | 3-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)amino]-3-methylbutanoic acid | 476.29 | 477.1 |
| 5-23 | | 1-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)amino]cyclohexane-1-carboxylic acid | 502.3 | 503.2 |

TABLE 5-continued

| Cpd. | —O—R[1] | Name | Calc mass | Obs mass |
|---|---|---|---|---|
| 5-24 | | [(2R,3S,11bR)-9,10-dimethoxy-3-(2-methylpropyl)-1H,2H,3H,4H,6H,7H,11bH-pyrido[2,1-a]isoquinolin-2-yl]methyl(1S,4S)-2-oxa-5-azabicyclo[2.2.1]heptane-5-carboxylate | 458.28 | 459.2 |
| 5-25 | | 4-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)(methyl)amino]butanoic acid | 476.29 | 477.1 |
| 5-26 | | 3-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)amino]butanoic acid | 462.27 | 463.15 |
| 5-27 | | 1-({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)azetidine-3-carboxylic acid | 460.26 | 461.0 |
| 5-28 | | 2-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)(methyl)amino]propanoic acid | 462.27 | 463.2 |
| 5-29 | | [(2R,3S,11bR)-9,10-dimethoxy-3-(2-methylpropyl)-1H,2H,3H,4H,6H,7H,11bH-pyrido[2,1-a]isoquinolin-2-yl]methyl N,N-dimethylcarbamate | 404.27 | 405.32 |
| 5-30 | | 2-[({[(2R,3S,11bR)-9,10-dimethoxy-3-(2-methylpropyl)-1H,2H,3H,4H,6H,7H,11bH-pyrido[2,1-a]isoquinolin-2-yl]methoxy{carbonyl)amino]acetic acid | 434.24 | 435.1 |

TABLE 5-continued

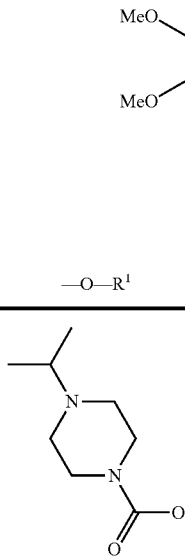

| Cpd. | —O—R[1] | Name | Calc mass | Obs mass |
|---|---|---|---|---|
| 5-31 | 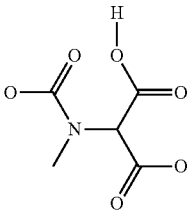 | [(2R,3S,11bR)-9,10-dimethoxy-3-(2-methylpropyl)-1H,2H,3H,4H,6H,7H,11bH-pyrido[2,1-a]isoquinolin-2-yl]methyl 4-(propan-2-yl)piperazine-1-carboxylate | 487.34 | 488.2 |
| 5-32 | 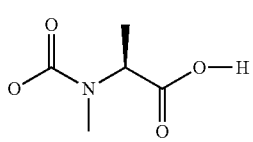 | 2-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)(methyl)amino]-3-methylbutanoic acid | 490.3 | 491.2 |
| 5-33 | 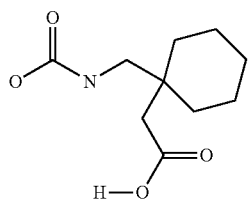 | (2S)-2-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)(methyl)amino]propanoic acid | 462.27 | 463.1 |
| 5-34 | 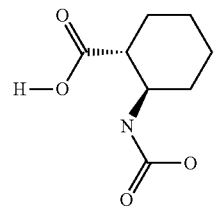 | 2-(1-{[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)amino]methyl}cyclohexyl)acetic acid | 530.34 | 531.2 |
| 5-35 | 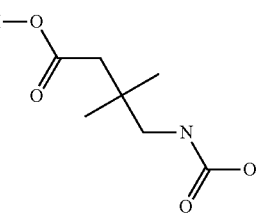 | (1R,2R)-2-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)amino]cyclohexane-1-carboxylic acid | 502.3 | 503.2 |
| 5-36 |  | 4-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)amino]-3,3-dimethylbutanoic acid | 490.3 | 491.2 |

TABLE 5-continued

| Cpd. | —O—R¹ | Name | Calc mass | Obs mass |
|---|---|---|---|---|
| 5-37 | | [(2R,3S,11bR)-9,10-dimethoxy-3-(2-methylpropyl)-1H,2H,3H,4H,6H,7H,11bH-pyrido[2,1-a]isoquinolin-2-yl]methyl (2R)-2-methylmorpholine-4-carboxylate | 460.29 | 461.1 |
| 5-38 | | 3-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)amino]-2,2-dimethylpropanoic acid | 476.29 | 477.1 |
| 5-39 | | 1-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)amino]cyclopentane-1-carboxylic acid | 488.29 | 489.3 |
| 5-40 | | 3-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)amino]bicyclo[2.2.1]heptane-2-carboxylic acid | 514.3 | 515.2 |
| 5-41 | | 2-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)amino]cyclohexane-1-carboxylic acid | 502.3 | 503.2 |
| 5-42 | | 2-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)(methyl)amino]acetic acid | 448.26 | 449.1 |

TABLE 5-continued

| Cpd. | —O—R¹ | Name | Calc mass | Obs mass |
|---|---|---|---|---|
| 5-43 | | 1-({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)-4-(dimethylamino)piperidine-4-carboxylic acid | 531.33 | 532.3 |
| 5-44 | | [(2R,3S,11bR)-9,10-dimethoxy-3-(2-methylpropyl)-1H,2H,3H,4H,6H,7H,11bH-pyrido[2,1-a]isoquinolin-2-yl]methyl (2S)-2-methylmorpholine-4-carboxylate | 460.29 | 461.1 |
| 5-45 | | (2R)-2-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)amino]propanoic acid | 448.26 | 449.1 |
| 5-46 | | 2-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)(methyl)amino]-4-methylpentanoic acid | 504.32 | 505.2 |
| 5-47 | | (2S)-2-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)amino]propanoic acid | 448.26 | 449.1 |
| 5-48 | | [(2R,3S,11bR)-9,10-dimethoxy-3-(2-methylpropyl)-1H,2H,3H,4H,6H,7H,11bH-pyrido[2,1-a]isoquinolin-2-yl]methyl decahydropiperazino[1,2-a]azepine-2-carboxylate | 513.36 | 514.2 |

TABLE 5-continued

| Cpd. | —O—R[1] | Name | Calc mass | Obs mass |
|---|---|---|---|---|
| 5-49 | (pyrrolidine-3-carboxylic acid, N-carbonyloxy) | 1-({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)pyrrolidine-3-carboxylic acid | 474.27 | 475.2 |
| 5-50 | (2R)-2,4-dimethylpiperazine-1-carbonyloxy | [(2R,3S,11bR)-9,10-dimethoxy-3-(2-methylpropyl)-1H,2H,3H,4H,6H,7H,11bH-pyrido[2,1-a]isoquinolin-2-yl]methyl (2R)-2,4-dimethylpiperazine-1-carboxylate | 473.33 | 474.2 |
| 5-51 | (2-methyl-2-(N-methylcarbamoyloxy)propanoic acid) | 2-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)amino]-2-methylpropanoic acid | 462.27 | 463.2 |
| 5-52 | (piperidine-4-carboxylic acid, N-carbonyloxy) | 1-({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)piperidine-4-carboxylic acid | 488.29 | 489.2 |
| 5-53 | (2R,6S)-2,6-dimethylmorpholine-4-carbonyloxy | [(2R,3S,11bR)-9,10-dimethoxy-3-(2-methylpropyl)-1H,2H,3H,4H,6H,7H,11bH-pyrido[2,1-a]isoquinolin-2-yl]methyl (2R,6S)-2,6-dimethylmorpholine-4-carboxylate | 474.31 | 475.2 |

TABLE 5-continued

| Cpd. | —O—R¹ | Name | Calc mass | Obs mass |
|---|---|---|---|---|
| 5-54 | (structure: piperidine-3-carboxylic acid carbamate) | (3R)-1-({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)piperidine-3-carboxylic acid | 488.29 | 489.2 |
| 5-55 | (structure) | 3-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)(methyl)amino]propanoic acid | 462.27 | 463.2 |
| 5-56 | (structure) | (2S)-4-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)amino]-2-hydroxybutanoic acid | 478.27 | 479.1 |
| 5-57 | (structure) | 3-[({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)amino]-2-methylpropanoic acid | 462.27 | 463.2 |

Example 6

[(2R,3S,11 bR)-9,10-dimethoxy-3-(2-methylpropyl)-1H,2H,3H,4H,6H,7H,11bH-pyrido[2,1-a]isoquinolin-2-yl]methyl piperazine-1-carboxylate

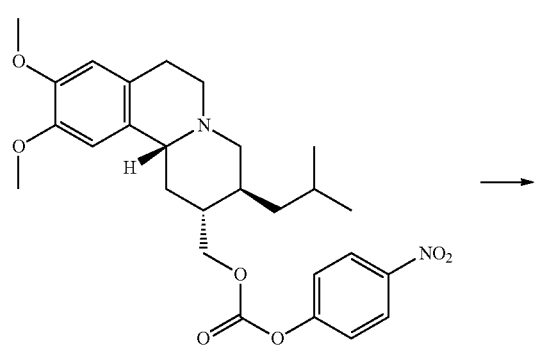

6-1

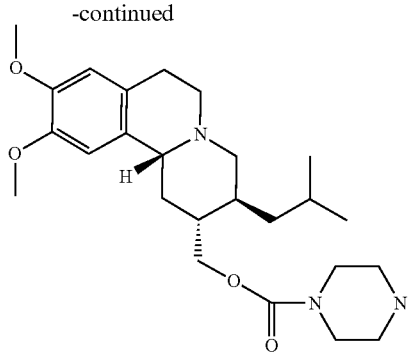

Step 6A:

[(2R,3S,11bR)-9,10-dimethoxy-3-(2-methylpropyl)-1H,2H,3H,4H,6H,7H,11bH-pyrido[2,1-a]isoquinolin-2-yl] methyl 4-nitrophenyl carbonate 5a (12 mg, 0.025 mmol), tert-butyl piperazine-1-carboxylate (6.0 mg, 0.030 mmol) and ethylbis(propan-2-yl)amine (0.017 mL, 0.10 mmol) were dissolved in DCM (0.5 mL) and allowed to stir overnight. Next, TFA (0.050 mL) was added and stirred for 4 hours. The crude reactions were then diluted with MeOH (0.5 mL) and purified by HPLC yielding [(2R,3S,11bR)-9, 10-dimethoxy-3-(2-methylpropyl)-1H,2H,3H,4H,6H,7H,11bH-pyrido[2,1-a]isoquinolin-2-yl]methyl piperazine-1-carboxylate 6-1 (m/z 446.2[MH$^+$]).

Table 6 below provides the observed (Obs) ion m/z ratio of the other compounds that were made according to the procedure as described in this example.

TABLE 6

| Cpd. | —O—R¹ | Name | Calc mass | Obs mass |
|---|---|---|---|---|
| 6-1 | | [(2R,3S,11bR)-9,10-dimethoxy-3-(2-methylpropyl)-1H,2H,3H,4H,6H,7H,11bH-pyrido[2,1-a]isoquinolin-2-yl]methyl piperazine-1-carboxylate | 445.29 | 446.2 |
| 6-2 | | [(2R,3S,11bR)-9,10-dimethoxy-3-(2-methylpropyl)-1H,2H,3H,4H,6H,7H,11bH-pyrido[2,1-a]isoquinolin-2-yl]methyl (2R,5S)-2,5-dimethylpiperazine-1-carboxylate | 473.33 | 474.2 |
| 6-3 | | [(2R,3S,11bR)-9,10-dimethoxy-3-(2-methylpropyl)-1H,2H,3H,4H,6H,7H,11bH-pyrido[2,1-a]isoquinolin-2-yl]methyl (2R)-2-methylpiperazine-1-carboxylate | 459.31 | 460.2 |
| 6-4 | | [(2R,3S,11bR)-9,10-dimethoxy-3-(2-methylpropyl)-1H,2H,3H,4H,6H,7H,11bH-pyrido[2,1-a]isoquinolin-2-yl]methyl 3,8-diazabicyclo[3.2.1]octane-3-carboxylate | 471.31 | 472.2 |
| 6-5 | | [(2R,3S,11bR)-9,10-dimethoxy-3-(2-methylpropyl)-1H,2H,3H,4H,6H,7H,11bH-pyrido[2,1-a]isoquinolin-2-yl]methyl (2S)-2-methylpiperazine-1-carboxylate | 459.31 | 460.2 |
| 6-6 | | [(2R,3S,11bR)-9,10-dimethoxy-3-(2-methylpropyl)-1H,2H,3H,4H,6H,7H,11bH-pyrido[2,1-a]isoquinolin-2-yl]methyl (3R,5S)-3,5-dimethylpiperazine-1-carboxylate | 473.33 | 474.3 |

TABLE 6-continued

| Cpd. | —O—R¹ | Name | Calc mass | Obs mass |
|---|---|---|---|---|
| 6-7 | | [(2R,3S,11bR)-9,10-dimethoxy-3-(2-methylpropyl)-1H,2H,3H,4H,6H,7H,11bH-pyrido[2,1-a]isoquinolin-2-yl]methyl (2R)-2-(hydroxymethyl)piperazine-1-carboxylate | 475.3 | 476.1 |
| 6-8 | | (2R)-4-({[(2R,3S,11bR)-9,10-dimethoxy-3-(2-methylpropyl)-1H,2H,3H,4H,6H,7H,11bH-pyrido[2,1-a]isoquinolin-2-yl]methoxy}carbonyl)piperazine-2-carboxylic acid | 489.28 | 490.2 |
| 6-9 | | [(2R,3S,11bR)-9,10-dimethoxy-3-(2-methylpropyl)-1H,2H,3H,4H,6H,7H,11bH-pyrido[2,1-a]isoquinolin-2-yl]methyl (3S)-3-cyanopiperazine-1-carboxylate | 470.29 | 471.2 |
| 6-10 | | [(2R,3S,11bR)-9,10-dimethoxy-3-(2-methylpropyl)-1H,2H,3H,4H,6H,7H,11bH-pyrido[2,1-a]isoquinolin-2-yl]methyl (1S,4S)-2,5-diazabicyclo[2.2.1]heptane-2-carboxylate | 457.29 | 458.2 |
| 6-11 | | [(2R,3S,11bR)-9,10-dimethoxy-3-(2-methylpropyl)-1H,2H,3H,4H,6H,7H,11bH-pyrido[2,1-a]isoquinolin-2-yl]methyl 3,5-dimethylpiperazine-1-carboxylate | 473.33 | 474.2 |
| 6-12 | | [(2R,3S,11bR)-9,10-dimethoxy-3-(2-methylpropyl)-1H,2H,3H,4H,6H,7H,11bH-pyrido[2,1-a]isoquinolin-2-yl]methyl (2R,6S)-2,6-dimethylpiperazine-1-carboxylate | 473.33 | |

TABLE 6-continued

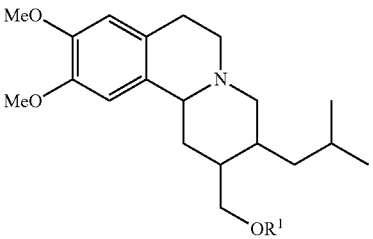

| Cpd. | —O—R[1] | Name | Calc mass | Obs mass |
|---|---|---|---|---|
| 6-13 | 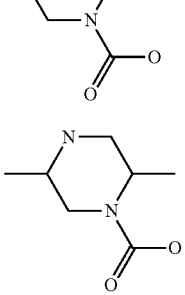 | [(2R,3S,11bR)-9,10-dimethoxy-3-(2-methylpropyl)-1H,2H,3H,4H,6H,7H,11bH-pyrido[2,1-a]isoquinolin-2-yl]methyl (3R)-3-methylpiperazine-1-carboxylate | 459.31 | 460.1 |
| 6-14 | 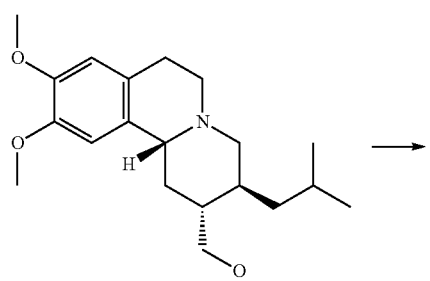 | [(2R,3S,11bR)-9,10-dimethoxy-3-(2-methylpropyl)-1H,2H,3H,4H,6H,7H,11bH-pyrido[2,1-a]isoquinolin-2-yl]methyl 2,5-dimethylpiperazine-1-carboxylate | 473.33 | 474.2 |

Example 7

[(2R,3S,11bR)-9,10-dimethoxy-3-(2-methylpropyl)-1H,2H,3H,4H,6H,7H,11bH-pyrido[2,1-a]isoquinolin-2-yl]methyl diethyl phosphate

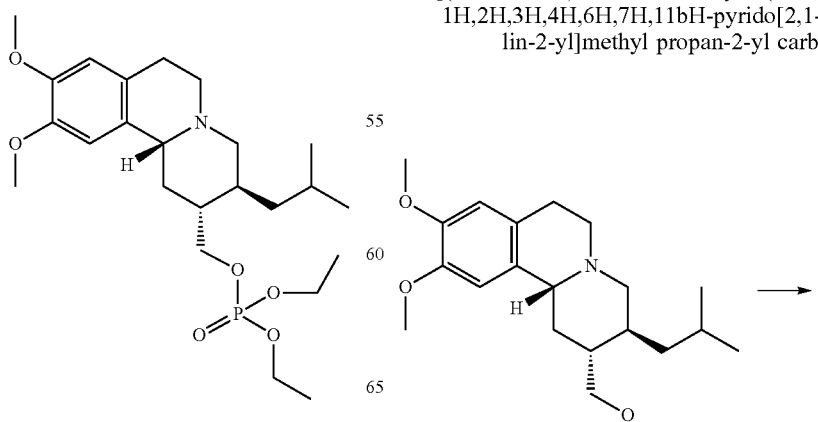

7-1

Step 7A:

[(2R,3S,11bR)-9,10-Dimethoxy-3-(2-methylpropyl)-1H,2H,3H,4H,6H,7H,11bH-pyrido[2,1-a]isoquinolin-2-yl]methanol HCl salt (100 mg, 0.27 mmol) and diethyl chlorophosphonate (140 mg, 0.81 mmol) were dissolved in DCM (2 mL) then ethylbis(propan-2-yl)amine (0.18 mL, 1.1 mmol) was added and the reaction mixture stirred overnight. The crude reaction mixture was diluted with DCM (10 mL), washed with sat. NH$_4$Cl (5 mL) then sat. NaHCO$_3$ (5 mL), dried over MgSO$_4$, filtered and concentrated. The crude mixture was purified by column chromatography (0% to 5% MeOH in DCM) to afford [(2R,3S,11bR)-9,10-dimethoxy-3-(2-methylpropyl)-1H,2H,3H,4H,6H,7H,11bH-pyrido[2,1-a]isoquinolin-2-yl]methyl diethyl phosphate 7-1 (69.0 mg, 0.15 mmol) in a 56% yield. Next the HCL salt was made using 1N HCl in ether (0.16 mL, 0.16 mmol) (m/z 470.8 [MH$^+$]).

Example 8

[(2R,3S,11bR)-9,10-dimethoxy-3-(2-methylpropyl)-1H,2H,3H,4H,6H,7H,11bH-pyrido[2,1-a]isoquinolin-2-yl]methyl propan-2-yl carbonate 8-1

-continued

Example 9

(2R,3S,11bR)-9,10-Dimethoxy-2-(methoxymethyl)-3-(2-methylpropyl)-1H,2H,3H,4H,6H,7H,11bH-pyrido[2,1-a]isoquinoline

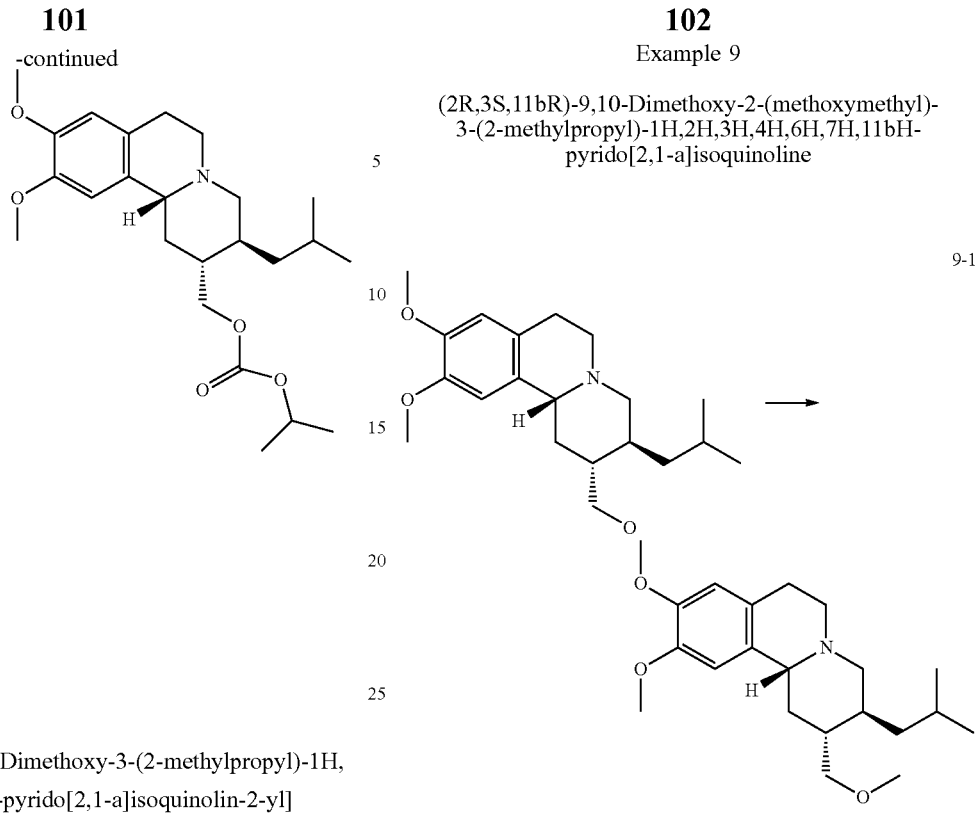

9-1

Step 8A:

[(2R,3S,11bR)-9,10-Dimethoxy-3-(2-methylpropyl)-1H,2H,3H,4H,6H,7H,1bH-pyrido[2,1-a]isoquinolin-2-yl] methanol HCl salt (150 mg, 0.41 mmol) was dissolved in pyridine (12 mL) and cooled to −50° C. Next, propan-2-yl chloroformate (1M) (8.1 mL, 8.1 mmol) was added dropwise. The reaction was stirred at 0° C. for three hours. The crude reaction mixture was diluted with EtOAc (50 mL), washed with sat. NH$_4$Cl (20 mL), dried with MgSO$_4$, filtered and concentrated. The crude reaction mixture was purified by column chromatography (0% to 5% MeOH in DCM) to afford [(2R,3S,11bR)-9,10-dimethoxy-3-(2-methylpropyl)-1H,2H,3H,4H,6H,7H,11bH-pyrido[2,1-a]isoquinolin-2-yl] methyl propan-2-yl carbonate (100 mg, 0.24 mmol) in a 59% yield (m/z 420.3 [MH$^+$]).

Step 9A:

[(2R,3S,11bR)-9,10-Dimethoxy-3-(2-methylpropyl)-1H,2H,3H,4H,6H,7H,11bH-pyrido[2,1-a]isoquinolin-2-yl] methanol HCl salt (15 mg, 0.041 mmol) was dissolved in anhydrous DMF (0.5 mL) and NaH (32 mg, 0.82 mmol) was added and heated to 80° C. The mixture was cooled to 0° C. and MeI (0.003 mL, 0.041 mmol) was added and stirred for 1 hour. The reaction was quenched with sat. NH$_4$Cl (0.5 mL) and extracted with EtOAc (10 mL), the crude reaction mixture was concentrated, redissolved in MeOH (1 mL) and purified by HPLC (m/z 348.1 [MH$^+$]) yielding (2R,3S,11bR)-9,10-dimethoxy-2-(methoxymethyl)-3-(2-methylpropyl)-1H,2H,3H,4H,6H,7H,11bH-pyrido[2,1-a]isoquinoline 9-1.

Table 7 below provides the observed (Obs) ion m/z ratio of the other compounds that were made according to the procedure as described in this example.

TABLE 7

| Cpd. | —O—R$^1$ | Name | Calc mass | Obs mass |
|---|---|---|---|---|
| 9-1 | (structure) | (2R,3S,11bR)-9,10-dimethoxy-2-(methoxymethyl)-3-(2-methylpropyl)-1H,2H,3H,4H,6H,7H,11bH-pyrido[2,1-a]isoquinoline | 347.25 | 348.1 |

TABLE 7-continued

| Cpd. | —O—R¹ | Name | Calc mass | Obs mass |
|---|---|---|---|---|
| 9-2 | | (2R,3S,11bR)-2-[(2-fluoroethoxy)methyl]-9,10-dimethoxy-3-(2-methylpropyl)-1H,2H,3H,4H,6H,7H,11bH-pyrido[2,1-a]isoquinoline | 379.25 | 380.2 |
| 9-3 | | 2-{[(2R,3S,11bR)-9,10-dimethoxy-3-(2-methylpropyl)-1H,2H,3H,4H,6H,7H,11bH-pyrido[2,1-a]isoquinolin-2-yl]methoxy}-1-(4-fluorophenyl)ethan-1-one | 469.26 | 470.15 |
| 9-4 | | (2R,3S,11bR)-9,10-dimethoxy-2-[($^2$H$_3$)methoxymethyl]-3-(2-methylpropyl)-1H,2H,3H,4H,6H,7H,11bH-pyrido[2,1-a]isoquinoline | 350.26 | 351.3 |
| 9-5 | | (2R,3S,11bR)-9,10-dimethoxy-2-[(methoxymethoxy)methyl]-3-(2-methylpropyl)-1H,2H,3H,4H,6H,7H,11bH-pyrido[2,1-a]isoquinoline | 377.26 | 378.3 |
| 9-6 | | (2R,3S,11bR)-9,10-dimethoxy-3-(2-methylpropyl)-2-[(2,2,2-trifluoroethoxy)methyl]-1H,2H,3H,4H,6H,7H,11bH-pyrido[2,1-a]isoquinoline | 415.23 | 416.2 |
| 9-7 | | (2R,3S,11bR)-9,10-dimethoxy-3-(2-methylpropyl)-2-[(3,3,3-trifluoropropoxy)methyl]-1H,2H,3H,4H,6H,7H,11bH-pyrido[2,1-a]isoquinoline | 429.25 | 430.4 |
| 9-8 | | (2R,3S,11bR)-2-(ethoxymethyl)-9,10-dimethoxy-3-(2-methylpropyl)-1H,2H,3H,4H,6H,7H,11bH-pyrido[2,1-a]isoquinoline | 361.26 | 362.1 |
| 9-9 | | (2R,3S,11bR)-9,10-dimethoxy-2-[(2-methylpropoxy)methyl]-3-(2-methylpropyl)-1H,2H,3H,4H,6H,7H,11bH-pyrido[2,1-a]isoquinoline | 389.29 | 390.2 |

Example 10

Benzyl 4-(2-{[(2R,3S,11bR)-9,10-dimethoxy-3-(2-methylpropyl)-1H,2H,3H,4H,6H,7H,11bH-pyrido[2,1-a]isoquinolin-2-yl]methoxy}-2-oxoethyl)piperidine-1-carboxylate

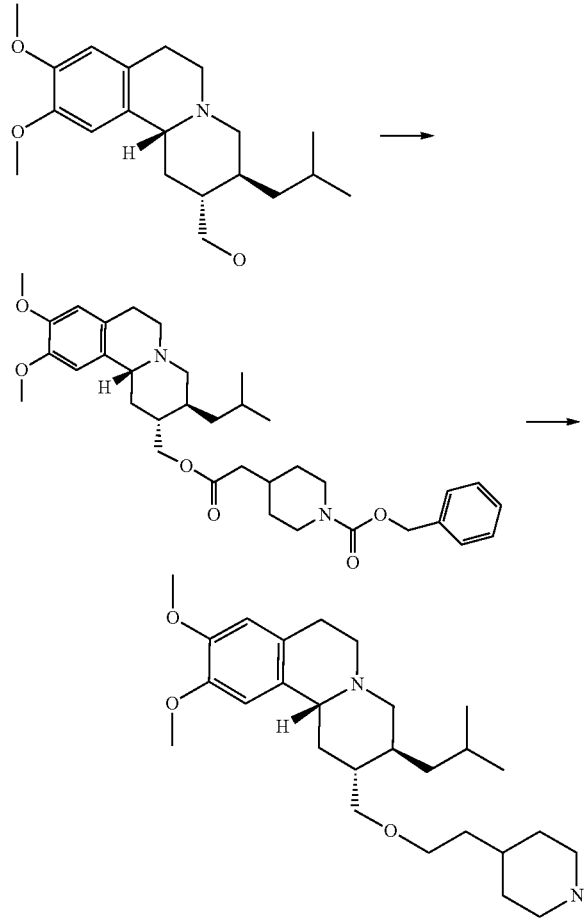

10-1

Step 10A:

[(2R,3S,11bR)-9,10-Dimethoxy-3-(2-methylpropyl)-1H,2H,3H,4H,6H,7H,11bH-pyrido[2,1-a]isoquinolin-2-yl]methanol HCl salt (250 mg, 0.68 mmol) was dissolved in DCM (5 mL) and 2-{1-[(benzyloxy)carbonyl]piperidin-4-yl}acetic acid (244 mg, 0.88 mmol), DCC (181 mg, 0.88 mmol), DMAP (83 mg, 0.68 mmol) and TEA (0.38 mL, 2.7 mmol) were added and the reaction stirred overnight. The crude reaction mixture was diluted with DCM (10 mL) and extracted from sat. NH$_4$Cl (7 mL), dried over MgSO$_4$, filtered and concentrated. The crude mixture was purified by column chromatography (0% to 5% MeOH in DCM) to afford benzyl 4-(2-{[(2R,3S,11bR)-9,10-dimethoxy-3-(2-methylpropyl)-1H,2H,3H,4H,6H,7H,11bH-pyrido[2,1-a]isoquinolin-2-yl]methoxy}-2-oxoethyl)piperidine-1-carboxylate 10a (270 mg, 0.46 mmol) in a 67% yield.

Step 10B:

Benzyl 4-(2-{[(2R,3S,11bR)-9,10-dimethoxy-3-(2-methylpropyl)-1H,2H,3H,4H,6H,7H,11bH-pyrido[2,1-a]isoquinolin-2-yl]methoxy}-2-oxoethyl)piperidine-1-carboxylate 10a (220 mg, 0.37 mmol) was dissolved in DCM (10 mL) and heated to 60° C. Next, Et$_3$SiH (0.29 mL, 1.86 mmol) was added followed by InBr$_3$ (394 mg, 1.11 mmol) and the reaction was stirred at 60° C. for one hour. The reaction mixture was concentrated and redissolved in DMF (5 mL), filtered and purified by HPLC to yield 4-(2-{[(2R,3S,11bR)-9,10-dimethoxy-3-(2-methylpropyl)-1H,2H,3H,4H,6H,7H,11bH-pyrido[2,1-a]isoquinolin-2-yl]methoxy}ethyl)piperidine 10-1 (m/z 445.5 [MH$^+$]).

Table 8 below provides the observed (Obs) ion m/z ratio of the other compounds that were made according to the procedure as described in this example.

TABLE 8

| Cpd. | —O—R$^1$ | Name | Calc mass | Obs mass |
|---|---|---|---|---|
| 10-1 | (piperidinylethyl) | 4-(2-{[(2R,3S,11bR)-9,10-dimethoxy-3-(2-methylpropyl)-1H,2H,3H,4H,6H,7H,11bH-pyrido[2,1-a]isoquinolin-2-yl]methoxy}ethyl)piperidine | 444.34 | 445.5 |

TABLE 8-continued

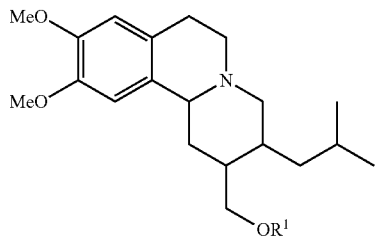

| Cpd. | —O—R[1] | Name | Calc mass | Obs mass |
|---|---|---|---|---|
| 10-2 | pyrrolidin-3-yloxy (3R) | (3R)-3-({[(2R,3S,11bR)-9,10-dimethoxy-3-(2-methylpropyl)-1H,2H,3H,4H,6H,7H,11bH-pyrido[2,1-a]isoquinolin-2-yl]methoxy}methyl)pyrrolidine | 416.3 | 417.4 |
| 10-3 | hexyloxy | 2-[(hexyloxy)methyl]-9,10-dimethoxy-3-(2-methylpropyl)-1H,2H,3H,4H,6H,7H,11bH-pyrido[2,1-a]isoquinoline | 417.32 | 418.4 |
| 10-4 | pyrrolidin-2-yloxy (2S) | (2S)-2-({[(2R,3S,11bR)-9,10-dimethoxy-3-(2-methylpropyl)-1H,2H,3H,4H,6H,7H,11bH-pyrido[2,1-a]isoquinolin-2-yl]methoxy}methyl)pyrrolidine | 416.3 | 417.4 |
| 10-5 | piperidin-4-ylmethoxy | 4-({[(2R,3S,11bR)-9,10-dimethoxy-3-(2-methylpropyl)-1H,2H,3H,4H,6H,7H,11bH-pyrido[2,1-a]isoquinolin-2-yl]methoxy}methyl)piperidine | 430.32 | 431.3 |
| 10-6 | pyrrolidin-3-ylmethoxy | 3-({[(2R,3S,11bR)-9,10-dimethoxy-3-(2-methylpropyl)-1H,2H,3H,4H,6H,7H,11bH-pyrido[2,1-a]isoquinolin-2-yl]methoxy}methyl)pyrrolidine | 416.3 | 417.4 |
| 10-7 | pyrrolidin-2-ylmethoxy (2R) | (2R)-2-({[(2R,3S,11bR)-9,10-dimethoxy-3-(2-methylpropyl)-1H,2H,3H,4H,6H,7H,11bH-pyrido[2,1-a]isoquinolin-2-yl]methoxy}methyl)pyrrolidine | 416.3 | 417.4 |

Example 9

Vmat2 INHIBITOR-Induced Reduction of Locomotor Activity

The effect of 1-1 HC on dopamine depletion was measured using the locomotor activity (LMA) assay. Following a pre-treatment time 60 minutes, male Sprague-Dawley rats (200-250 g) are placed in a clear cage surrounded by photocell detectors (San Diego Instruments). Rat locomotor activity is detected by breaks in the photocell beams and activity is defined as the number of beam breaks in 30 min. Data were analyzed by one-way analysis of variance (ANOVA; SigmaStat version 3.0.1, SPSS, Chicago, Ill.) followed by the Student Newman Keuls post-hoc test for significance. The results of this assay are shown in FIG. 1.

Example 10

Conditioned Avoidance Response Assay of Antipsychotic Activity

The conditioned avoidance response (CAR) test has been shown to be an effective and reliable preclinical model for assessing the antipsychotic activity of compounds. In the CAR paradigm, a rat is trained in a two chamber shuttle box to respond to a conditioned stimulus (auditory) by negative reinforcement. If the animal fails to move to the other chamber upon presentation of an auditory stimulus, a mild foot shock is applied to the side where the rat is located. The rat learns to avoid the mild foot shock by moving to the other chamber upon initiation of the auditory signal, termed a conditioned avoidance response. Crossing to the other chamber during administration of the shock is termed an escape response. If a rat fails to move to the other chamber even upon administration of the foot shock, the rat is considered to have an escape failure. Numerous studies have shown that typical and atypical antipsychotic drugs selectively suppress CAR, thus making it an ideal assay to screen potential antipsychotic compounds (see, e.g., Wadenberg et al., *Biobehav. Rev.* (1999) 23: 851-62).

Male Wistar rats were trained every day for 3 to 4 weeks. In the training session, rats were placed in the CAR two-way shuttle box and the training period of 20 trials ensued. A trial consisted of a 10-sec presentation of an 80 dB white noise followed by a scrambled 0.6 mA foot shock lasting up to 20 sec. The inter-trial interval ranged from 20-60 sec. The rat learned to avoid shock by moving from one compartment to the other when the conditioned stimulus was presented (a conditioned avoidance response). A rat was deemed sufficiently trained if it avoided the shock when presented with the conditioned stimulus at least 19 times out of the 20 trials. Rats that did not pass these criteria were not used.

Figure 2:
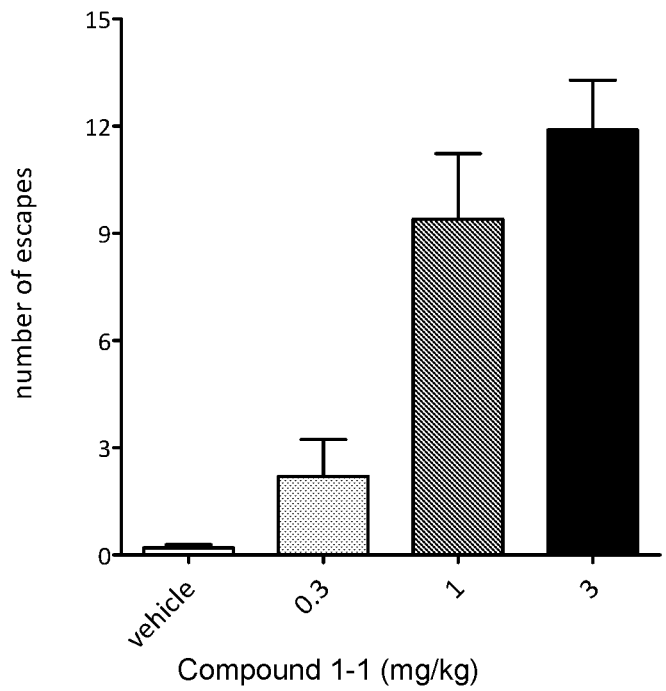
FIG. 2 illustrates the effect of a representative compound (Compound 1-1) in the conditioned avoidance response (CAR) assay of antipsychotic activity.

On test day, trained animals were acclimated in the test room for 30 minutes prior to testing. They were then dosed with compound 1-1 HCl and placed in the CAR two-way shuttle box. In the test, 20 trials were performed on each rat. In each trial the conditioned stimulus was applied (10-sec presentation of 80 dB white noise), followed by the foot shock (a scrambled 0.6 mA foot shock lasting up to 20 sec). If the animal moved to the other chamber on presentation of the conditioned stimulus, it was scored as a conditioned avoidance response. If it moved upon presentation of the foot shock, it was scored as an escape. If it failed to move upon presentation of the foot shock, it was scored as an escape failure. Antipsychotic efficacy is evident by an increase in the number of escapes. Data were analyzed by analysis of variance (ANOVA) followed by post-hoc comparisons with the Bonferroni Test when appropriate. An effect is considered significant if p<0.05. Outliers defined as two standard deviations above or below the mean were detected and were removed from all analysis. Results are shown in FIG. 2 and are reported as mean±SEM for number of escapes.

Example 11

Methods for Determining Vmat2 Inhibitory Activity of a Compound

Examples of techniques for determining the capability of a compound to inhibit VMAT2 are provided below. The procedure is adapted from that described previously (see, e.g., Near, (1986), *Mol. Pharmacol.* 30: 252-57; Teng, et al., *J. Neurochem.* 71, 258-65, 1998). Homogenates from human platelets or Sprague-Dawley rat forebrain were prepared by homogenization and then washed by centrifugation as described previously (see, e.g., Hoare et al., (2003) *Peptides* 24:1881-97). In a total volume of 0.2 mL in low-binding 96-well plates (Corning #3605), twelve concentrations of Compound 1-1 and R,R,R-DHTBZ were competed against 6 nM $^3$H-dihydrotetrabenezine (American Radiolabeled Chemicals, Kd 2.6 nM) on rat forebrain homogenate (100 µg membrane protein per well) or human platelet homogenate (50 µg membrane protein per well) in VMAT2 binding buffer (Dulbecco's phosphate buffered saline, 1 mM EDTA, pH 7.4). Following incubation at 25° C. for two hours, bound radioligand was collected by rapid filtration onto GF/B glass fiber filters using a Unifilter-96 Harvester (PerkinElmer). Filter plates were pre-treated for 10 minutes with 0.1% polyethylenimine, and following harvesting the filter plates were washed with 800 µl VMAT2 binding buffer. Bound radioligand was quantified by scintillation counting using a Topcount NXT (PerkinElmer). The results of the competition binding studies are presented below in Table 9 and Table 10.

TABLE 9

Rat Forebrain VMAT2 Affinity from Competition Binding Studies

| Compound | pKi (n) | Ki (nM) |
|---|---|---|
| Compound 1-1 | 8.6 ± 0.1 (2) | 2.6 |
| R,R,R-DHTBZ | 8.7 ± 0.2 (6) | 1.9 |

TABLE 10

Human Platelet VMAT2 Affinity from Competition Binding Studies

| Compound | pKi (n) | Ki (nM) |
|---|---|---|
| Compound 1-1 | 8.3 ± 0.1 (2) | 5.2 |
| R,R,R-DHTBZ | 8.6 ± 0.3 (3) | 2.6 |

The human Ki's for the compounds listed in Table 11 were determined using a slightly modified procedure shown below (see data in column under the heading "Ki nM"). In a total volume of 0.15 mL in low-binding 96-well plates (Corning #3605), twelve concentrations of Compound 1-1 and R,R,R-DHTBZ were competed against 10 nM $^3$H-dihydrotetrabenezine (American Radiolabeled Chemicals, Kd 2.6 nM) on rat forebrain homogenate (100 µg membrane protein per well) or human platelet homogenate (15 µg membrane protein per well) in VMAT2 binding buffer (Dulbecco's phosphate buffered saline, 1 mM EDTA, pH 7.4). Following incubation at 25° C. for 90 minutes, bound radioligand was collected by rapid filtration onto GF/B glass fiber filters using a Unifilter-96 Harvester (PerkinElmer). Filter plates were pre-treated with 0.1% polyethylenimine and allowed to dry overnight, and following harvesting the filter plates were washed with 800 d VMAT2 binding buffer. Bound radioligand was quantified by scintillation counting using a Topcount NXT (PerkinElmer). In Table 11, compounds having a Ki of less than 10 nM are identified as "+++", compounds having a Ki of from 10 nM to 500 nM are identified as "++", and compounds having a Ki greater than 500 nM are identified as "+" (NT=not tested).

TABLE 11

Activity Data for Representative Compounds

| Cpd. No. | Ki nM | Human (% max. bioavail.) | Rat (% max. bioavail.) |
|---|---|---|---|
| 2-1 | +++ | ++ | + |
| 2-2 | +++ | +++ | +++ |
| 2-3 | +++ | +++ | +++ |
| 2-4 | +++ | +++ | ++ |
| 2-5 | +++ | +++ | ++ |
| 2-6 | +++ | +++ | +++ |
| 2-7 | +++ | ++ | ++ |
| 2-8 | +++ | +++ | ++ |
| 2-9 | +++ | ++ | + |
| 2-10 | +++ | + | ++ |
| 2-11 | +++ | +++ | +++ |
| 2-12 | +++ | ++ | ++ |
| 2-13 | +++ | ++ | ++ |
| 2-14 | +++ | +++ | ++ |
| 2-15 | +++ | ++ | ++ |
| 2-16 | +++ | +++ | +++ |

TABLE 11-continued

Activity Data for Representative Compounds

| Cpd. No. | Ki nM | Human (% max. bioavail.) | Rat (% max. bioavail.) |
|---|---|---|---|
| 2-17 | ++ | +++ | +++ |
| 2-18 | +++ | +++ | +++ |
| 2-19 | +++ | NT | NT |
| 2-20 | NT | +++ | +++ |
| 2-21 | +++ | +++ | +++ |
| 2-22 | +++ | +++ | +++ |
| 2-23 | +++ | +++ | +++ |
| 2-24 | ++ | +++ | +++ |
| 2-25 | +++ | NT | + |
| 2-26 | +++ | +++ | +++ |
| 2-27 | ++ | +++ | ++ |
| 2-28 | ++ | +++ | +++ |
| 2-29 | ++ | +++ | +++ |
| 2-30 | +++ | ++ | + |
| 2-31 | +++ | ++ | ++ |
| 2-32 | +++ | ++ | ++ |
| 2-33 | ++ | NT | NT |
| 2-34 | +++ | +++ | +++ |
| 2-35 | + | + | + |
| 2-36 | +++ | ++ | ++ |
| 2-37 | ++ | +++ | +++ |
| 2-38 | ++ | +++ | +++ |
| 2-39 | +++ | +++ | +++ |
| 3-1 | + | NT | + |
| 3-2 | +++ | +++ | +++ |
| 3-3 | ++ | + | + |
| 3-4 | ++ | + | + |
| 3-5 | ++ | NT | NT |
| 3-6 | ++ | + | + |
| 3-7 | ++ | + | + |
| 3-8 | ++ | + | + |
| 3-9 | ++ | + | + |
| 3-10 | + | + | +++ |
| 3-11 | + | + | + |
| 3-12 | ++ | + | + |
| 3-13 | ++ | + | + |
| 4-1 | +++ | + | + |
| 4-2 | +++ | +++ | +++ |
| 4-3 | ++ | +++ | ++ |
| 4-4 | +++ | ++ | ++ |
| 4-5 | NT | NT | NT |
| 4-6 | ++ | +++ | +++ |
| 4-7 | +++ | + | ++ |
| 4-8 | +++ | + | + |
| 4-9 | NT | NT | NT |
| 4-10 | +++ | + | + |
| 4-11 | ++ | NT | NT |
| 4-12 | +++ | +++ | ++ |
| 4-13 | +++ | + | NT |
| 4-14 | +++ | ++ | ++ |
| 4-15 | +++ | + | + |
| 4-16 | +++ | + | + |
| 4-17 | +++ | ++ | ++ |
| 4-18 | ++ | ++ | ++ |
| 4-19 | ++ | NT | NT |
| 4-20 | +++ | NT | NT |
| 4-21 | ++ | NT | NT |
| 4-22 | +++ | NT | + |
| 4-23 | +++ | ++ | + |
| 4-24 | +++ | NT | NT |
| 4-25 | ++ | ++ | + |
| 4-26 | +++ | + | NT |
| 4-27 | +++ | +++ | ++ |
| 4-28 | +++ | + | + |
| 4-29 | +++ | + | + |
| 4-30 | ++ | NT | NT |
| 4-31 | +++ | + | + |
| 4-32 | ++ | +++ | ++ |
| 4-33 | ++ | + | + |
| 4-34 | +++ | NT | NT |
| 4-35 | +++ | NT | NT |
| 4-36 | +++ | + | ++ |
| 4-37 | +++ | ++ | ++ |
| 4-38 | +++ | + | + |
| 5-1 | +++ | + | + |
| 5-2 | NT | NT | NT |
| 5-3 | + | + | + |
| 5-4 | +++ | + | + |
| 5-5 | ++ | + | + |
| 5-6 | + | + | + |
| 5-7 | + | ++ | ++ |
| 5-8 | NT | NT | NT |
| 5-9 | + | + | + |
| 5-10 | NT | NT | + |
| 5-11 | ++ | + | + |
| 5-12 | NT | NT | NT |
| 5-13 | NT | NT | NT |
| 5-14 | + | + | + |
| 5-15 | ++ | +++ | + |
| 5-16 | NT | NT | NT |
| 5-17 | ++ | + | + |
| 5-18 | +++ | +++ | ++ |
| 5-19 | ++ | + | + |
| 5-20 | ++ | + | + |
| 5-21 | +++ | ++ | + |
| 5-22 | NT | NT | NT |
| 5-23 | ++ | + | + |
| 5-24 | +++ | ++ | + |
| 5-25 | + | + | + |
| 5-26 | + | + | + |
| 5-27 | + | + | + |
| 5-28 | + | + | + |
| 5-29 | ++ | ++ | ++ |
| 5-30 | + | + | + |
| 5-31 | +++ | +++ | ++ |
| 5-32 | +++ | + | + |
| 5-33 | NT | NT | NT |
| 5-34 | ++ | + | + |
| 5-35 | ++ | NT | NT |
| 5-36 | NT | NT | NT |
| 5-37 | +++ | ++ | ++ |
| 5-38 | NT | NT | NT |
| 5-39 | ++ | + | + |
| 5-40 | ++ | + | + |
| 5-41 | ++ | + | + |
| 5-42 | ++ | + | + |
| 5-43 | + | + | + |
| 5-44 | +++ | +++ | ++ |
| 5-45 | + | NT | NT |
| 5-46 | + | + | + |
| 5-47 | ++ | + | + |
| 5-48 | +++ | +++ | +++ |
| 5-49 | ++ | + | NT |
| 5-50 | +++ | +++ | ++ |
| 5-51 | NT | NT | NT |
| 5-52 | + | + | + |
| 5-53 | ++ | ++ | ++ |
| 5-54 | + | + | + |
| 5-55 | NT | NT | NT |
| 5-56 | ++ | + | + |
| 5-57 | + | + | + |
| 6-1 | +++ | + | + |
| 6-2 | +++ | ++ | + |
| 6-3 | NT | + | + |
| 6-4 | +++ | + | + |
| 6-5 | +++ | + | + |
| 6-6 | +++ | + | + |
| 6-7 | +++ | + | + |
| 6-8 | ++ | + | + |
| 6-9 | +++ | ++ | ++ |
| 6-10 | +++ | + | + |
| 6-11 | +++ | + | + |
| 6-12 | NT | NT | NT |
| 6-13 | +++ | + | + |
| 6-14 | +++ | ++ | ++ |
| 7-1 | ++ | +++ | +++ |
| 8-1 | ++ | +++ | +++ |
| 9-1 | +++ | NT | NT |

TABLE 11-continued

Activity Data for Representative Compounds

| Cpd. No. | Ki nM | Human (% max. bioavail.) | Rat (% max. bioavail.) |
|---|---|---|---|
| 9-2 | NT | NT | NT |
| 9-3 | + | NT | NT |
| 9-4 | +++ | NT | NT |
| 9-5 | +++ | NT | NT |
| 9-6 | NT | NT | NT |
| 9-7 | NT | NT | NT |
| 9-8 | +++ | NT | NT |
| 9-9 | NT | NT | NT |
| 10-1 | +++ | NT | ++ |
| 10-2 | +++ | + | ++ |
| 10-3 | ++ | +++ | ++ |
| 10-4 | +++ | +++ | +++ |
| 10-5 | ++ | NT | NT |
| 10-6 | +++ | + | ++ |
| 10-7 | +++ | +++ | ++ |

Another technique that may be routinely performed to determine the capability of a compound to inhibit VMAT2 is provided below. The following procedure is adapted from a previously described method (see Teng, et al., *J. Neurochem.* 71, 258-65, 1998).

Preparation of rat striatal vesicles: Rat striata from three rats are pooled and homogenized in 0.32 M sucrose. The homogenate is then centrifuged at 2,000×g for 10 min at 4° C. and the resulting supernatant is centrifuged at 10,000×g for 30 min at 4° C. The resulting pellet containing the enriched synaptosomal fraction (2 mL) is subjected to osmotic shock by addition of 7 mL of distilled $H_2O$, and subsequently the suspension is homogenized. The osmolarity is restored by the addition of 0.9 mL of 0.25 M HEPES and 0.9 mL of 1.0 M neutral L-(+)-tartaric acid dipotassium salt buffer (pH 7.5), followed by a 20 min centrifugation (20,000×g at 4° C.). The supernatant is then centrifuged for 60 min (55,000×g at 4° C.) and the resulting supernatant is centrifuged for 45 min (100,000×g at 4° C.). The resulting pellet is resuspended in 25 mM HEPES, 100 mM L-(+)-tartaric acid dipotassium salt, 5 mM $MgCl_2$, 10 mM NaCl, 0.05 mM EGTA, pH 7.5 to a protein concentration of 1-2 mg/mL and stored at −80° C. for up to 3 weeks without appreciable loss of binding activity. Immediately before use, the final pellet is resuspended in binding buffer (25 mM HEPES, 100 mM L-(+)-tartaric acid dipotassium salt, 5 mM $MgCl_2$, 10 mM NaCl, 0.05 mM EGTA, 0.1 mM EDTA, 1.7 mM ascorbic acid, pH 7.4).

[$^3$H]-dihydrotetrabenazine (DHTBZ) Binding: Aliquots of the vesicle suspension (0.16 mL, 15 μg of protein/mL) are incubated with competitor compounds (ranging from $10^{-6}$ to $10^{-12}$ M) and 2 nM [$^3$H]-dihydrotetrabenazine (HTBZ; specific activity: 20 Ci/mmol, American Radiolabeled Chemicals, Inc.) for 1 h at room temperature in a total volume of 0.5 mL. The reaction is terminated by rapid filtration of the samples onto Whatman GF/F filters using a Brandel cell harvester. Nonspecific binding is determined using 20 μM tetrabenazine (TBZ). Filters are previously soaked for 2 h with ice-cold polyethyleneimine (0.5%). After the filters are washed three times with the ice-cold buffer, they are placed into scintillation vials with 10 mL scintillation cocktail. Bound radioactivity is determined by scintillation spectrometry.

Example 12

Methods for Determining Metabolic Pathways of a Compound

Figure 3:
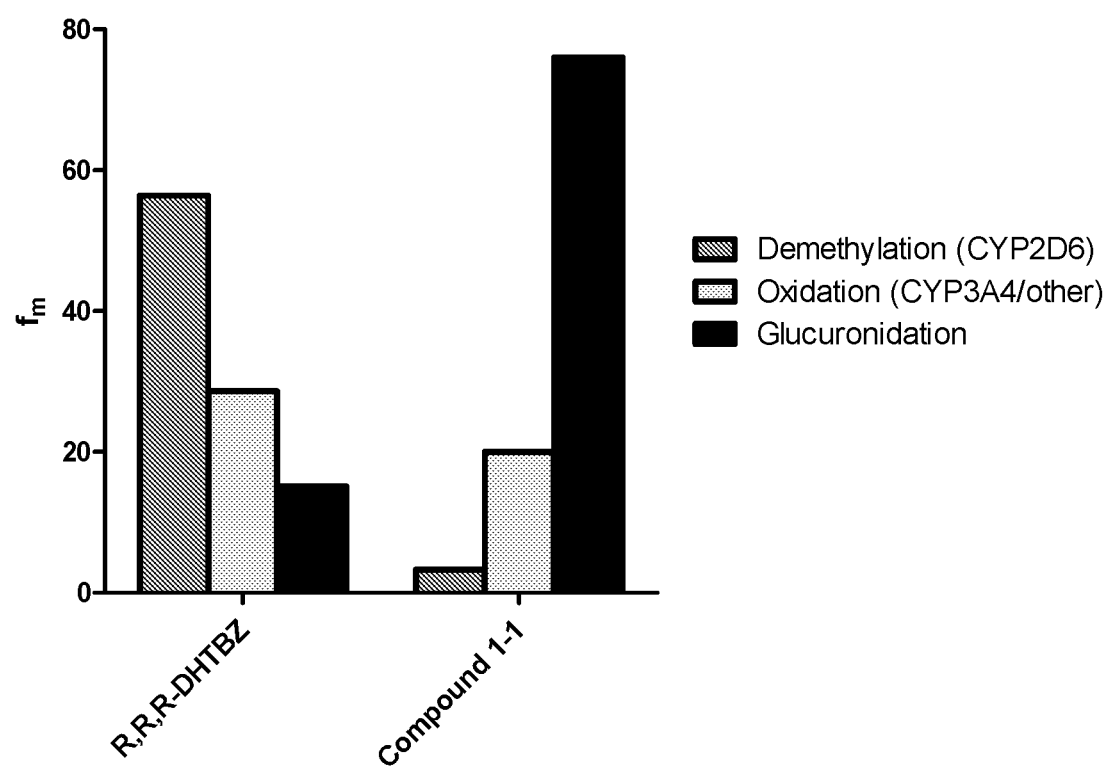
FIG. 3 illustrates the contribution of metabolic pathways to the overall in vitro metabolism of Compound 1-1 and R,R,R-DHTBZ using human hepatocytes.

To investigate differences in the metabolism of Compound 1-1 and R,R,R-DHTBZ in vitro both compounds were incubated with human hepatocytes and the amounts of metabolites formed via the respective demethylation, oxidation, and glucuronidation pathways were determined by LC-MS/MS. The instrument responses for all metabolites were assumed to be approximately equal. For both compounds the percentage of overall in vitro metabolism due to the respective pathways (fraction metabolized, fm) was calculated by dividing the LC/MS peak area of the metabolite(s) formed via a given pathway by the sum of the peak areas of all metabolites monitored. Results of this analysis indicated that R,R,R-DHTBZ was primarily metabolized by demethylation. This demethylation is believed to be catalyzed by CYP2D6. In contrast, Compound 1-1 was primarily metabolized by glucuronidation. FIG. 3 illustrates the contribution of metabolic pathways to the overall in vitro metabolism of Compound 1-1 and R,R,R-DHTBZ using human hepatocytes.

Example 13

Method to Determine Stability of Compounds in Mammalian Liver Microsomes

Test compound (1 uM) was incubated with pooled mixed gender liver microsomes from humans (0.5 mg/mL total protein) and SD rats (0.1 mg/mL total protein) at 37° C. in the presence of an NADPH-generating system containing 50 mM, pH 7.4 potassium phosphate buffer, 3 mM magnesium chloride, 1 mM EDTA, 1 mM NADP, 5 mM glucose-6-phosphate, and 1 Unit/mL glucose-6-phosphate dehydrogenase. All concentrations were relative to the final incubation volume of 250 uL. Incubations were conducted at 37° C. for 0, 5, 10, 20, 40 and 60 minutes in a water bath and terminated by rapid mixing with 300 uL of ice-cold acetonitrile containing 0.1% formic acid. Internal standard was added and proteins were precipitated and removed by centrifugation prior to LC/MS analysis. Aliquots of the resulting supernatant fractions were analyzed by LC/MS monitoring for depletion of parent compound. The resultant peak area ratio versus time data was fitted to a non-linear regression using XLfit Scientific Curve Fitting Software (IDBS Ltd., Surrey, UK) and half-life was calculated from the slope. Pharmacokinetic parameters were predicted using the method described by Obach et al (*J. Pharmcol. Exp. Ther.* 1997; 283: 46.58). Briefly, values for intrinsic clearance were calculated from the in vitro half-life data and were then scaled to represent the clearance expected in the entire animal (human or rat). Additional values calculated included predicted extraction ratio and predicted maximum bioavailability.

By the above procedures, the predicted maximum bioavailability (human and rat) for the compounds listed in Table 11 above were calculated (see data in columns under the headings "Human (% max. bioavail.)" "Rat (% max. bioavail.)", respectively). In Table 11, compounds having a predicted maximum bioavailability of less than 10% are identified as "+++", compounds having a predicted maximum bioavailability from 10% to 50% are identified as "++", and compounds having a predicted maximum bioavailability of greater than 50% to 100% are identified as "+" (NT=not tested).

Example 14

Method to Determine Hydrolytic Stability of Compounds in Mammalian Intestinal S9

Compounds that demonstrated metabolic stability in the human liver microsomal screening assay, defined as scaled intrinsic clearance of <20 mL/min/kg (approximately >50% predicted bioavailability), were selected for further evaluation of hydrolytic stability in an in vitro intestinal S9 assay (SD rat and human). Compounds (1 uM) were incubated with pooled intestinal S9 subcellular preparations (0.5 mg/mL total protein) from SD rats and humans without the addition of protease inhibitor phenylmethylsulfonylflouride. Incubations were carried out in a potassium phosphate buffer (50 mM). All concentrations were relative to the final incubation volume of 125 uL. Incubations were conducted at 37° C. for 0, 5, 10, 20, 40 and 60 minutes in a water bath and terminated by rapid mixing with 150 uL of ice-cold acetonitrile containing 1% formic acid. Internal standard was added and proteins were precipitated and removed by centrifugation prior to LC/MS analysis. Aliquots of the resulting supernatant fractions were analyzed by LC/MS monitoring for depletion of the test compound and formation of compound 1-1. The results were used to categorize compounds based on their potential to hydrolyze to form compound 1-1 in the in vitro assay.

The results of this assay are presented in Table 12. To this end, the compounds listed in Table 12 were separated into three classes of compounds based on their ability to form compound 1-1: high (identified as "+++"); moderate (identified as "++"), and low (identified as "+").

TABLE 12

Activity Data for in vitro Human Intestinal S9 Hydrolysis Assay

| Compound | S9 Assay |
| --- | --- |
| 2-10 | +++ |
| 2-25 | +++ |
| 3-1 | + |
| 3-3 | +++ |
| 3-4 | ++ |
| 3-6 | ++ |
| 3-7 | + |
| 3-8 | +++ |
| 3-9 | ++ |
| 3-10 | +++ |
| 3-11 | ++ |
| 3-12 | +++ |
| 3-13 | ++ |
| 4-1 | ++ |
| 4-7 | ++ |
| 4-8 | ++ |
| 4-10 | ++ |
| 4-13 | +++ |
| 4-15 | + |
| 4-16 | + |
| 4-22 | ++ |
| 4-26 | ++ |
| 4-28 | ++ |
| 4-29 | +++ |
| 4-31 | ++ |
| 4-36 | +++ |
| 4-38 | + |
| 5-1 | + |
| 5-3 | + |

TABLE 12-continued

Activity Data for in vitro Human Intestinal S9 Hydrolysis Assay

| Compound | S9 Assay |
| --- | --- |
| 5-4 | + |
| 5-5 | + |
| 5-6 | + |
| 5-9 | + |
| 5-11 | ++ |
| 5-14 | + |
| 5-17 | + |
| 5-19 | + |
| 5-20 | ++ |
| 5-23 | ++ |
| 5-25 | + |
| 5-26 | + |
| 5-27 | + |
| 5-28 | + |
| 5-30 | + |
| 5-32 | ++ |
| 5-34 | + |
| 5-39 | +++ |
| 5-40 | + |
| 5-41 | + |
| 5-42 | ++ |
| 5-43 | + |
| 5-46 | ++ |
| 5-47 | + |
| 5-49 | + |
| 5-52 | + |
| 5-54 | + |
| 5-56 | + |
| 5-57 | + |
| 6-1 | + |
| 6-3 | + |
| 6-4 | + |
| 6-5 | ++ |
| 6-6 | + |
| 6-7 | + |
| 6-8 | + |
| 6-10 | + |
| 6-11 | + |
| 6-13 | + |

The various embodiments described above can be combined to provide further embodiments. All U.S. patents, U.S. patent application publications, U.S. patent applications, foreign patents, foreign patent applications, and non-patent publications referred to in this specification and/or listed in the Application Data Sheet are incorporated herein by reference in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim the following:

1. A pharmaceutical composition comprising a compound having the following structure:

117

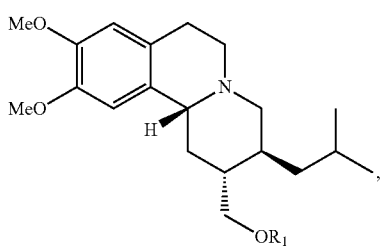

or a pharmaceutically acceptable salt or solvate thereof, in combination with a pharmaceutically acceptable excipient and/or diluent,
wherein:
$R^1$
a) —P(=O)(OR$^3$)$_2$;
b) —C(=O)alkyl, wherein alkyl is optionally substituted with $R^{10}$ and/or $R^{20}$;
c) —C(=O)heterocyclyl, wherein heterocyclyl is optionally substituted with $R^{10}$ and/or $R^{20}$;
d) —C(=O)carbocyclyl, wherein carbocyclyl is optionally substituted with $R^{10}$ and/or $R^{20}$;
e) —C(=O)N(R$_3$)alkyl, wherein alkyl is optionally substituted with $R^{10}$ and/or $R^{20}$;
f) —C(=O)N(R$_3$)carbocyclyl, wherein carbocyclyl is optionally substituted with $R^{10}$ and/or $R^{20}$;
g) —C(=O)Oalkyl, wherein alkyl is optionally substituted with $R^{10}$ and/or $R^{20}$; or
h) alkyl, wherein alkyl is optionally substituted with $R^{10}$ and/or and wherein,
each $R^3$ is independently hydrogen or alkyl;
each $R^{10}$ is independently halo, haloalkyl, cyano, nitro, trimethylsilanyl, —OR$^{30}$, —SR$^{30}$, —OC

118

(O)—R$^{30}$, —N(R$^{30}$)$_2$, —C(O)R$^{30}$, —C(O)OR$^{30}$, —C(O)N(R$^{30}$)$_2$, —N(R$^{30}$)C(O)OR$^{31}$, —N(R$^{30}$)C(O)R$^{31}$, —N(R$^{30}$)C(=NR$^{31}$)N(R$^{32}$)$_2$, —N(R$^{30}$)S(O)$_t$R$^{31}$ (where t is 1 to 2), —S(O)$_t$OR$^{30}$ (where t is 1 to 2), —S(O)$_p$R$^{30}$ (where p is 0 to 2) or —S(O)$_t$N(R$^{30}$)$_2$ (where t is 1 to 2), —OP(=O)(OR$^{30}$)$_2$, or when a single atom bears two $R^{10}$ groups such two $R^{10}$ groups may be taken together to form oxo;

each $R^{20}$ is independently alkyl, alkenyl, aryl, aralkyl, cycloalkyl, cycloalkylalkyl, heterocyclyl, heterocyclalkyl, heteroaryl or heteroarylalkyl, or when a single atom bears two $R^{20}$ groups such two $R^{20}$ groups may be taken together to form cycloalkyl, wherein each of said alkyl, alkenyl, aryl, aralkyl, cycloalkyl, cycloalkylalkyl, heterocyclyl, heterocyclalkyl, heteroaryl and heteroarylalkyl groups is optionally substituted with $R^{10}$ and/or $R^{22}$;

each $R^{22}$ is independently alkyl, alkenyl, aryl, aralkyl, cycloalkyl, cycloalkylalkyl, heterocyclyl, heterocyclalkyl, heteroaryl or heteroarylalkyl, wherein each of said alkyl, alkenyl, aryl, aralkyl, cycloalkyl, cycloalkylalkyl, heterocyclyl, heterocyclalkyl, heteroaryl and heteroarylalkyl groups is optionally substituted with $R^{10}$; and each $R^{30}$, $R^{31}$ and $R^{32}$ is independently hydrogen or alkyl.

2. The pharmaceutical composition of claim 1, wherein $R^1$ is —P(=O)(OR$^3$)$_2$.

3. The pharmaceutical composition of claim 1, wherein $R^1$ is —C(=O)alkyl, and wherein alkyl is optionally substituted with $R^{10}$ and/or $R^{20}$.

4. The pharmaceutical composition of claim 1, wherein the compound is selected from one of the following:

2-1

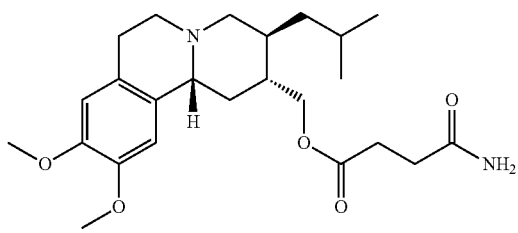 [SMILES: COc1cc2c(cc1OC)[C@H]1C[C@@H](COC(=O)CCC(N)=O)[C@H](CC(C)C)CN1CC2]

2-2

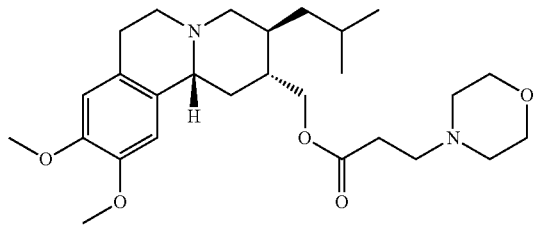 [SMILES: COc1cc2c(cc1OC)[C@H]1C[C@@H](COC(=O)CCN3CCOCC3)[C@H](CC(C)C)CN1CC2]

2-3

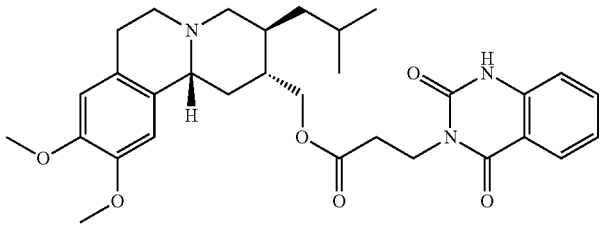 [SMILES: COc1cc2c(cc1OC)[C@H]1C[C@@H](COC(=O)CCn3c(=O)[nH]c4ccccc4c3=O)[C@H](CC(C)C)CN1CC2]

-continued
2-4 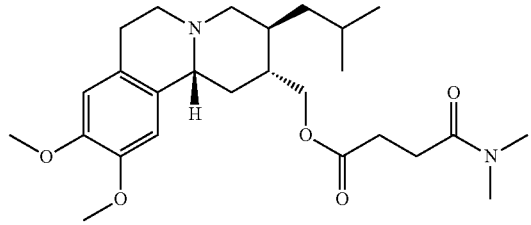
2-5 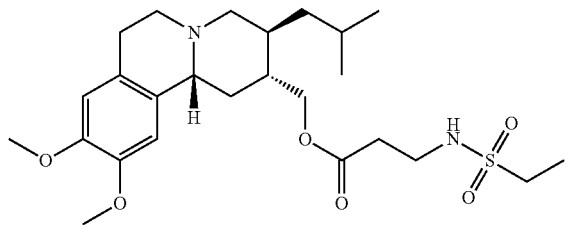 [SMILES: CCS(=O)(=O)NCCC(=O)OC[C@@H]1C[C@@H]2c3cc(OC)c(OC)cc3CCN2C[C@H]1CC(C)C]
2-7 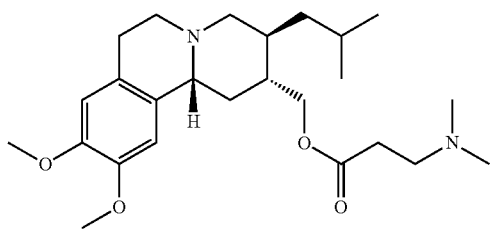
2-8 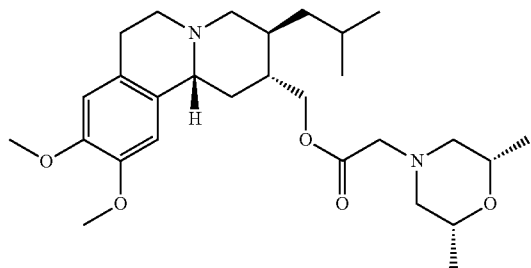
2-9 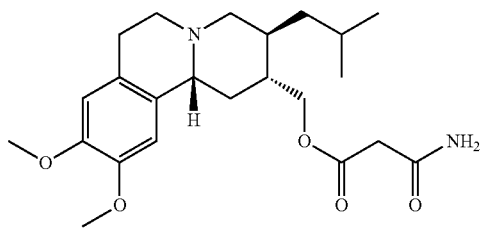 [SMILES: COc1cc2c(cc1OC)[C@H]1C[C@@H](COC(=O)CC(N)=O)[C@H](CC(C)C)CN1CC2]
2-10 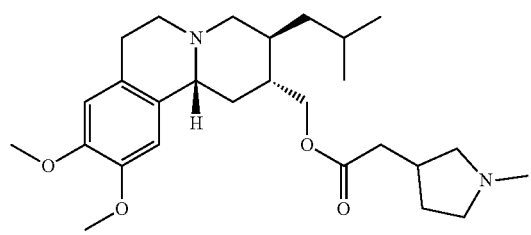

-continued
2-13 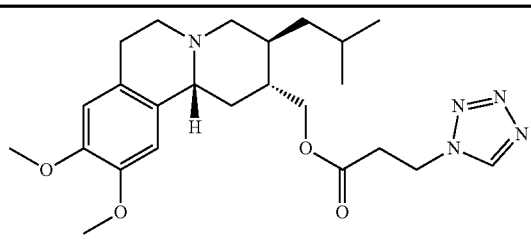
2-14 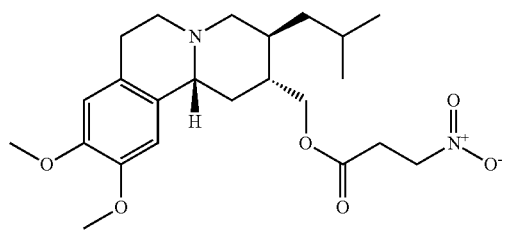 [SMILES: COc1cc2c(cc1OC)[C@H]1C[C@@H](COC(=O)CC[N+](=O)[O-])[C@H](CC(C)C)CN1CC2]
2-15 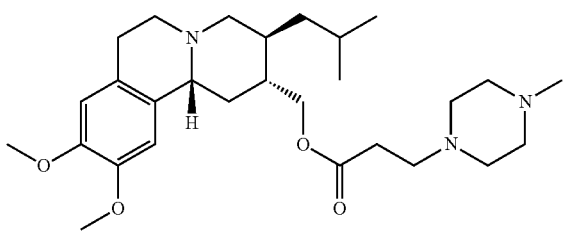
2-16 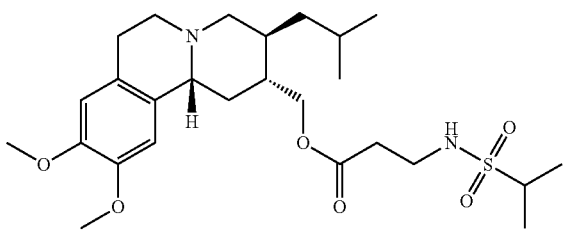 [SMILES: COc1cc2c(cc1OC)[C@H]1C[C@@H](COC(=O)CCNS(=O)(=O)C(C)C)[C@H](CC(C)C)CN1CC2]
2-17 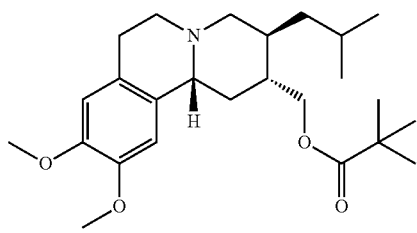 [SMILES: COc1cc2c(cc1OC)[C@H]1C[C@@H](COC(=O)C(C)(C)C)[C@H](CC(C)C)CN1CC2]
2-19 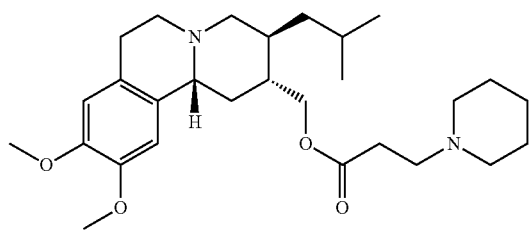 [SMILES: COc1cc2c(cc1OC)[C@H]1C[C@@H](COC(=O)CCN3CCCCC3)[C@H](CC(C)C)CN1CC2]
2-23 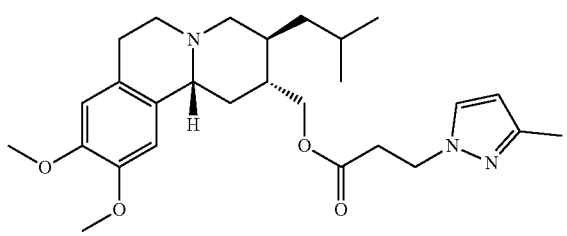

2-24 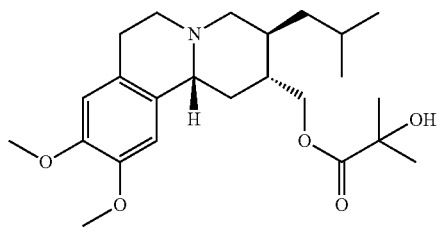 [SMILES: COc1cc2c(cc1OC)[C@H]1C[C@@H](COC(=O)C(C)(C)O)[C@H](CC(C)C)CN1CC2]
2-28 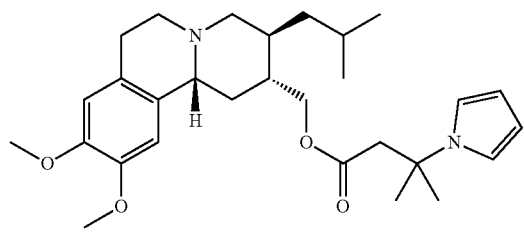 [SMILES: COc1cc2c(cc1OC)[C@H]1C[C@@H](COC(=O)CC(C)(C)n3cccc3)[C@H](CC(C)C)CN1CC2]
2-29 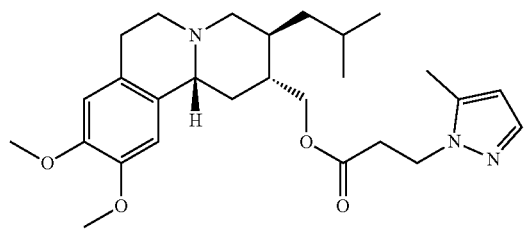 [SMILES: COc1cc2c(cc1OC)[C@H]1C[C@@H](COC(=O)CCn3nccc3C)[C@H](CC(C)C)CN1CC2]
2-30 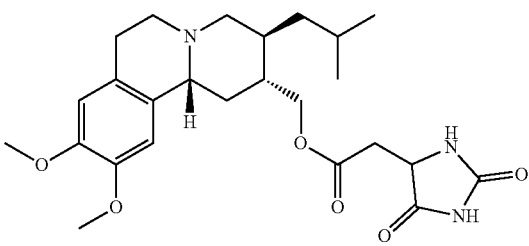 [SMILES: COc1cc2c(cc1OC)[C@H]1C[C@@H](COC(=O)CC3NC(=O)NC3=O)[C@H](CC(C)C)CN1CC2]
2-32 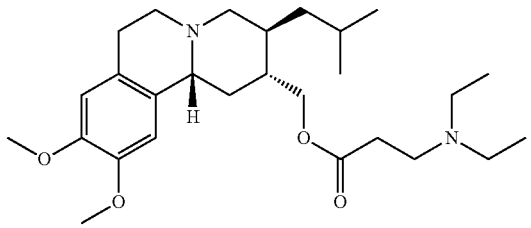 [SMILES: CCN(CC)CCC(=O)OC[C@@H]1C[C@@H]2c3cc(OC)c(OC)cc3CCN2C[C@H]1CC(C)C]
2-33 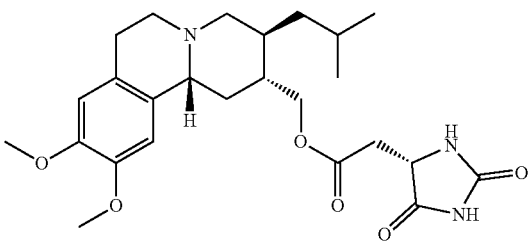 [SMILES: COc1cc2c(cc1OC)[C@H]1C[C@@H](COC(=O)C[C@@H]3NC(=O)NC3=O)[C@H](CC(C)C)CN1CC2]

-continued
2-34
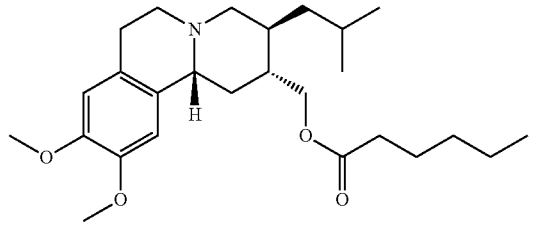 [SMILES: CCCCCC(=O)OC[C@@H]1C[C@@H]2c3cc(OC)c(OC)cc3CCN2C[C@H]1CC(C)C]
2-35
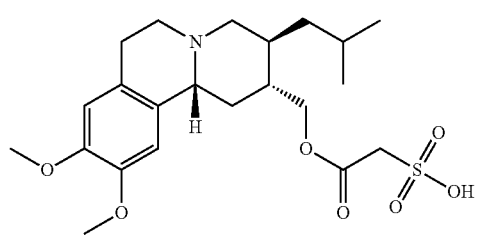 [SMILES: COc1cc2c(cc1OC)[C@H]1C[C@@H](COC(=O)CS(=O)(=O)O)[C@H](CC(C)C)CN1CC2]
2-36
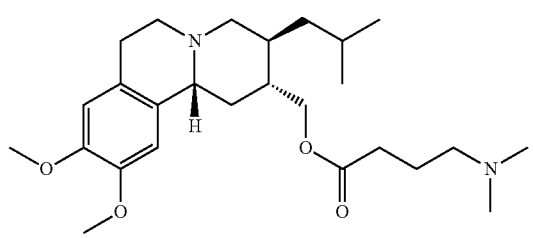
2-39
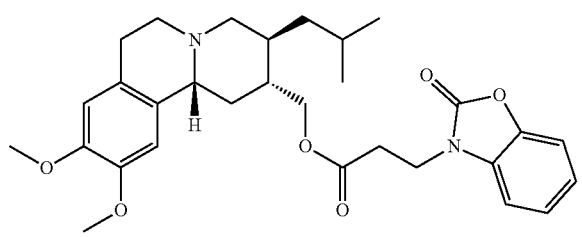 [SMILES: COc1cc2c(cc1OC)[C@H]1C[C@@H](COC(=O)CCn3c(=O)oc4ccccc43)[C@H](CC(C)C)CN1CC2]
3-1
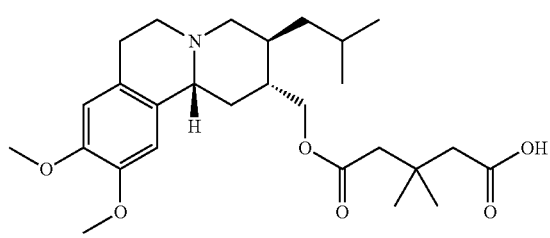 [SMILES: COc1cc2c(cc1OC)[C@H]1C[C@@H](COC(=O)CC(C)(C)CC(=O)O)[C@H](CC(C)C)CN1CC2]
3-2
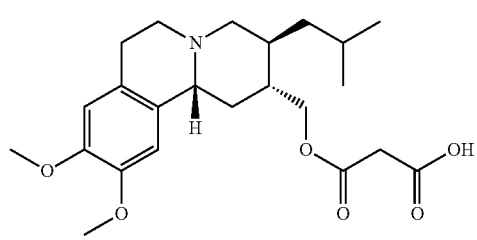 [SMILES: COc1cc2c(cc1OC)[C@H]1C[C@@H](COC(=O)CC(=O)O)[C@H](CC(C)C)CN1CC2]

-continued
3-3 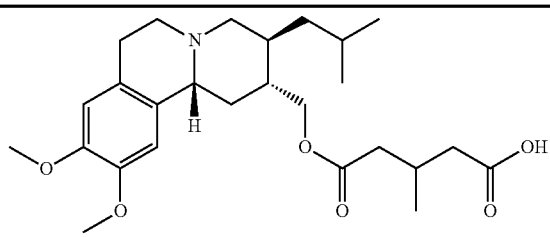
3-7 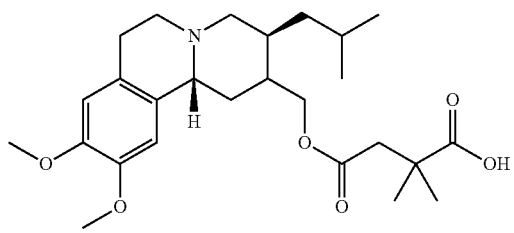 [SMILES: COc1cc2c(cc1OC)[C@H]1CC(COC(=O)CC(C)(C)C(=O)O)[C@H](CC(C)C)CN1CC2]
3-8 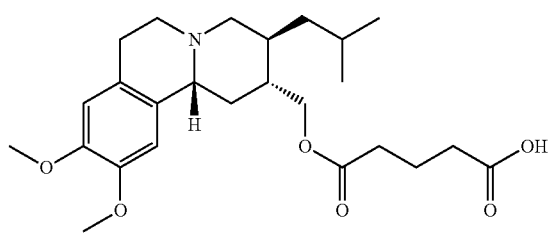 [SMILES: COc1cc2c(cc1OC)[C@H]1C[C@@H](COC(=O)CCCC(=O)O)[C@H](CC(C)C)CN1CC2]
3-9 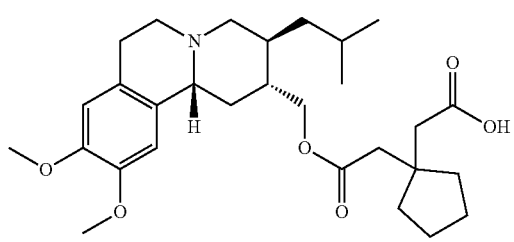 [SMILES: COc1cc2c(cc1OC)[C@H]1C[C@@H](COC(=O)CC3(CC(=O)O)CCCC3)[C@H](CC(C)C)CN1CC2]
3-10 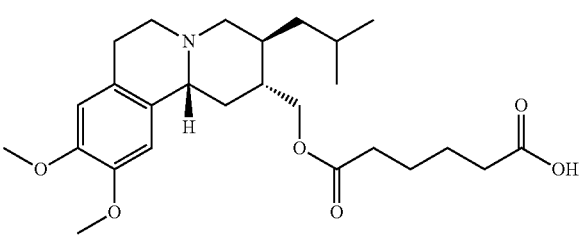 [SMILES: COc1cc2c(cc1OC)[C@H]1C[C@@H](COC(=O)CCCCC(=O)O)[C@H](CC(C)C)CN1CC2]
3-11 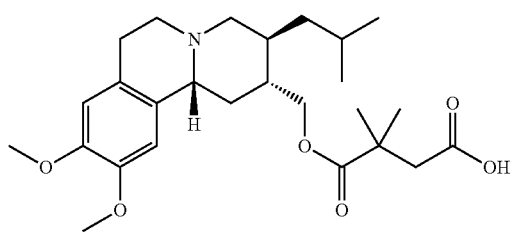 [SMILES: COc1cc2c(cc1OC)[C@H]1C[C@@H](COC(=O)C(C)(C)CC(=O)O)[C@H](CC(C)C)CN1CC2]
3-12 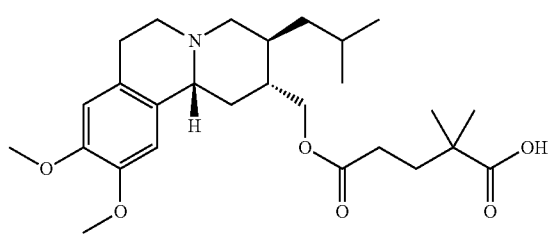 [SMILES: COc1cc2c(cc1OC)[C@H]1C[C@@H](COC(=O)CCC(C)(C)C(=O)O)[C@H](CC(C)C)CN1CC2]

3-13 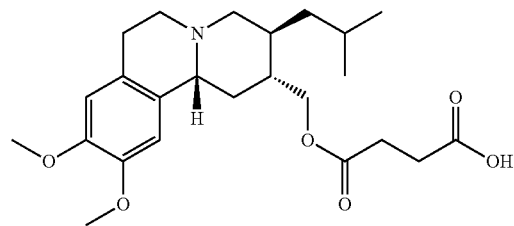 [SMILES: COc1cc2c(cc1OC)[C@H]1C[C@@H](COC(=O)CCC(=O)O)[C@H](CC(C)C)CN1CC2]
4-2 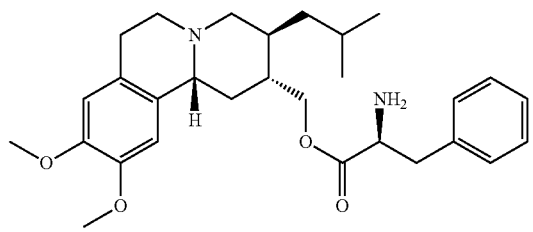 [SMILES: COc1cc2c(cc1OC)[C@H]1C[C@@H](COC(=O)[C@@H](N)Cc3ccccc3)[C@H](CC(C)C)CN1CC2]
4-9 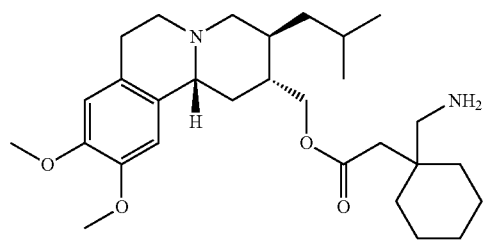 [SMILES: COc1cc2c(cc1OC)[C@H]1C[C@@H](COC(=O)CC3(CN)CCCCC3)[C@H](CC(C)C)CN1CC2]
4-10 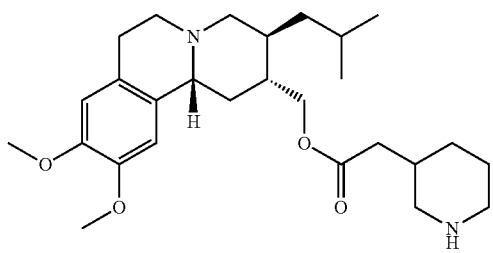 [SMILES: COc1cc2c(cc1OC)[C@H]1C[C@@H](COC(=O)CC3CCCNC3)[C@H](CC(C)C)CN1CC2]
4-12 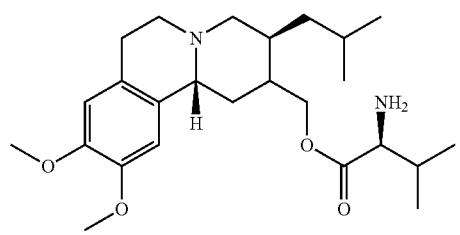 [SMILES: COc1cc2c(cc1OC)[C@H]1CC(COC(=O)[C@@H](N)C(C)C)[C@H](CC(C)C)CN1CC2]
4-14 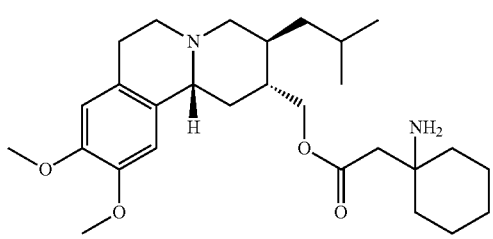 [SMILES: COc1cc2c(cc1OC)[C@H]1C[C@@H](COC(=O)CC3(N)CCCCC3)[C@H](CC(C)C)CN1CC2]

4-16 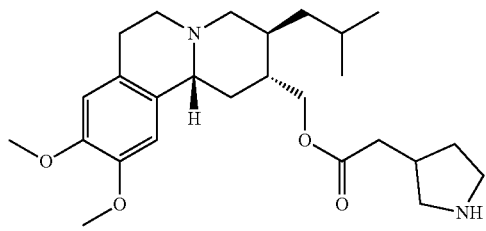 [SMILES: COc1cc2c(cc1OC)[C@H]1C[C@@H](COC(=O)CC3CCNC3)[C@H](CC(C)C)CN1CC2]
4-17 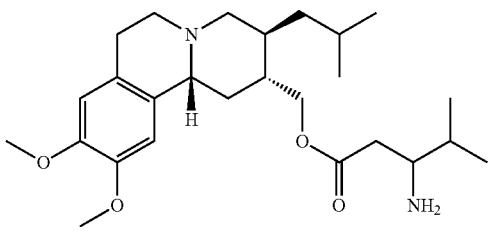 [SMILES: COc1cc2c(cc1OC)[C@H]1C[C@@H](COC(=O)CC(N)C(C)C)[C@H](CC(C)C)CN1CC2]
4-19 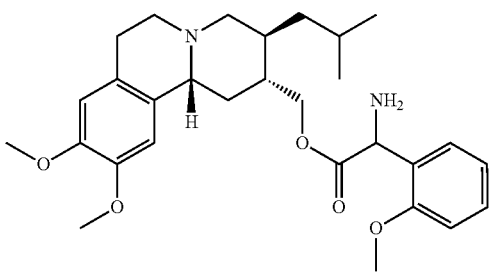 [SMILES: COc1cc2c(cc1OC)[C@H]1C[C@@H](COC(=O)C(N)c3ccccc3OC)[C@H](CC(C)C)CN1CC2]
4-23 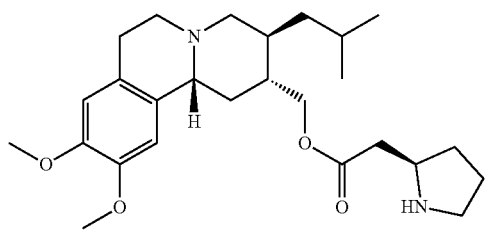 [SMILES: COc1cc2c(cc1OC)[C@H]1C[C@@H](COC(=O)C[C@H]3CCCN3)[C@H](CC(C)C)CN1CC2]
4-24 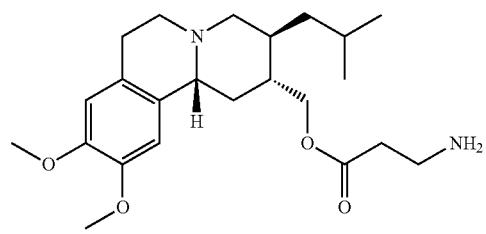 [SMILES: COc1cc2c(cc1OC)[C@H]1C[C@@H](COC(=O)CCN)[C@H](CC(C)C)CN1CC2]
4-28 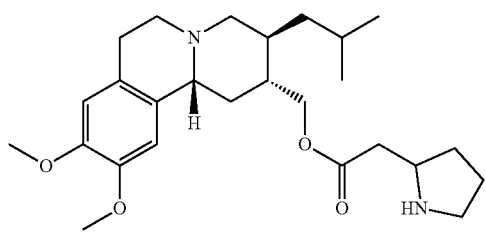 [SMILES: COc1cc2c(cc1OC)[C@H]1C[C@@H](COC(=O)CC3CCCN3)[C@H](CC(C)C)CN1CC2]

-continued
4-29 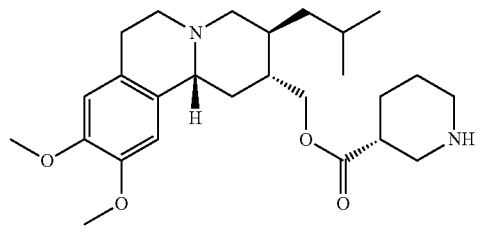 [SMILES: COc1cc2c(cc1OC)[C@H]1C[C@@H](COC(=O)[C@@H]3CCCNC3)[C@H](CC(C)C)CN1CC2]
4-30 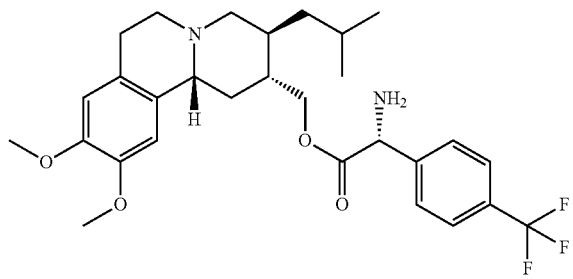 [SMILES: COc1cc2c(cc1OC)[C@H]1C[C@@H](COC(=O)[C@H](N)c3ccc(C(F)(F)F)cc3)[C@H](CC(C)C)CN1CC2]
4-31 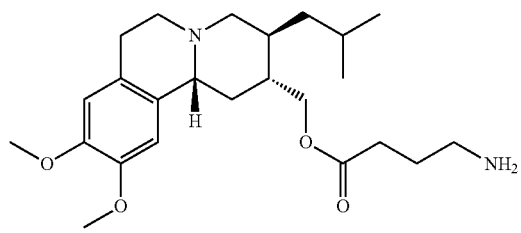 [SMILES: COc1cc2c(cc1OC)[C@H]1C[C@@H](COC(=O)CCCN)[C@H](CC(C)C)CN1CC2]
4-33 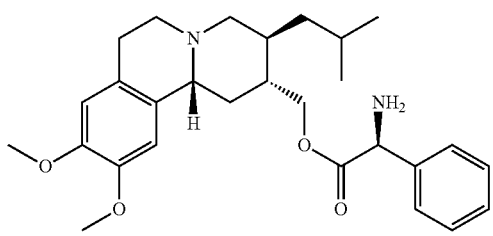 [SMILES: COc1cc2c(cc1OC)[C@H]1C[C@@H](COC(=O)[C@@H](N)c3ccccc3)[C@H](CC(C)C)CN1CC2]
4-34 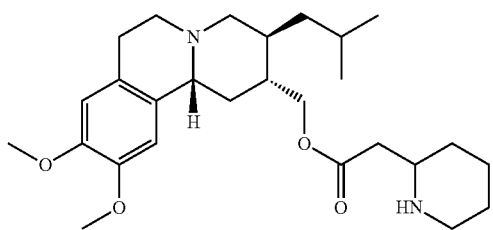 [SMILES: COc1cc2c(cc1OC)[C@H]1C[C@@H](COC(=O)CC3CCCCN3)[C@H](CC(C)C)CN1CC2]
4-36 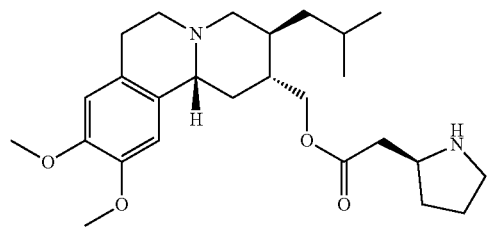 [SMILES: COc1cc2c(cc1OC)[C@H]1C[C@@H](COC(=O)C[C@@H]3CCCN3)[C@H](CC(C)C)CN1CC2]

4-37
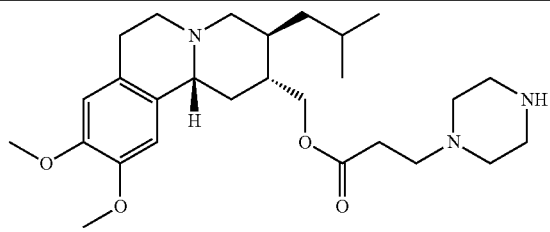
4-38
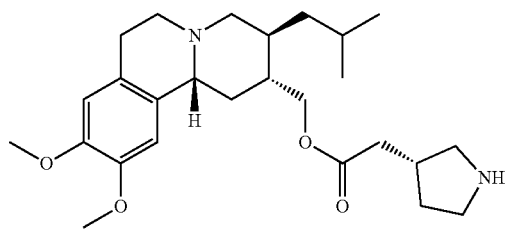 [SMILES: COc1cc2c(cc1OC)[C@H]1C[C@@H](COC(=O)C[C@H]3CCNC3)[C@H](CC(C)C)CN1CC2]
or a pharmaceutically acceptable salt or solvate thereof.
5. The pharmaceutical composition of claim 1, wherein $R^1$ is —C(=O)heterocyclyl, and wherein heterocyclyl is optionally substituted with $R^{10}$ and/or $R^{20}$.
6. The pharmaceutical composition of claim 1, wherein the compound is selected from one of the following:
2-6
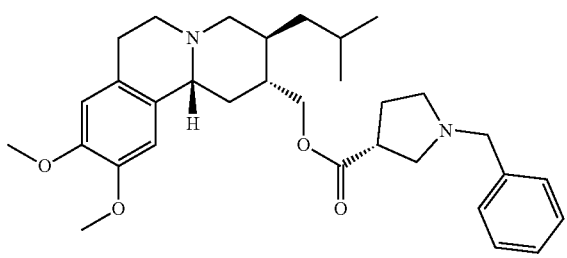 [SMILES: COc1cc2c(cc1OC)[C@H]1C[C@@H](COC(=O)[C@@H]3CCN(Cc4ccccc4)C3)[C@H](CC(C)C)CN1CC2]
2-11
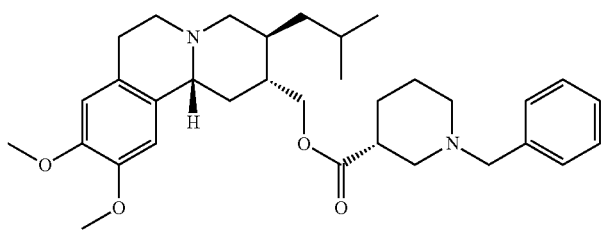 [SMILES: COc1cc2c(cc1OC)[C@H]1C[C@@H](COC(=O)[C@@H]3CCCN(Cc4ccccc4)C3)[C@H](CC(C)C)CN1CC2]
2-12
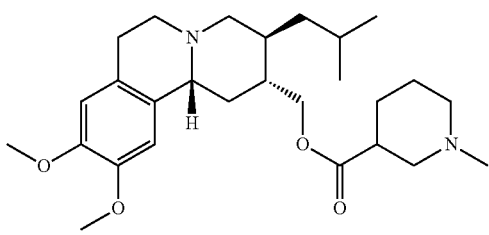

-continued
2-18
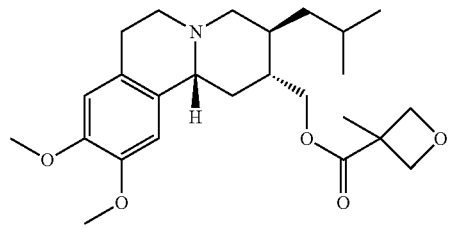 [SMILES: COc1cc2c(cc1OC)[C@H]1C[C@@H](COC(=O)C3(C)COC3)[C@H](CC(C)C)CN1CC2]
2-21
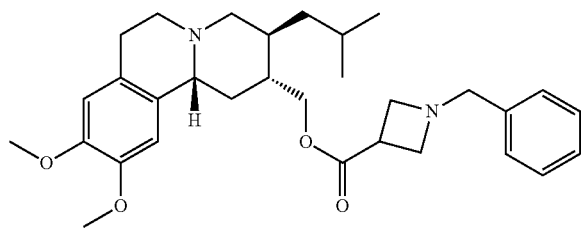 [SMILES: COc1cc2c(cc1OC)[C@H]1C[C@@H](COC(=O)C3CN(Cc4ccccc4)C3)[C@H](CC(C)C)CN1CC2]
2-22
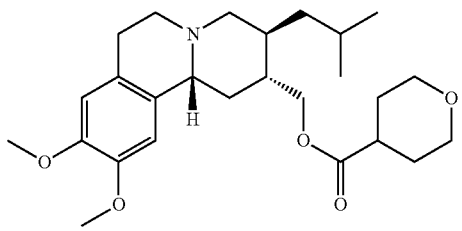 [SMILES: COc1cc2c(cc1OC)[C@H]1C[C@@H](COC(=O)C3CCOCC3)[C@H](CC(C)C)CN1CC2]
2-25
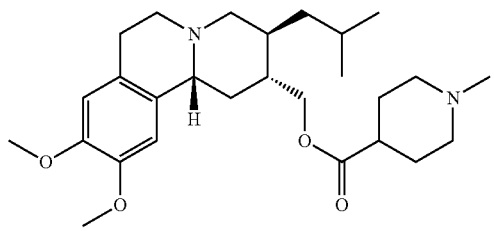
2-26
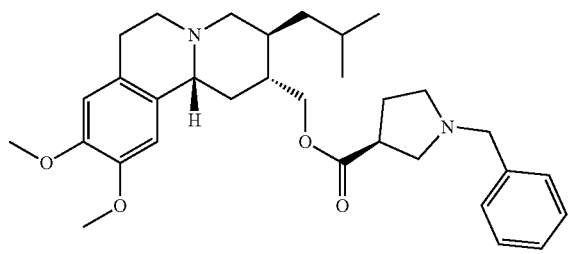 [SMILES: COc1cc2c(cc1OC)[C@H]1C[C@@H](COC(=O)[C@H]3CCN(Cc4ccccc4)C3)[C@H](CC(C)C)CN1CC2]
2-27
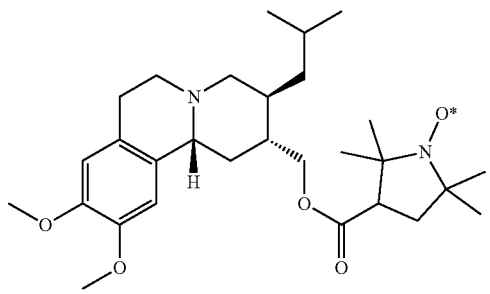

-continued
2-31 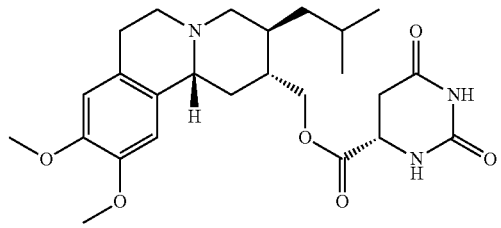 [SMILES: COc1cc2c(cc1OC)[C@H]1C[C@@H](COC(=O)[C@@H]3CC(=O)NC(=O)N3)[C@H](CC(C)C)CN1CC2]
2-37 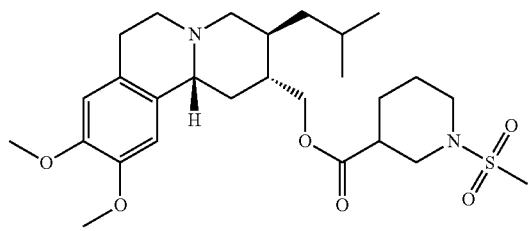
4-1 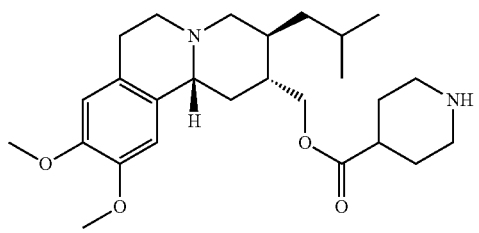 [SMILES: COc1cc2c(cc1OC)[C@H]1C[C@@H](COC(=O)C3CCNCC3)[C@H](CC(C)C)CN1CC2]
4-3 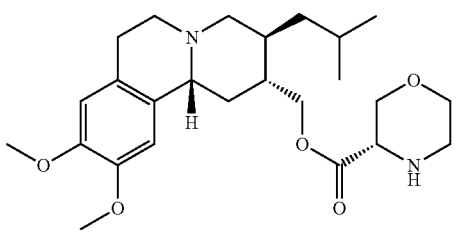 [SMILES: COc1cc2c(cc1OC)[C@H]1C[C@@H](COC(=O)[C@@H]3COCCN3)[C@H](CC(C)C)CN1CC2]
4-4 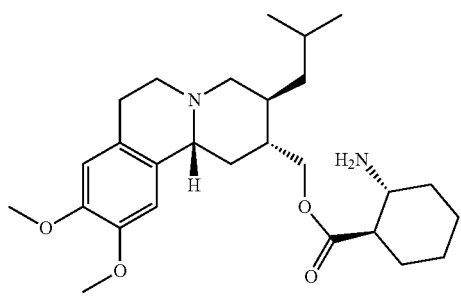 [SMILES: COc1cc2c(cc1OC)[C@H]1C[C@@H](COC(=O)[C@@H]3CCCC[C@H]3N)[C@H](CC(C)C)CN1CC2]
4-5 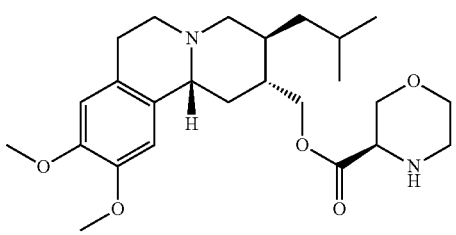 [SMILES: COc1cc2c(cc1OC)[C@H]1C[C@@H](COC(=O)[C@H]3COCCN3)[C@H](CC(C)C)CN1CC2]

-continued
4-6 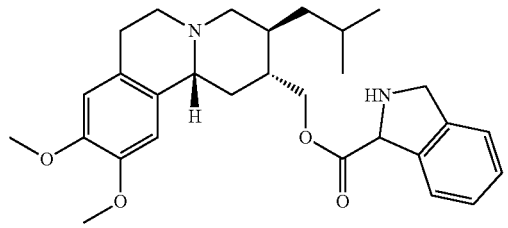 [SMILES: COc1cc2c(cc1OC)[C@H]1C[C@@H](COC(=O)C3NCc4ccccc43)[C@H](CC(C)C)CN1CC2]
4-7 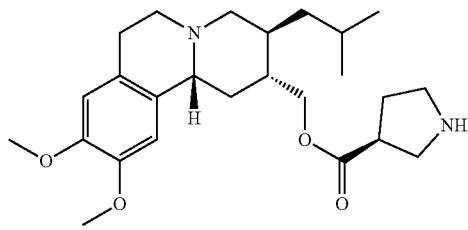 [SMILES: COc1cc2c(cc1OC)[C@H]1C[C@@H](COC(=O)[C@H]3CCNC3)[C@H](CC(C)C)CN1CC2]
4-8 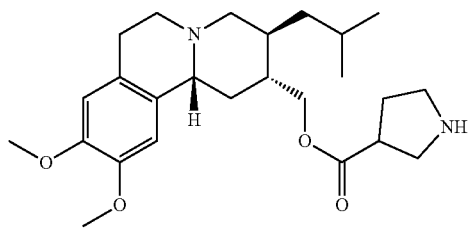 [SMILES: COc1cc2c(cc1OC)[C@H]1C[C@@H](COC(=O)C3CCNC3)[C@H](CC(C)C)CN1CC2]
4-11 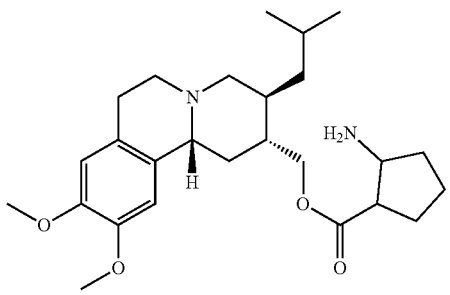 [SMILES: COc1cc2c(cc1OC)[C@H]1C[C@@H](COC(=O)C3CCCC3N)[C@H](CC(C)C)CN1CC2]
4-13 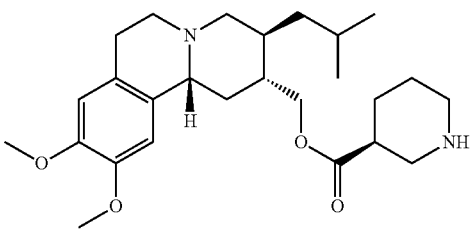 [SMILES: COc1cc2c(cc1OC)[C@H]1C[C@@H](COC(=O)[C@H]3CCCNC3)[C@H](CC(C)C)CN1CC2]
4-15 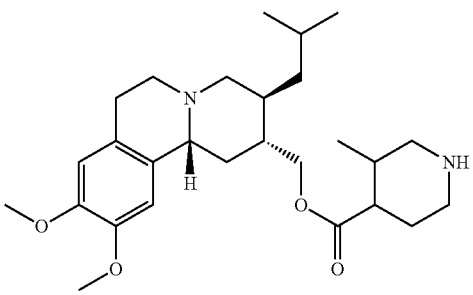 [SMILES: COc1cc2c(cc1OC)[C@H]1C[C@@H](COC(=O)C3CCNCC3C)[C@H](CC(C)C)CN1CC2]

-continued
4-20 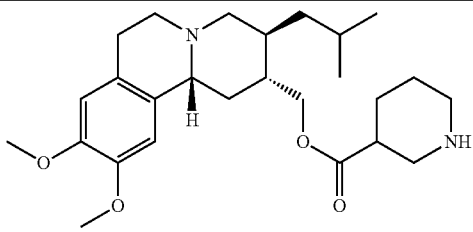
4-21 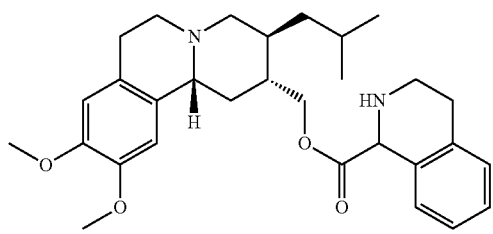 [SMILES: COc1cc2c(cc1OC)[C@H]1C[C@@H](COC(=O)C3NCCc4ccccc43)[C@H](CC(C)C)CN1CC2]
4-22 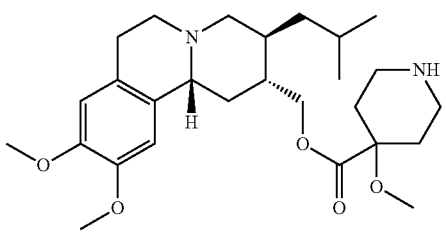 [SMILES: COc1cc2c(cc1OC)[C@H]1C[C@@H](COC(=O)C3(OC)CCNCC3)[C@H](CC(C)C)CN1CC2]
4-26 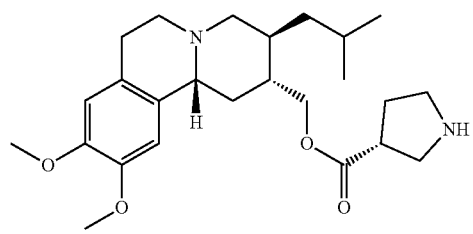 [SMILES: COc1cc2c(cc1OC)[C@H]1C[C@@H](COC(=O)[C@@H]3CCNC3)[C@H](CC(C)C)CN1CC2]
4-27 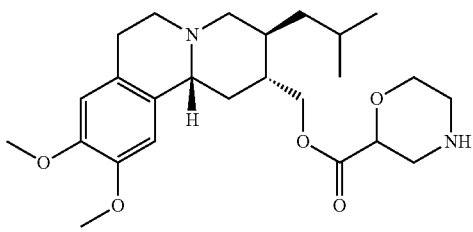 [SMILES: COc1cc2c(cc1OC)[C@H]1C[C@@H](COC(=O)C3CNCCO3)[C@H](CC(C)C)CN1CC2]
4-29 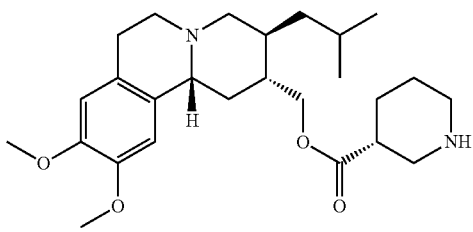 [SMILES: COc1cc2c(cc1OC)[C@H]1C[C@@H](COC(=O)[C@@H]3CCCNC3)[C@H](CC(C)C)CN1CC2]
4-32 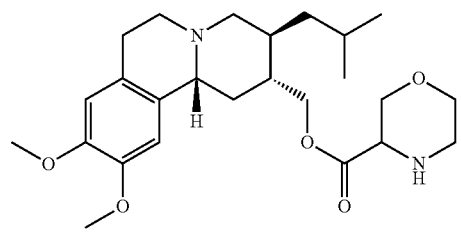 [SMILES: COc1cc2c(cc1OC)[C@H]1C[C@@H](COC(=O)C3COCCN3)[C@H](CC(C)C)CN1CC2]

4-35 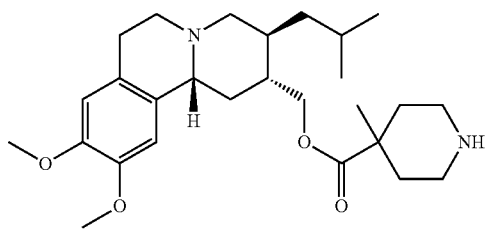 [SMILES: COc1cc2c(cc1OC)[C@H]1C[C@@H](COC(=O)C3(C)CCNCC3)[C@H](CC(C)C)CN1CC2]
5-4 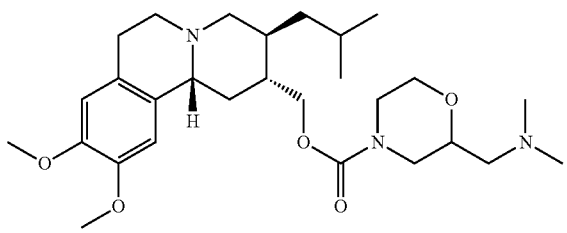
5-6 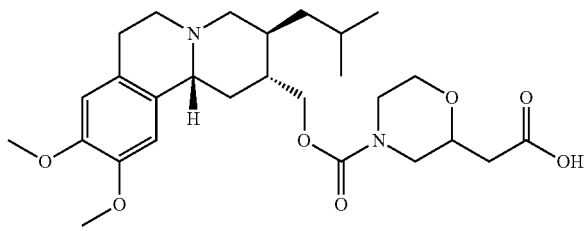 [SMILES: COc1cc2c(cc1OC)[C@H]1C[C@@H](COC(=O)N3CCOC(CC(=O)O)C3)[C@H](CC(C)C)CN1CC2]
5-7 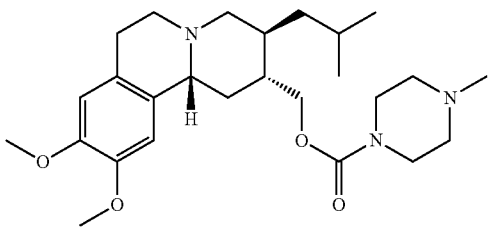
5-8 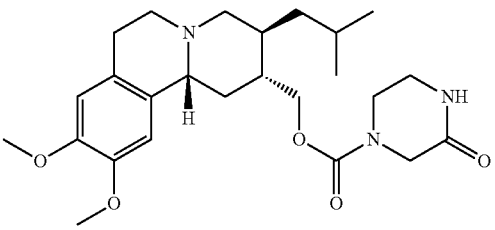 [SMILES: COc1cc2c(cc1OC)[C@H]1C[C@@H](COC(=O)N3CCNC(=O)C3)[C@H](CC(C)C)CN1CC2]
5-12 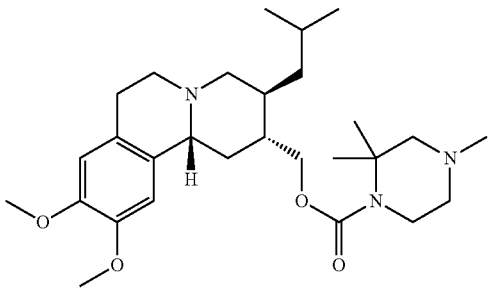

-continued
5-13
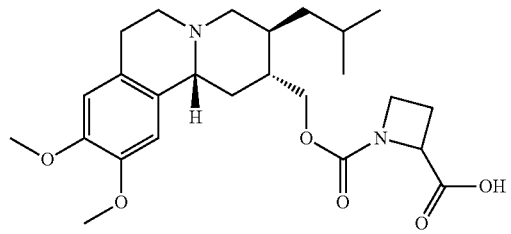 [SMILES: COc1cc2c(cc1OC)[C@H]1C[C@@H](COC(=O)N3CCC3C(=O)O)[C@H](CC(C)C)CN1CC2]
5-14
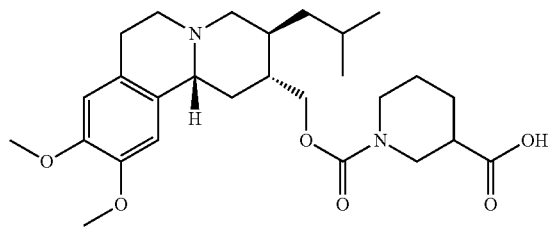 [SMILES: COc1cc2c(cc1OC)[C@H]1C[C@@H](COC(=O)N3CCCC(C(=O)O)C3)[C@H](CC(C)C)CN1CC2]
5-15
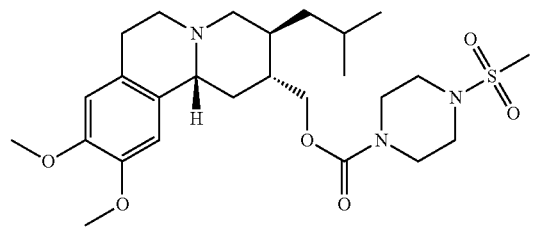
5-18
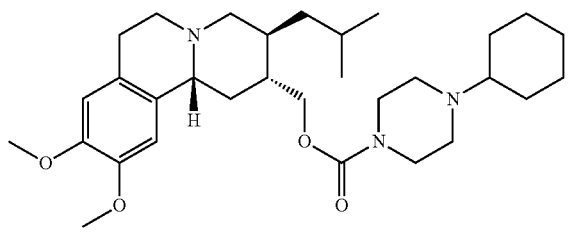 [SMILES: COc1cc2c(cc1OC)[C@H]1C[C@@H](COC(=O)N3CCN(C4CCCCC4)CC3)[C@H](CC(C)C)CN1CC2]
5-21
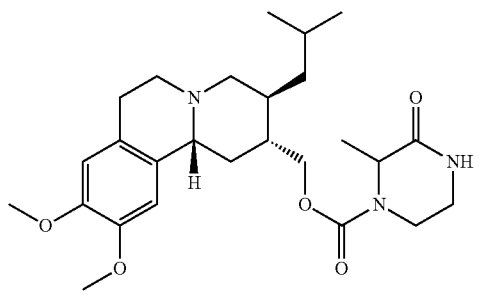 [SMILES: COc1cc2c(cc1OC)[C@H]1C[C@@H](COC(=O)N3CCNC(=O)C3C)[C@H](CC(C)C)CN1CC2]
5-24
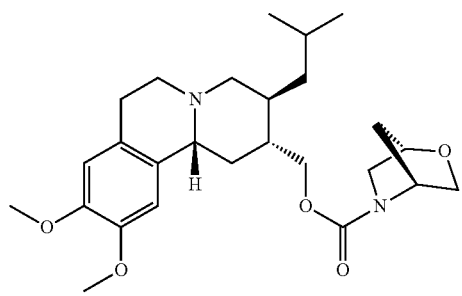 [SMILES: COc1cc2c(cc1OC)[C@H]1C[C@@H](COC(=O)N3C[C@@H]4C[C@H]3CO4)[C@H](CC(C)C)CN1CC2]

5-27 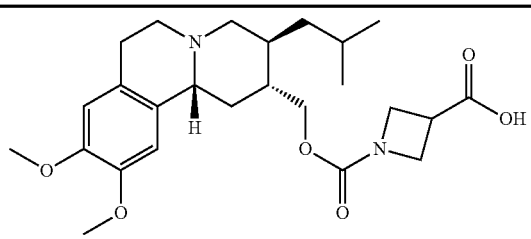
5-31 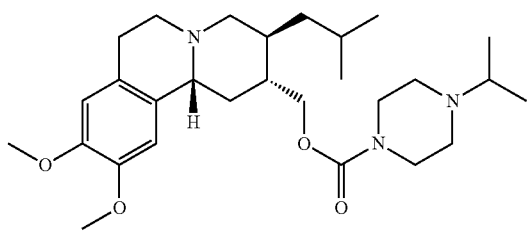 [SMILES: COc1cc2c(cc1OC)[C@H]1C[C@@H](COC(=O)N3CCN(C(C)C)CC3)[C@H](CC(C)C)CN1CC2]
5-37 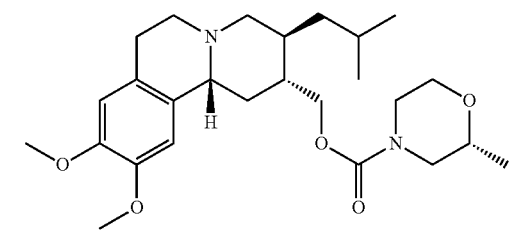
5-43 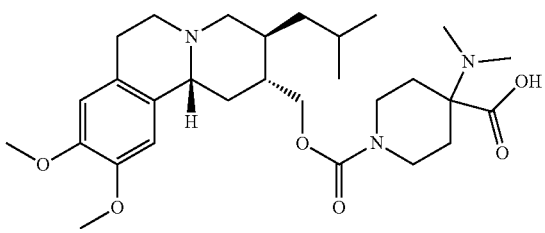 [SMILES: COc1cc2c(cc1OC)[C@H]1C[C@@H](COC(=O)N3CCC(C(=O)O)(N(C)C)CC3)[C@H](CC(C)C)CN1CC2]
5-44 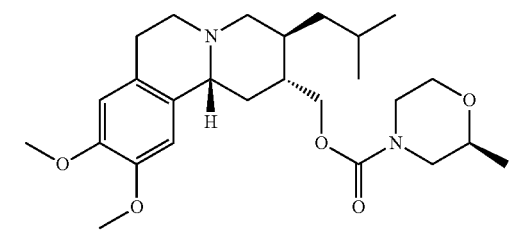
5-48 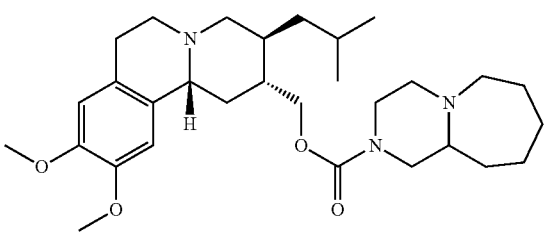 [SMILES: COc1cc2c(cc1OC)[C@H]1C[C@@H](COC(=O)N3CCN4CCCCCC4C3)[C@H](CC(C)C)CN1CC2]
5-49 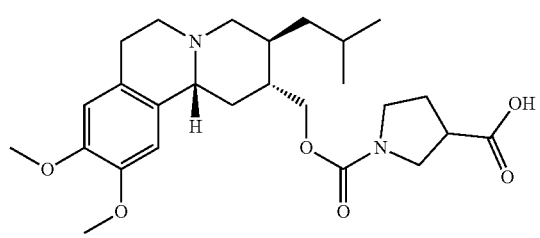 [SMILES: COc1cc2c(cc1OC)[C@H]1C[C@@H](COC(=O)N3CCC(C(=O)O)C3)[C@H](CC(C)C)CN1CC2]

-continued
5-50
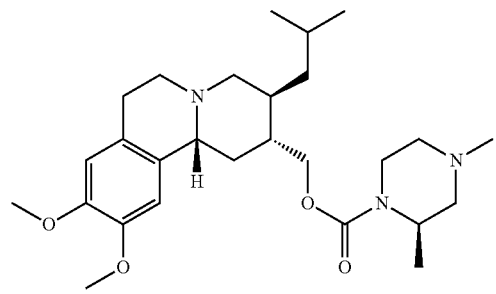
5-52
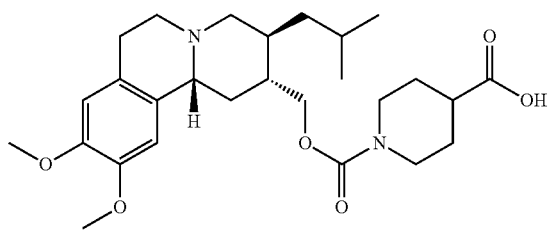 [SMILES: COc1cc2c(cc1OC)[C@H]1C[C@@H](COC(=O)N3CCC(C(=O)O)CC3)[C@H](CC(C)C)CN1CC2]
5-53
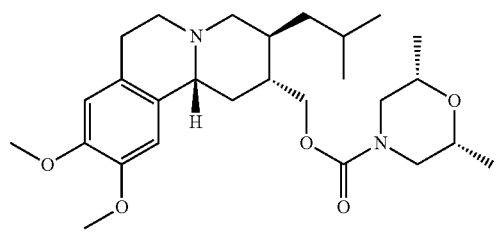
5-54
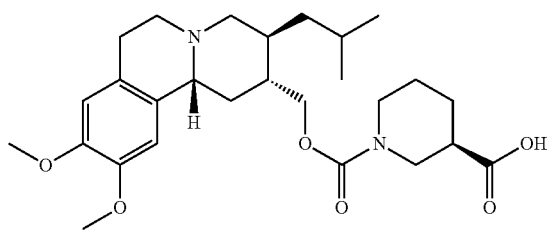 [SMILES: COc1cc2c(cc1OC)[C@H]1C[C@@H](COC(=O)N3CCC[C@@H](C(=O)O)C3)[C@H](CC(C)C)CN1CC2]
6-1
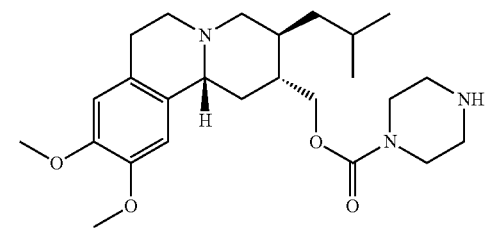 [SMILES: COc1cc2c(cc1OC)[C@H]1C[C@@H](COC(=O)N3CCNCC3)[C@H](CC(C)C)CN1CC2]
6-2
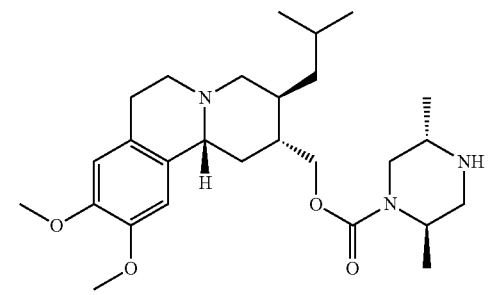 [SMILES: COc1cc2c(cc1OC)[C@H]1C[C@@H](COC(=O)N3C[C@H](C)NC[C@H]3C)[C@H](CC(C)C)CN1CC2]

6-3 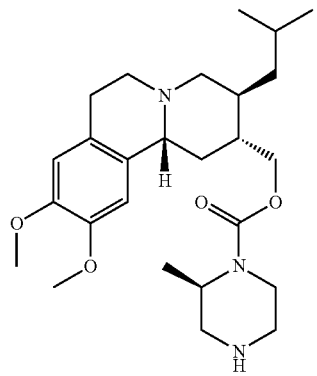 [SMILES: COc1cc2c(cc1OC)[C@H]1C[C@@H](COC(=O)N3CCNC[C@H]3C)[C@H](CC(C)C)CN1CC2]
6-4 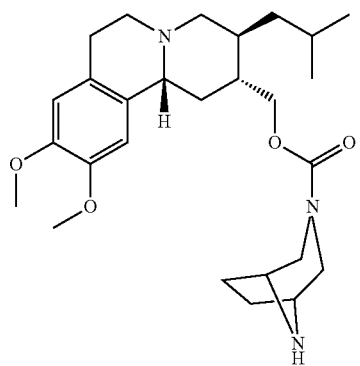 [SMILES: COc1cc2c(cc1OC)[C@H]1C[C@@H](COC(=O)N3CC4CCC(C3)N4)[C@H](CC(C)C)CN1CC2]
6-5 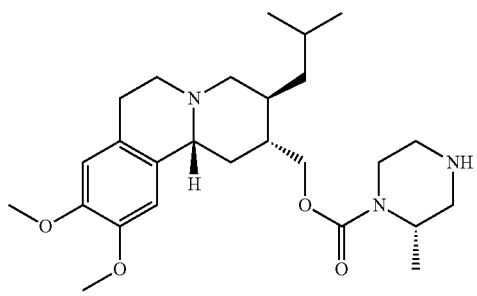 [SMILES: COc1cc2c(cc1OC)[C@H]1C[C@@H](COC(=O)N3CCNC[C@@H]3C)[C@H](CC(C)C)CN1CC2]
6-6 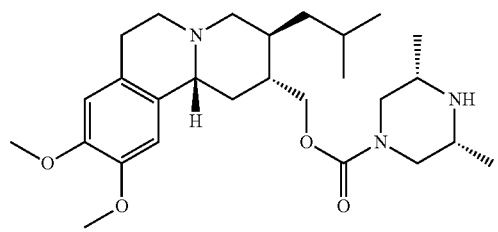
6-7 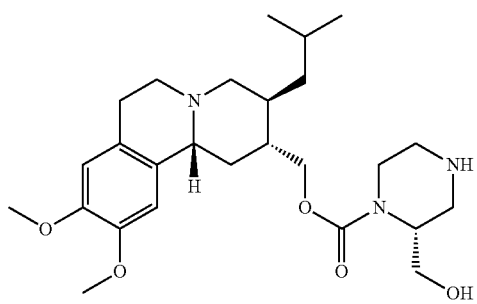 [SMILES: COc1cc2c(cc1OC)[C@H]1C[C@@H](COC(=O)N3CCNC[C@@H]3CO)[C@H](CC(C)C)CN1CC2]

6-8 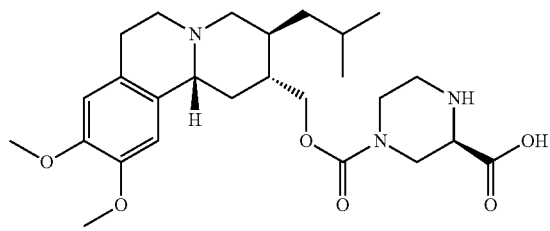 [SMILES: COc1cc2c(cc1OC)[C@H]1C[C@@H](COC(=O)N3CCN[C@@H](C(=O)O)C3)[C@H](CC(C)C)CN1CC2]
6-9 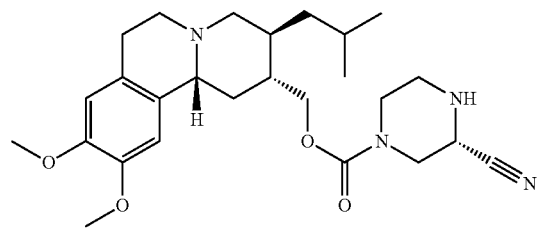 [SMILES: COc1cc2c(cc1OC)[C@H]1C[C@@H](COC(=O)N3CCN[C@H](C#N)C3)[C@H](CC(C)C)CN1CC2]
6-10 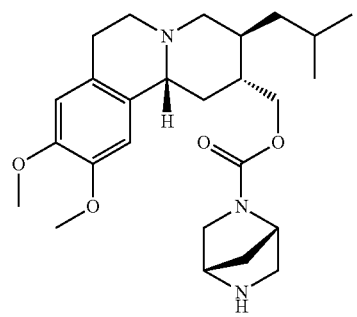 [SMILES: COc1cc2c(cc1OC)[C@H]1C[C@@H](COC(=O)N3C[C@@H]4C[C@H]3CN4)[C@H](CC(C)C)CN1CC2]
6-11 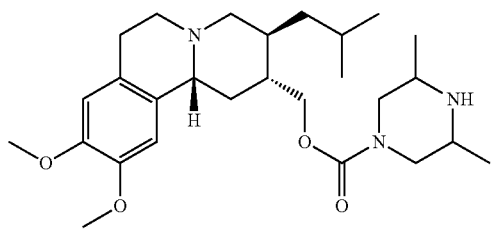
6-12 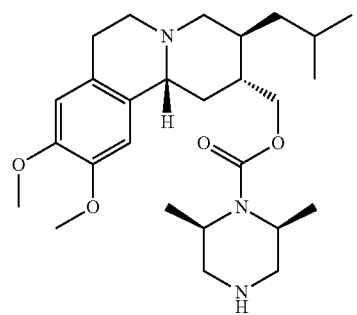 [SMILES: COc1cc2c(cc1OC)[C@H]1C[C@@H](COC(=O)N3[C@H](C)CNC[C@@H]3C)[C@H](CC(C)C)CN1CC2]

6-13
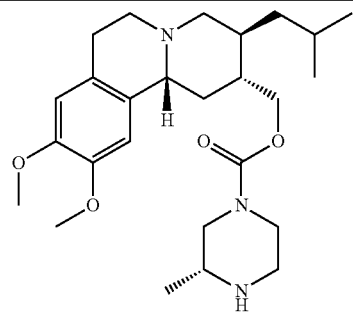
6-14
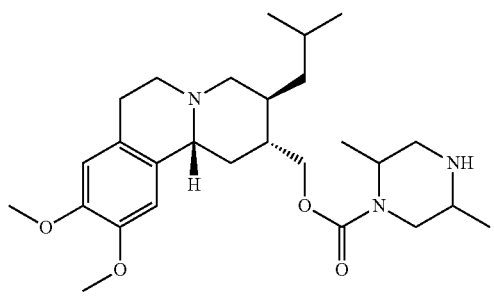
or a pharmaceutically acceptable salt or solvate thereof.
7. The pharmaceutical composition of claim 1, wherein $R^1$ is —C(=O)carbocyclyl, and wherein carbocyclyl is optionally substituted with $R^{10}$ and/or $R^{20}$.
8. The pharmaceutical composition of claim 1, wherein the compound is selected from one of the following:
2-20
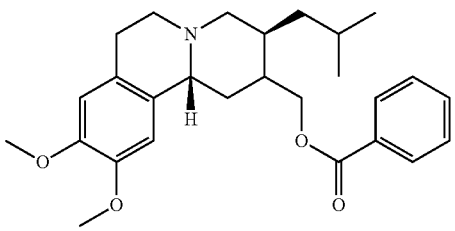 [SMILES: COc1cc2c(cc1OC)[C@H]1CC(COC(=O)c3ccccc3)[C@H](CC(C)C)CN1CC2]
2-38
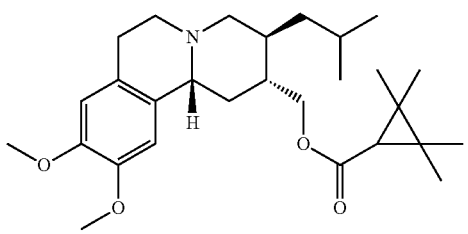
3-4
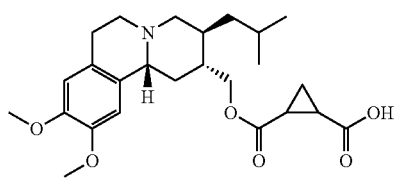 [SMILES: COc1cc2c(cc1OC)[C@H]1C[C@@H](COC(=O)C3CC3C(=O)O)[C@H](CC(C)C)CN1CC2]
3-5
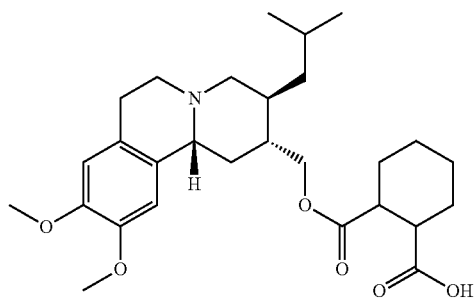 [SMILES: COc1cc2c(cc1OC)[C@H]1C[C@@H](COC(=O)C3CCCCC3C(=O)O)[C@H](CC(C)C)CN1CC2]
3-6
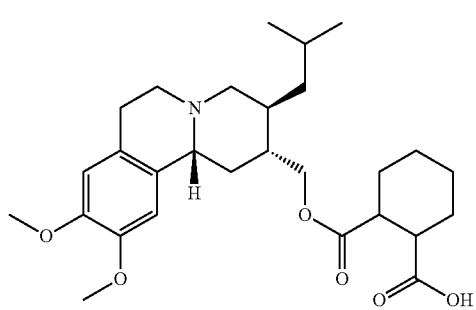 [SMILES: COc1cc2c(cc1OC)[C@H]1C[C@@H](COC(=O)C3CCCCC3C(=O)O)[C@H](CC(C)C)CN1CC2]
4-18
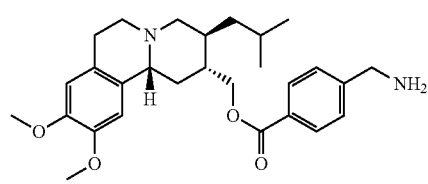 [SMILES: COc1cc2c(cc1OC)[C@H]1C[C@@H](COC(=O)c3ccc(CN)cc3)[C@H](CC(C)C)CN1CC2]

4-25 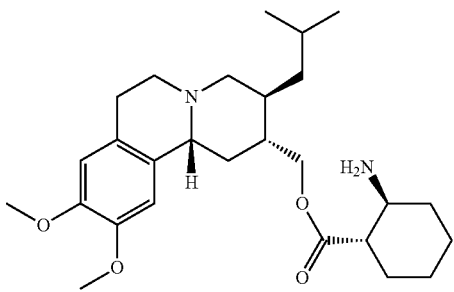 [SMILES: COc1cc2c(cc1OC)[C@H]1C[C@@H](COC(=O)[C@H]3CCCC[C@@H]3N)[C@H](CC(C)C)CN1CC2]
or a pharmaceutically acceptable salt or solvate thereof.
9. The pharmaceutical composition of claim 1, wherein $R^1$—C(=O)N($R_3$)alkyl, and wherein alkyl is optionally substituted with $R^{10}$ and/or $R^{20}$.
10. The pharmaceutical composition of claim 1, wherein the compound is selected from one of the following:
5-1 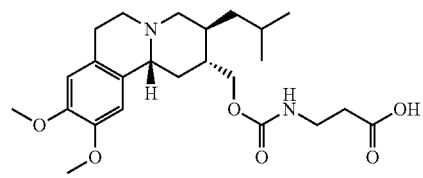 [SMILES: COc1cc2c(cc1OC)[C@H]1C[C@@H](COC(=O)NCCC(=O)O)[C@H](CC(C)C)CN1CC2]
5-2 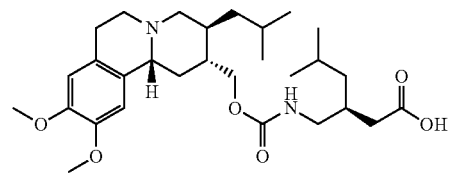 [SMILES: COc1cc2c(cc1OC)[C@H]1C[C@@H](COC(=O)NC[C@H](CC(=O)O)CC(C)C)[C@H](CC(C)C)CN1CC2]
5-3 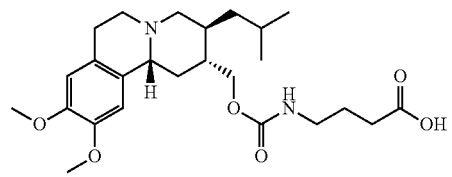 [SMILES: COc1cc2c(cc1OC)[C@H]1C[C@@H](COC(=O)NCCCC(=O)O)[C@H](CC(C)C)CN1CC2]
5-5 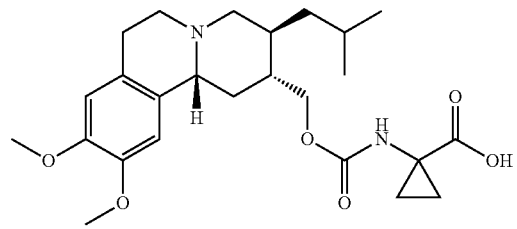 [SMILES: COc1cc2c(cc1OC)[C@H]1C[C@@H](COC(=O)NC3(C(=O)O)CC3)[C@H](CC(C)C)CN1CC2]
5-10 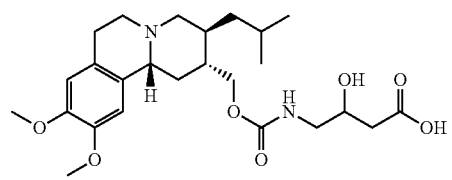 [SMILES: COc1cc2c(cc1OC)[C@H]1C[C@@H](COC(=O)NCC(O)CC(=O)O)[C@H](CC(C)C)CN1CC2]
5-11 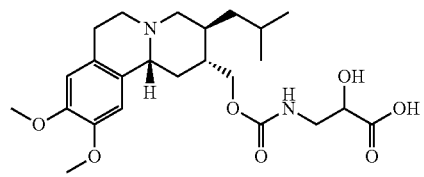 [SMILES: COc1cc2c(cc1OC)[C@H]1C[C@@H](COC(=O)NCC(O)C(=O)O)[C@H](CC(C)C)CN1CC2]
5-16 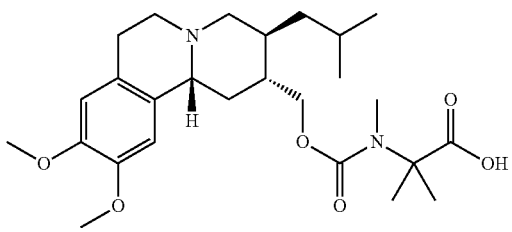 [SMILES: COc1cc2c(cc1OC)[C@H]1C[C@@H](COC(=O)N(C)C(C)(C)C(=O)O)[C@H](CC(C)C)CN1CC2]
5-17 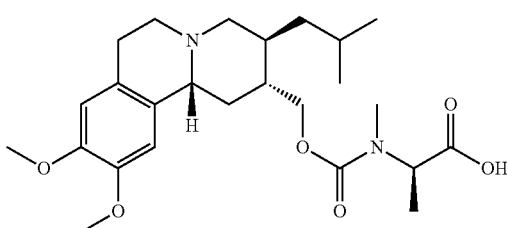
5-19 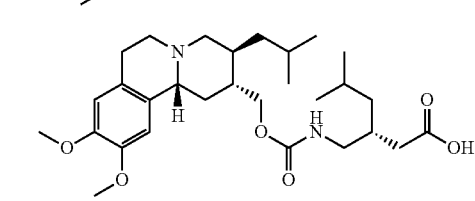
5-20 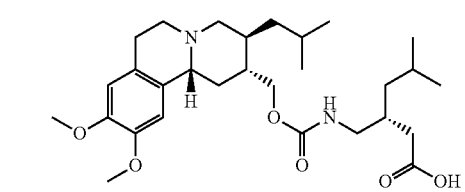 [SMILES: COc1cc2c(cc1OC)[C@H]1C[C@@H](COC(=O)NC[C@@H](CC(=O)O)CC(C)C)[C@H](CC(C)C)CN1CC2]
5-22 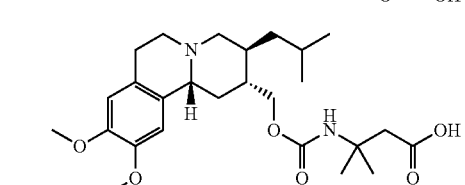
5-23 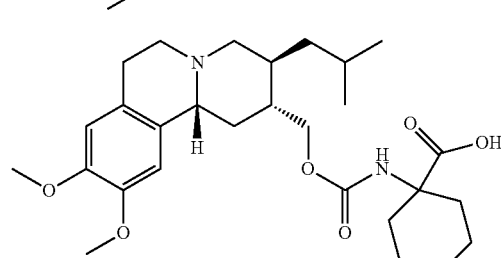
5-25 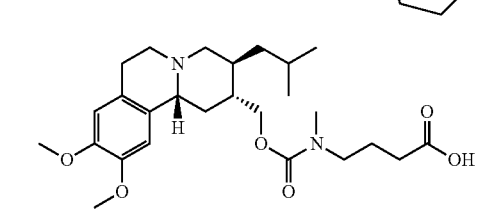

| | |
|---|---|
| 5-26 | 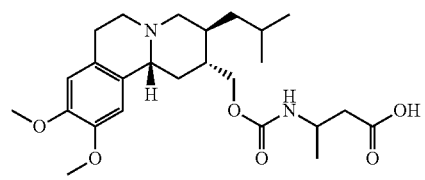 [SMILES: COc1cc2c(cc1OC)[C@H]1C[C@@H](COC(=O)NC(C)CC(=O)O)[C@H](CC(C)C)CN1CC2] |
| 5-28 | 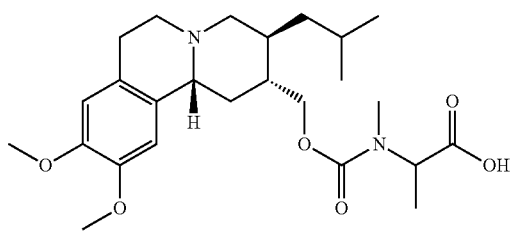 |
| 5-29 | 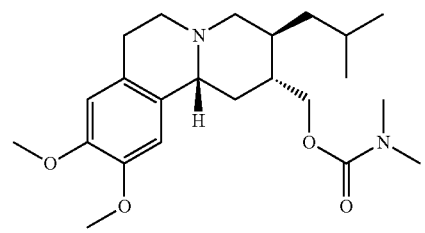 |
| 5-30 | 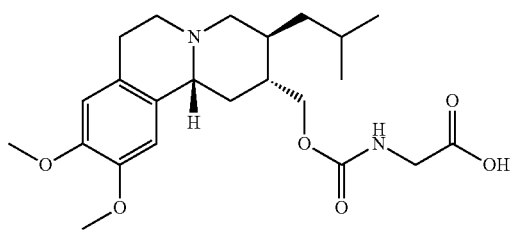 [SMILES: COc1cc2c(cc1OC)[C@H]1C[C@@H](COC(=O)NCC(=O)O)[C@H](CC(C)C)CN1CC2] |
| 5-32 | 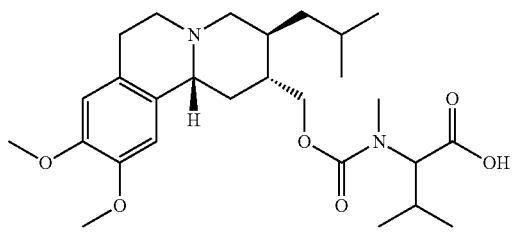 [SMILES: COc1cc2c(cc1OC)[C@H]1C[C@@H](COC(=O)N(C)C(C(=O)O)C(C)C)[C@H](CC(C)C)CN1CC2] |
| 5-33 | 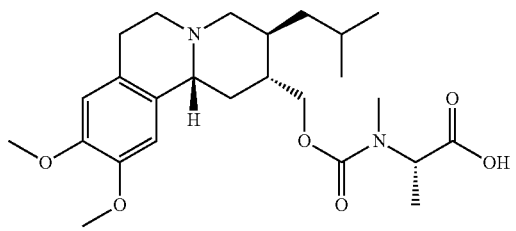 [SMILES: COc1cc2c(cc1OC)[C@H]1C[C@@H](COC(=O)N(C)[C@@H](C)C(=O)O)[C@H](CC(C)C)CN1CC2] |
| 5-34 | 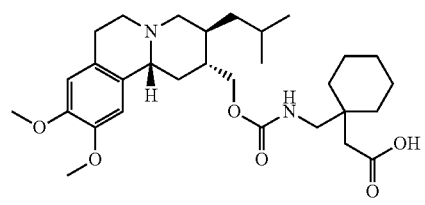 [SMILES: COc1cc2c(cc1OC)[C@H]1C[C@@H](COC(=O)NCC3(CC(=O)O)CCCCC3)[C@H](CC(C)C)CN1CC2] |
| | |
|---|---|
| 5-36 | 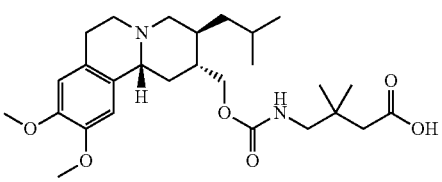 [SMILES: COc1cc2c(cc1OC)[C@H]1C[C@@H](COC(=O)NCC(C)(C)CC(=O)O)[C@H](CC(C)C)CN1CC2] |
| 5-38 | 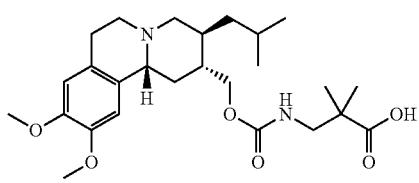 [SMILES: COc1cc2c(cc1OC)[C@H]1C[C@@H](COC(=O)NCC(C)(C)C(=O)O)[C@H](CC(C)C)CN1CC2] |
| 5-39 | 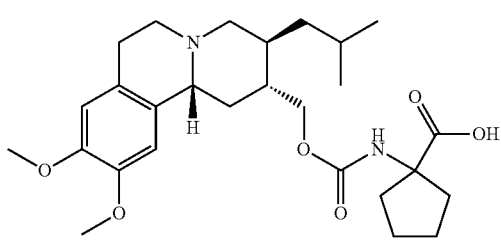 [SMILES: COc1cc2c(cc1OC)[C@H]1C[C@@H](COC(=O)NC3(C(=O)O)CCCC3)[C@H](CC(C)C)CN1CC2] |
| 5-42 | 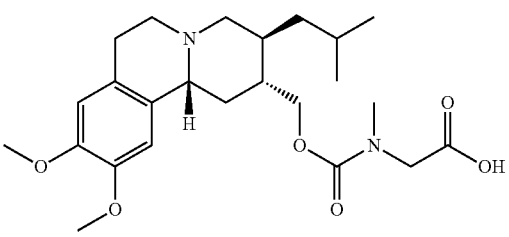 [SMILES: COc1cc2c(cc1OC)[C@H]1C[C@@H](COC(=O)N(C)CC(=O)O)[C@H](CC(C)C)CN1CC2] |
| 5-45 | 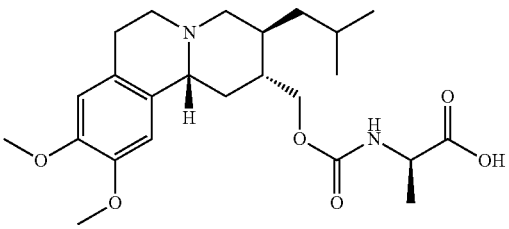 [SMILES: COc1cc2c(cc1OC)[C@H]1C[C@@H](COC(=O)N[C@H](C)C(=O)O)[C@H](CC(C)C)CN1CC2] |
| 5-46 | 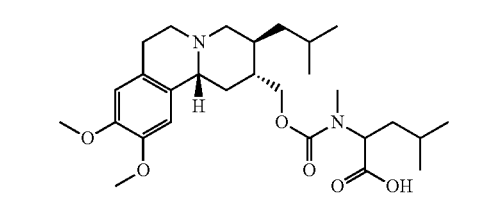 [SMILES: COc1cc2c(cc1OC)[C@H]1C[C@@H](COC(=O)N(C)C(CC(C)C)C(=O)O)[C@H](CC(C)C)CN1CC2] |
| 5-47 | 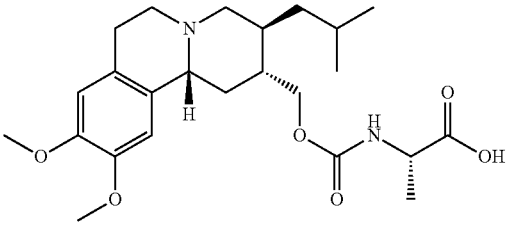 [SMILES: COc1cc2c(cc1OC)[C@H]1C[C@@H](COC(=O)N[C@@H](C)C(=O)O)[C@H](CC(C)C)CN1CC2] |

5-51 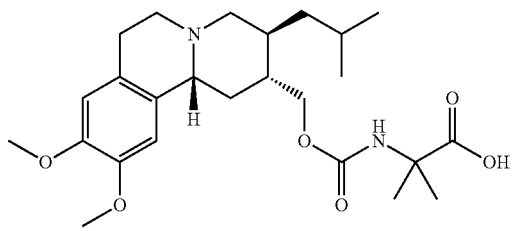 [SMILES: COc1cc2c(cc1OC)[C@H]1C[C@@H](COC(=O)NC(C)(C)C(=O)O)[C@H](CC(C)C)CN1CC2]

5-55 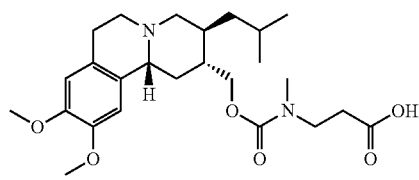 [SMILES: COc1cc2c(cc1OC)[C@H]1C[C@@H](COC(=O)N(C)CCC(=O)O)[C@H](CC(C)C)CN1CC2]

5-56 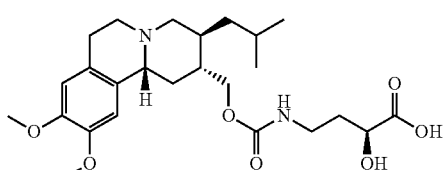

5-57 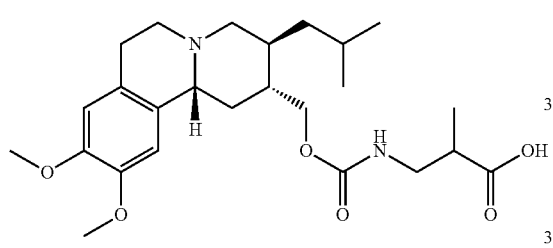

or a pharmaceutically acceptable salt or solvate thereof.

11. The pharmaceutical composition of claim 1, wherein $R^1$ is —C(=O)N($R_3$)carbocycle, and wherein carbocycle is optionally substituted with $R^{10}$ and/or $R^{20}$.

12. The pharmaceutical composition of claim 1, wherein the compound is selected from one of the following:

5-9 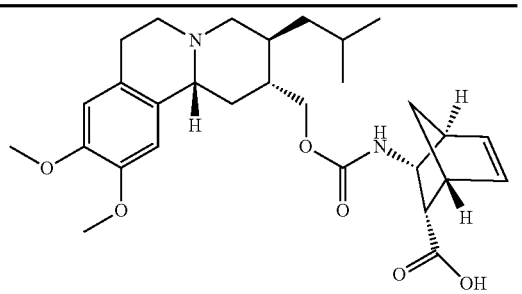

5-35 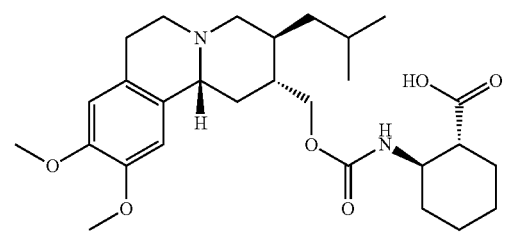 [SMILES: COc1cc2c(cc1OC)[C@H]1C[C@@H](COC(=O)N[C@@H]3CCCC[C@H]3C(=O)O)[C@H](CC(C)C)CN1CC2]

5-40 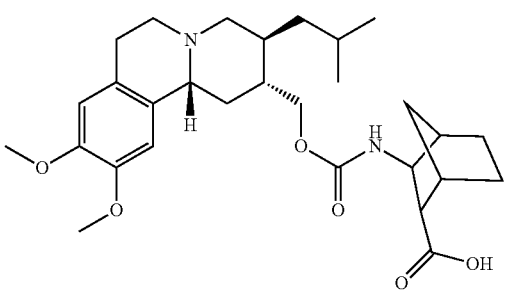 [SMILES: COc1cc2c(cc1OC)[C@H]1C[C@@H](COC(=O)NC3C4CCC(C4)C3C(=O)O)[C@H](CC(C)C)CN1CC2]

5-41 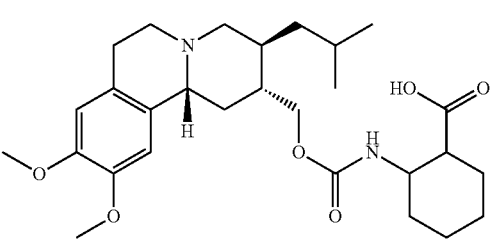 [SMILES: COc1cc2c(cc1OC)[C@H]1C[C@@H](COC(=O)NC3CCCCC3C(=O)O)[C@H](CC(C)C)CN1CC2]

or a pharmaceutically acceptable salt or solvate thereof.

13. The pharmaceutical composition of claim 1, wherein $R^1$—C(=O)Oalkyl, and wherein alkyl is optionally substituted with $R^{10}$ and/or $R^{20}$.

14. The pharmaceutical composition of claim 1, wherein the compound is:

8-1 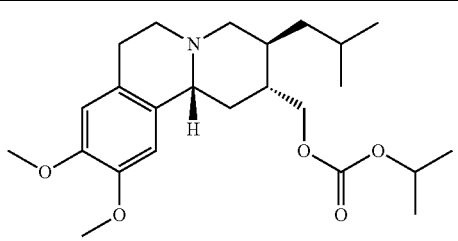

or a pharmaceutically acceptable salt or solvate thereof.

15. The pharmaceutical composition of claim 1, wherein —$R^1$ is alkyl, and wherein alkyl is optionally substituted with $R^{10}$ and/or $R^{20}$.

16. The pharmaceutical composition of claim 1, wherein the compound is:

9-1 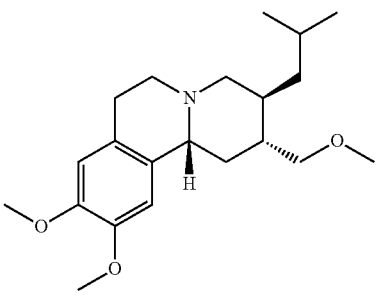

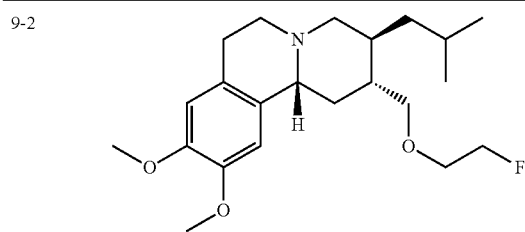
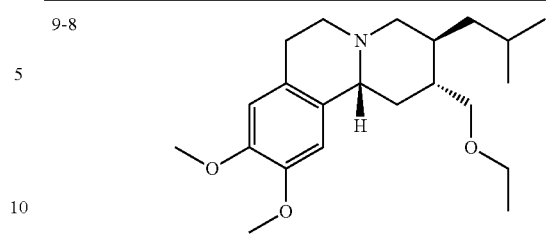

10-4
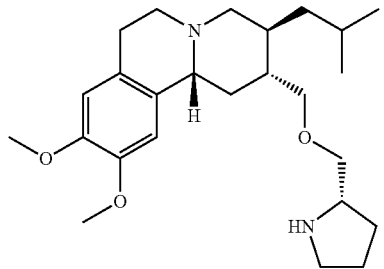 [SMILES: COc1cc2c(cc1OC)[C@H]1C[C@@H](COC[C@@H]3CCCN3)[C@H](CC(C)C)CN1CC2]

10-5
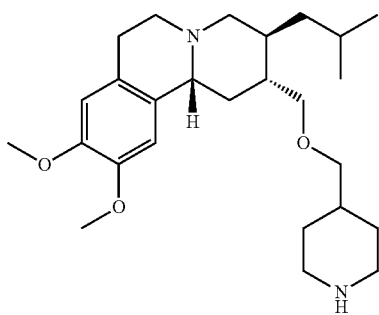 [SMILES: COc1cc2c(cc1OC)[C@H]1C[C@@H](COCC3CCNCC3)[C@H](CC(C)C)CN1CC2]

10-6
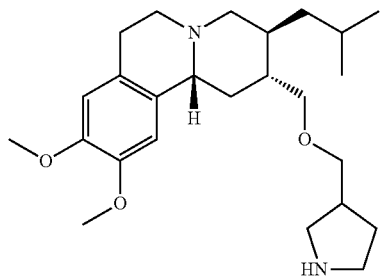 [SMILES: COc1cc2c(cc1OC)[C@H]1C[C@@H](COCC3CCNC3)[C@H](CC(C)C)CN1CC2]

10-7
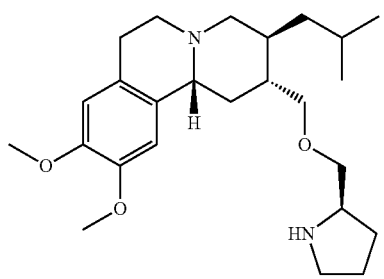 [SMILES: COc1cc2c(cc1OC)[C@H]1C[C@@H](COC[C@H]3CCCN3)[C@H](CC(C)C)CN1CC2]

or a pharmaceutically acceptable salt or solvate thereof.

17. A method of treating a hyperkinetic disorder that benefits from inhibiting vesicular monoamine transporter 2 (VMAT2) comprising administering to a subject having said disorder a pharmaceutically effective amount of a pharmaceutical composition of claim 1.

18. The method of claim 17, wherein the hyperkinetic disorder is Huntington's disease, tardive dyskinesia, Tourette's syndrome or tics.

19. The pharmaceutical composition of claim 4, wherein the compound is selected from one of the following:

2-10
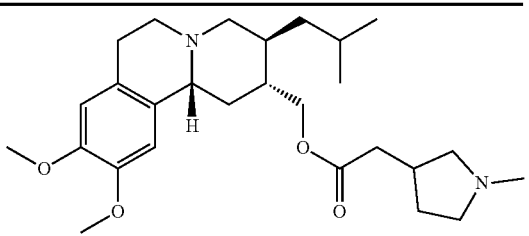

4-16
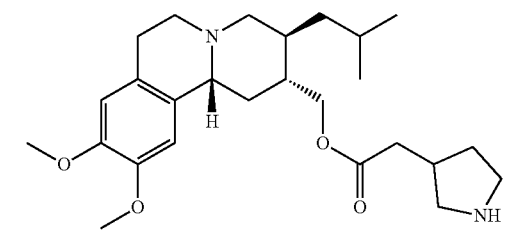 [SMILES: COc1cc2c(cc1OC)[C@H]1C[C@@H](COC(=O)CC3CCNC3)[C@H](CC(C)C)CN1CC2]

4-23
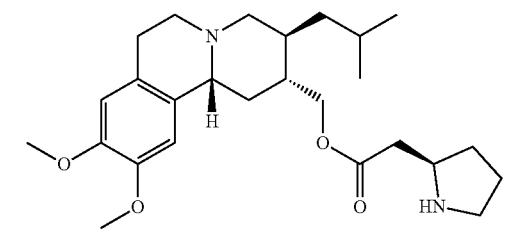 [SMILES: COc1cc2c(cc1OC)[C@H]1C[C@@H](COC(=O)C[C@H]3CCCN3)[C@H](CC(C)C)CN1CC2]

4-28
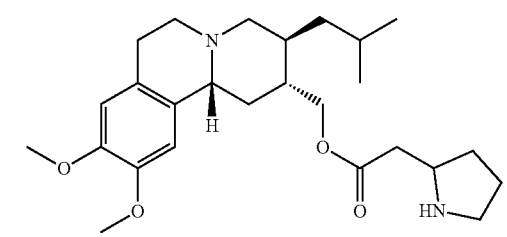 [SMILES: COc1cc2c(cc1OC)[C@H]1C[C@@H](COC(=O)CC3CCCN3)[C@H](CC(C)C)CN1CC2]

4-34
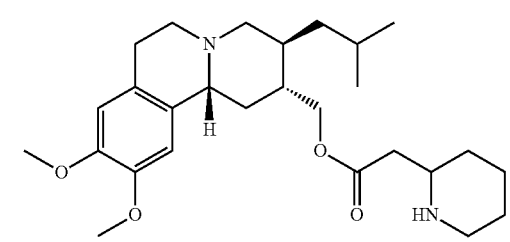 [SMILES: COc1cc2c(cc1OC)[C@H]1C[C@@H](COC(=O)CC3CCCCN3)[C@H](CC(C)C)CN1CC2]

4-36
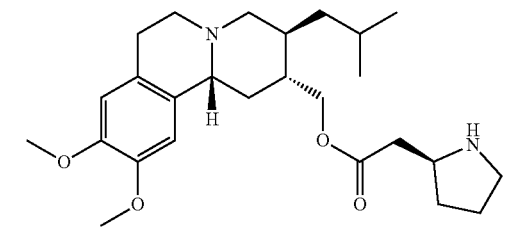 [SMILES: COc1cc2c(cc1OC)[C@H]1C[C@@H](COC(=O)C[C@@H]3CCCN3)[C@H](CC(C)C)CN1CC2]

4-38
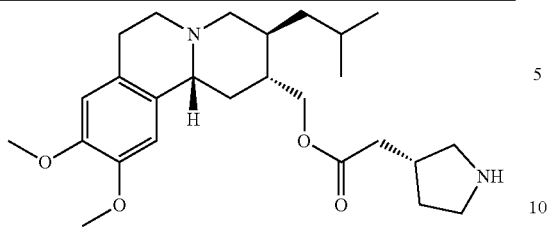
or a pharmaceutically acceptable salt thereof.
20. The pharmaceutical composition of claim 4, wherein the compound is:
2-10
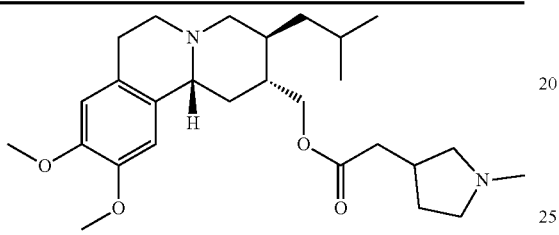
or a pharmaceutically acceptable salt thereof.
* * * * *